US010925966B2

(12) United States Patent
Wurth

(10) Patent No.: US 10,925,966 B2
(45) Date of Patent: Feb. 23, 2021

(54) ANTIBODY FORMULATIONS

(71) Applicant: Genentech, Inc., South San Francisco, CA (US)

(72) Inventor: Christine Wurth, Loerrach (DE)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 15/787,265

(22) Filed: Oct. 18, 2017

(65) Prior Publication Data

US 2018/0280514 A1    Oct. 4, 2018

Related U.S. Application Data

(62) Division of application No. 14/207,885, filed on Mar. 13, 2014, now Pat. No. 10,010,611.

(60) Provisional application No. 61/780,899, filed on Mar. 13, 2013.

(51) Int. Cl.
*A61K 39/395* (2006.01)
*A61K 47/26* (2006.01)
*A61K 9/08* (2006.01)
*C07K 16/22* (2006.01)
*C07K 16/28* (2006.01)

(52) U.S. Cl.
CPC ............... *A61K 47/26* (2013.01); *A61K 9/08* (2013.01); *A61K 39/39591* (2013.01); *C07K 16/22* (2013.01); *C07K 16/2887* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,419,446 A | 12/1983 | Howley et al. |
| 4,491,446 A | 1/1985 | Ewald |
| 4,560,655 A | 12/1985 | Baker |
| 4,601,978 A | 6/1986 | Karin |
| 4,657,866 A | 4/1987 | Kumar |
| 4,675,187 A | 6/1987 | Konishi et al. |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 4,965,199 A | 10/1990 | Capon et al. |
| 5,122,469 A | 6/1992 | Mather et al. |
| 5,500,362 A | 3/1996 | Robinson et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,894 A | 11/1996 | Wels et al. |
| 5,587,458 A | 12/1996 | King et al. |
| 5,591,828 A | 1/1997 | Bosslet et al. |
| 5,625,126 A | 4/1997 | Lonberg et al. |
| 5,631,144 A | 5/1997 | Lemoine et al. |
| 5,633,425 A | 5/1997 | Lonberg et al. |
| 5,641,870 A | 6/1997 | Rinderknecht et al. |
| 5,648,237 A | 6/1997 | Carter |
| 5,661,016 A | 8/1997 | Lonberg et al. |
| 5,736,137 A | 4/1998 | Anderson et al. |
| 5,789,199 A | 8/1998 | Joly et al. |
| 5,840,523 A | 11/1998 | Simmons et al. |
| 5,869,046 A | 2/1999 | Presta et al. |
| 5,959,177 A | 9/1999 | Hein et al. |
| 6,040,498 A | 3/2000 | Stomp et al. |
| 6,054,297 A | 4/2000 | Carter et al. |
| 6,075,181 A | 6/2000 | Kucherlapati et al. |
| 6,150,584 A | 11/2000 | Kucherlapati et al. |
| 6,235,764 B1 | 5/2001 | Larson et al. |
| 6,248,516 B1 | 6/2001 | Winter et al. |
| 6,267,958 B1 | 7/2001 | Andya et al. |
| 6,417,429 B1 | 7/2002 | Hein et al. |
| 6,420,548 B1 | 7/2002 | Vezina et al. |
| 6,534,524 B1 | 3/2003 | Kania et al. |
| 6,582,959 B2 | 6/2003 | Kim |
| 6,602,684 B1 | 8/2003 | Umaña et al. |
| 6,703,020 B1 | 3/2004 | Thorpe et al. |
| 6,884,879 B1 | 4/2005 | Baca et al. |
| 6,919,436 B2 | 7/2005 | Lihme et al. |
| 6,919,439 B2 | 7/2005 | Manoharan et al. |
| 6,982,321 B2 | 1/2006 | Winter |
| 7,060,269 B1 | 1/2006 | Baca et al. |
| 7,078,492 B2 | 7/2006 | Pirofski et al. |
| 7,087,409 B2 | 8/2006 | Barbas, III et al. |
| 7,087,492 B2 | 8/2006 | Popp et al. |

(Continued)

FOREIGN PATENT DOCUMENTS

| CN | 101678103 A | 3/2010 |
|---|---|---|
| CN | 102770158 A | 11/2012 |

(Continued)

OTHER PUBLICATIONS

Anderson et al. "Expression of Human B Cell-Associated Antigens on Leukemias and Lymphomas: A Model of Human B Cell Differentiation," *Blood* 63(6):1424-1433, (Jun. 1984).

Barbas et al. "Assembly of Combinatorial Antibody Libraries on Phage Surfaces: The Gene III Site," *Proc. Natl. Acad. Sci. USA*, 88:7978-7982, (Sep. 1991).

Barbas "Semisynthetic Combinatorial Antibody Libraries: A Chemical Solution to the Diversity Problem," *Proc. Natl. Acad. Sci. USA*, 89:4457-4461, (May 1992).

Barnes et al. "Methods for Growth of Cultured Cells in Serum-Free Medium," *Anal. Biochem.* 102:255-270, (1980).

Bass et al. "Hormone Phage: An Enrichment Method for Variant Proteins with Altered Binding Properties," *Proteins*, 8: 309-314 (1990).

(Continued)

*Primary Examiner* — Yunsoo Kim
(74) *Attorney, Agent, or Firm* — Morrison & Foerster LLP

(57) ABSTRACT

The invention provides stable aqueous pharmaceutical formulations comprising a therapeutic antibody, trehalose, a buffer, and optional surfactant, and having a pH in the range of about 5.5 to about 7.0. The invention also provides methods for making such formulations and methods of using such formulations.

35 Claims, 8 Drawing Sheets
Specification includes a Sequence Listing.

(56) References Cited

U.S. PATENT DOCUMENTS

| | | | |
|---|---|---|---|
| 7,125,978 | B1 | 10/2006 | Vézina et al. |
| 7,153,507 | B2 | 12/2006 | van de Winkel et al. |
| 7,189,826 | B2 | 3/2007 | Rodman |
| 7,910,098 | B2 | 3/2011 | Fuh et al. |
| 10,010,611 | B2 | 7/2018 | Gokarn et al. |
| 2003/0190317 | A1 | 10/2003 | Baca et al. |
| 2003/0203409 | A1 | 10/2003 | Kim et al. |
| 2003/0206899 | A1 | 11/2003 | Ferrara et al. |
| 2005/0026229 | A1 | 2/2005 | Reiter et al. |
| 2005/0100546 | A1 | 5/2005 | Jakobovits et al. |
| 2005/0112126 | A1 | 5/2005 | Baca et al. |
| 2005/0176122 | A1 | 8/2005 | Lihme et al. |
| 2005/0186208 | A1 | 8/2005 | Fyfe et al. |
| 2005/0260186 | A1 | 11/2005 | Bookbinder et al. |
| 2005/0287149 | A1 | 12/2005 | Keler et al. |
| 2006/0009360 | A1 | 1/2006 | Pifer et al. |
| 2006/0059575 | A1 | 3/2006 | Kusunoki et al. |
| 2006/0088523 | A1* | 4/2006 | Andya ............ A61K 39/39541 424/133.1 |
| 2006/0104968 | A1 | 5/2006 | Bookbinder et al. |
| 2006/0183887 | A1 | 8/2006 | Jakobovits et al. |
| 2006/0258841 | A1 | 11/2006 | Michl et al. |
| 2006/0280747 | A1 | 12/2006 | Fuh et al. |
| 2007/0020267 | A1 | 1/2007 | Fuh et al. |
| 2007/0141065 | A1 | 6/2007 | Fuh et al. |
| 2007/0224203 | A1 | 9/2007 | Friess et al. |
| 2009/0162352 | A1* | 6/2009 | Adler ................ A61K 9/0019 424/133.1 |
| 2011/0171217 | A1 | 7/2011 | Badkar et al. |
| 2011/0226650 | A1 | 9/2011 | Gokarn et al. |
| 2011/0237506 | A1 | 9/2011 | Garigapati et al. |
| 2014/0072559 | A1 | 3/2014 | Soula |
| 2014/0127227 | A1 | 5/2014 | Chang |
| 2014/0314748 | A1 | 10/2014 | Gokarn et al. |
| 2016/0137727 | A1 | 5/2016 | Le et al. |
| 2019/0161541 | A1 | 5/2019 | Le et al. |
| 2020/0179516 | A1 | 6/2020 | Gokarn |

FOREIGN PATENT DOCUMENTS

| | | |
|---|---|---|
| CN | 102573789 B | 9/2015 |
| DE | 266710 A3 | 4/1989 |
| EP | 0 073 657 A1 | 3/1983 |
| EP | 0 073 657 B1 | 3/1983 |
| EP | 0 183070 A2 | 6/1986 |
| EP | 0 183070 A3 | 6/1986 |
| EP | 0 183070 B1 | 6/1986 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| EP | 0 308 936 A2 | 3/1989 |
| EP | 0 404 097 A2 | 12/1990 |
| EP | 0 404 097 A3 | 12/1990 |
| EP | 0 404 097 B1 | 12/1990 |
| EP | 0 402226 A1 | 12/1990 |
| EP | 0 666 868 B1 | 8/1995 |
| JP | 2011500741 A | 1/2011 |
| JP | 2012-519712 A | 8/2012 |
| JP | 2013-521311 A | 6/2013 |
| RU | 2426554 C2 | 8/2011 |
| WO | WO-1987/00195 A1 | 1/1987 |
| WO | WO 1989/06692 A1 | 7/1989 |
| WO | WO-1990/03430 A1 | 4/1990 |
| WO | WO-1990/13646 A1 | 11/1990 |
| WO | WO-1991/00360 A1 | 1/1991 |
| WO | WO-1991/10741 A1 | 7/1991 |
| WO | WO-1992/09690 A2 | 6/1992 |
| WO | WO-1992/09690 A3 | 6/1992 |
| WO | WO-1992/20373 A1 | 11/1992 |
| WO | WO-1993/01161 A1 | 1/1993 |
| WO | WO-1993/06213 A1 | 4/1993 |
| WO | WO-1993/08829 A1 | 5/1993 |
| WO | WO-1993/11161 A1 | 6/1993 |
| WO | WO-1993/16185 A2 | 8/1993 |
| WO | WO-1993/16185 A3 | 8/1993 |
| WO | WO-1994/04690 A1 | 3/1994 |
| WO | WO-1994/10202 A1 | 5/1994 |
| WO | WO-1994/11026 A2 | 5/1994 |
| WO | WO-1994/11026 A3 | 5/1994 |
| WO | WO-1995/27062 A1 | 10/1995 |
| WO | WO-1996/07754 A1 | 3/1996 |
| WO | WO-1996/27011 A1 | 9/1996 |
| WO | WO-1996/30046 A1 | 10/1996 |
| WO | WO-1996/33735 A1 | 10/1996 |
| WO | WO-1996/34096 A1 | 10/1996 |
| WO | WO-1998/24893 A2 | 6/1998 |
| WO | WO-1998/24893 A3 | 6/1998 |
| WO | WO-1998/45332 A2 | 10/1998 |
| WO | WO-1998/45332 A3 | 10/1998 |
| WO | WO-1999/054342 A1 | 10/1999 |
| WO | WO-2004/035607 A2 | 4/2004 |
| WO | WO-2004/035607 A3 | 4/2004 |
| WO | WO-2004/056312 A2 | 7/2004 |
| WO | WO-2004/056312 A3 | 7/2004 |
| WO | WO-2004/065540 A2 | 8/2004 |
| WO | WO-2004/065540 A3 | 8/2004 |
| WO | WO-2004/113304 A1 | 12/2004 |
| WO | WO-2005/012359 A2 | 2/2005 |
| WO | WO-2005/012359 A3 | 2/2005 |
| WO | WO-2005/044859 A2 | 5/2005 |
| WO | WO-2005/044859 A3 | 5/2005 |
| WO | WO 2005/103081 A2 | 11/2005 |
| WO | WO 2005/103081 A3 | 11/2005 |
| WO | WO-2006/044908 A2 | 4/2006 |
| WO | WO-2006/044908 A3 | 4/2006 |
| WO | WO-2007/031875 A2 | 3/2007 |
| WO | WO-2007/031875 A3 | 3/2007 |
| WO | WO-2008/121615 A2 | 9/2008 |
| WO | WO-2008/121615 A3 | 9/2008 |
| WO | WO2009053038 A2 | 4/2009 |
| WO | WO2009053038 A3 | 6/2009 |
| WO | WO-2009/105534 A2 | 8/2009 |
| WO | WO-2009/105534 A3 | 8/2009 |
| WO | WO-2010/102276 A2 | 9/2010 |
| WO | WO-2010/102276 A3 | 9/2010 |
| WO | WO-2011/012637 A2 | 2/2011 |
| WO | WO-2011/012637 A3 | 2/2011 |
| WO | WO-2011/012637 A4 | 2/2011 |
| WO | WO-2011/084750 A1 | 7/2011 |
| WO | WO-2011/109789 A2 | 9/2011 |
| WO | WO-2011/109789 A3 | 9/2011 |
| WO | WO-2012/135408 A1 | 10/2012 |
| WO | WO-2012/146934 A1 | 11/2012 |
| WO | WO-2013/063510 A1 | 5/2013 |
| WO | WO-2014/160490 A1 | 10/2014 |
| WO | WO-2016/044334 A1 | 3/2016 |

OTHER PUBLICATIONS

Boerner et al. "Production of Antigen-Specific Human Monoclonal Antibodies from in vitro-Primed Human Splenocytes," *J. Immunol.*, 147(1):86-95, (Jul. 1, 1991).

Brennan et al. "Preparation of Bispecific Antibodies by Chemical Recombination of Monoclonal Immunoglobulin $G_1$ Fragments," *Science*, 229:81-83, (Jul. 5, 1985).

Brodeur et al. "Mouse-Human Myeloma Partners for the Production of Heterohybridomas," *Monoclonal Antibody Production Techniques and Applications* (Marcel Dekker, Inc., New York, 1987), pp. 51-63.

Bruggemann et al. "Designer Mice: The Production of Human Antibody Repertoires in Transgenic Animals," *Year in Immunol.* 7:33-40, (1993).

Carmeliet et al. "Abnormal Blood Vessel Development and Lethality in Embryos Lacking a Single VEGF Allele," *Nature* 380:435-439 (Apr. 4, 1996).

Carter et al. "Humanization of an Anti-p185$^{HER2}$ Antibody for Human Cancer Therapy," *Proc. Natl. Acad. Sci. USA*, 89:4285, (1992).

Carter. Et al. "High Level *Escherichia Coli* Expression and Production of a Bivalent Humanized Antibody Fragment," *Bio/Technology* 10:163-167 (Feb. 1992).

(56) References Cited

OTHER PUBLICATIONS

Cavatur, R.K. et al. "Crystallization Behavior of Mannitol in Frozen Aqueous Solutions," *Pharm. Res.* 19(6):894-900, (Jun. 2002).
Cebe-Suarez et al. "The Role of VEGF Receptors in Angiogenesis; Complex Partnerships," *Cell. Mol. Life Sci.* 63:601-615, (2006).
Champe et al. "Monoclonal Antibodies that Block the Activity of Leukocyte Function-Associated Antigen 1 Recognize Three Discrete Epitopes in the Inserted Domain of CD11a," *J. Biol. Chem.* 270(3):1388-1394, (Jan. 20, 1995).
Charlton "Expression and Isolation of Recombinant Antibody Fragments in *Escherichia coli*," *Methods in Molecular Biology*, vol. 248:Antibody Enaineering: Methods and Protocols (B.K.C. Lo © Humana Press Inc. (2003), pp. 245-254.
Chothia et al. "Canonical Structures for the Hypervariable Regions of Immunoglobulins," *J. Mol. Biol.* 196:901-917 (1987).
Clackson et al. "Making Antibody Fragments Using Phage Display Libraries," *Nature*, 352:624-628, (Aug. 15, 1991).
Cleland et al. "The Development of Stable Protein Formulations: A Close Look at Protein Aggregation, Deamidation, and Oxidation," *Critical Reviews in Therapeutic Drug Carrier Systems* 10(4): 307-377, (1993).
Cole et al. "The EBV-Hybridoma Technique and its Application to Human Lung Cancer," *Monoclonal Antibodies and Cancer Therapy* (Alan R. Liss, Inc. New York 1985), pp. 77-96.
Connolly, B. et al. "Vibrational Spectroscopy and Chemometrics to Characterize and Quantitate Trehalose Crystallization," *Anal. Biochem.* 399(1):48-57, (2010. e-pub. Oct. 22, 2009).
Cragg et al. "Complement-Mediated Lysis by Anti-CD20 mAb Correlates with Segregation into Lipid Rafts," *Blood* 101:1045-1052, (Feb. 1, 2003, e-pub. Sep. 19, 2002).
Cragg et al. "Antibody Specificity Controls in vivo Effector Mechanisms of Anti-CD20 Reagents," *Blood* 103:2738-2743, (Apr. 1, 2004, e-pub. Oct. 9, 2003).
Cumming et al. "Glycosylation of Recombinant Protein Therapeutics: Control and Functional Implications," *Glycobiology* 1(2):115-130, (1991).
Duchosal et al. "Immunization of hu-PBL-SCID Mice and the Rescue of Human Monoclonal Fab Fragments Through Combinational Libraries," *Nature* 355:258-262, (Jan. 16, 1992).
Eckhardt, B.M. et al. "Effect of Freezing on Aggregation of Human Growth Hormone," *Pharm. Res.* 8(11):1360-1364. (1991).
Einfeld et al. "Molecular Cloning of the Human B Cell CD20 Receptor Predicts a Hydrophobic Protein with Multiple Transmembrane Domains," *EMBO J.* 7(3) 711-717, (1988).
Embleton et al. "In-Cell PCR from Mrna: Amplifying and Linking the Rearranged Immunoglobulin Heavy and Light Chain V-Genes Within Single Cells," *Nucl. Acids Res.*, 20(15):3831-3837, (1992).
Even et al. "Serum-Free Hybridoma Culture: Ethical, Scientific and Safety Considerations," *Trends in Biotechnology*, 24(3):105-108, (Mar. 2006, e-pub. Jan. 19, 2006).
Fellouse "Synthetic Antibodies from a Four-Amino-Acid Code: A Dominant Role for Tyrosine in Antigen Recognition," *Proc. Natl. Acad. Sci. USA* 101(34):12467-12472, (Aug. 24, 2004).
Ferrara et al. "Heterozygous Embryonic Lethality Induced by Targeted Inactivation of the VEGF Gene," *Nature* 380:439-442, (Apr. 4, 1996).
Ferrara et al. "The Biology of Vascular Endothelial Growth Factor," *Endocrine Rev.* 18(1):4-25, (Feb. 1997).
Ferrara et al. "Vascular Endothelial Growth Factor is Essential for Corpus Luteum Angiogenesis," *Nature Med.* 4(3):336-340, (Mar. 1998).
Ferrara et al. "Molecular and Biological Properties of Vascular Endothelial Growth Factor," *J. Mol. Med.* 77:527-543 (1999).
Ferrara et al. "Clinical Applications of Angiogenic Growth Factors and Their Inhibitors," *Nature Medicine* 5(12):1359-1364, (Dec. 1999).
Ferrara, N. et al. "Bevacizumab (Avastin), A Humanized Anti-VEGF Monoclonal Antibody for Cancer Therapy," *Biophys. Res. Commun.* 333(2):328-335, (2005, e-pub. Jun. 2, 2005).

Fishwild et al. "High-Avidity Human IgGκ Monoclonal Antibodies from a Novel Strain of Minilocus Transgenic Mice," *Nature Biotechnol.* 14:845-851, (Jul. 1996).
Fleer et al. "Stable Multicopy Vectors for High-Level Secretion of Recombinant Human Serum Albumin by *Kluyveromyces* Yeasts," *Bio/Technology*, 9:968-975, (Oct. 1991).
Franek "Oligopeptides as Tools for Improving Productivity of Hybridoma Cells Cultures,"*Trends in Monoclonal Antibody Research* pp. 111-122, (2005).
GENBANK Accession No. NP-690605, last updated May 3, 2014, located at http://www.ncbi.nlm.nih.gove/protein/NP_690605, last visited Mar. 5, 2015, two pages.
Gerber et al. "VEGF Couples Hypertrophic Cartilage Remodeling, Ossification and Angiogenesis During Endochondral Bone Formation," *Nature Med.* 5(6):623-628, (Jun. 1999).
Gerngross "Advances in the Production of Human Therapeutic Proteins in Yeasts and Filamentous Fungi," *Nat. Biotech.* 22(11):1409-1414, (Nov. 2004, e-pub. Nov. 4, 2004).
Goding "Production and Application of Monoclonal Antibodies in Cell Biology, Biochemistry and Immunology," *Monoclonal Antibodies: Principles and Practice* (Academic Press 1983), pp. 59-103.
Graham et al. "Characteristics of Human Cell Line Transformed by DNA from Human Adenovirus Type 5," *J. Gen Virol.* 36:59-72, (1977).
Gram et al. "In Vitro Selection and Affinity Maturation of Antibodies from a Naïve Combinatorial Immunoglobulin Library," *Proc. Natl. Acad. Sci. USA*, 89:3576-3580, (Apr. 1992).
Griffiths et al. "Human Anti-Self Antibodies with High Specificity from Phage Display Libraries," *EMBO.* 12(2):725-734, (1993).
Gruber et al. "Efficient Tumor Cell Lysis Mediated by a Bispecific Single Chain Antibody Expressed in *Escherichia coli*," *J. Immuno.* 152:5368-5374, (1994).
Guerrin et al. "Vasculotropin/Vascular Endothelial Growth Factor is an Autocrine Growth Factor for Human Retinal Pigment Epithelial Cells Cultured in vitro," *J. Cell Physiol.* 164:385-394, (1995).
Guss et al. "Structure of the IgG-Binding Regions of Streptococcal Protein G," *EMBO J.* 5(7):1567-1575, (1986).
Ham et al. "Basic Methods: Media and Growth Requirements," *Meth. Enz.* 58:44-93, (1979).
Hamers-Casterman et al. "Naturally Occurring Antibodies Devoid of Light Chains," *Nature* 363:446-448, (Jun. 3, 1993).
Hammerling et al. "Production of Hybridomas in the Rodent System," *Monoclonal Antibodies and T-Cell Hybridomas*, (Elsevier/North Holland Biomedical Press. Amsterdam 1981), pp. 563-681.
Harlow et al. *Antibodies: A Laboratory Manual*, (Cold Spring Harbor Laboratory Press, 2nd ed. (1988), 89 pages.
Harris "Therapeutic Monoclonals: Production of Humanized Monoclonal Antibodies for in vivo Imaging and Therapy," *Biochem. Soc. Transactions* 23:1035-1038, (1995).
Hawkins et al. "Selection of Phage Antibodies by Binding Affinity: Mimicking Affinity Maturation," *J. Mol. Biol.* 226:889-896, (1992).
Hogrefe et al. "A Bacteriophage Lambda Vector for the Cloning and Expression of Immunoglobulin Fab Fragments on the Surface of Filamentous Phage," *Gene* 128:119-126, (1993).
Holliger et al. "'Diabodies': Small Bivalent and Bispecific Antibody Fragments," *Proc. Natl. Acad. Sci. USA* 90:6444-6448, (Jul. 1993).
Hongo S. et al. "Development and Characterization of Murine Monoclonal Antibodies to the Latency-Associated Peptide of Transforming Growth Factor $\beta_1$," *Hybridoma* 14(3):253-260, (1995).
Hoogenboom et al. "Multi-Subunit Proteins on the Surface of Filamentous Phage: Methodologies for Displaying Antibody (Fab) Heavy and Light Chains," *Nucl. Acids Res.* 19(15):4133-4137, (1991).
Hoogenboom et al. "By-Passing Immunisation: Human Antibodies from Synthetic Repertoires of Germline $V_H$ Gene Segments Rearranged in Vitro," *J. Mol. Biol.* 227:381-388, (1992).
Hoogenboom et al. "Overview of Antibody Phage-Display Technology and its Applications," *Methods in Molecular Biology* vol. 178:Antibody Phage Display: Methods and Protocols, (P.M. O'Brien and R. Altken © Humana Press Inc., Totowa, N.J. 2001), pp. 1-37.
Houck et al. "The Vascular Endothelial Growth Factor Family: Identification of a Fourth Molecular Species and Characterization of Alternative Splicing of RNA," *Mol. Endocrin.* 5:1806-1814, (1991).

(56) References Cited

OTHER PUBLICATIONS

Hudson et al. "Engineered Antibodies," *Nat. Med.* 9(1):129-134, (Jan. 2003).
Hurle et al. "Protein Engineering Techniques for Antibody Humanization," *Curr. Op. Biotech.* 5:428-433, (1994).
Inn, WHO Drug Information, 25(1):75-76, (2011).
Inn, WHO Drug Information, 22(2):124, (2008).
Inn, WHO Drug Information, 23(2):176, (2009).
Inn, WHO Drug Information, 26(4):453, (2012).
Izutsu, K.-I. et al. "Decreased Protein-Stabilizing Effects of Cryoprotectants Due to Crystallization," *Pharm. Res.* 10(8):1232-1237, (Aug. 1993).
Izutsu, K.-I. et al. "Effect of Mannitol Crystallinity on the Stabilization of Enzymes During Freeze-Drying," *Chem. Pharm. Bull.* 42(1):5-8, (Jan. 1994).
Jakobovits et al. "Germ-Line Transmission and Expression of a Human-Derived Yeast Artifical Chromosome," *Nature* 362:255-258, (Mar. 18, 1993).
Jakobovits et al. "Analysis of Homozygous Mutant Chimeric Mice: Deletion of the Immunoglobulin Heavy-Chain Joining Region Blocks B-Cell Development and Antibody Production," *Proc. Natl. Acad. Sci. USA* 90:2551, (Mar. 1993).
Jefferis et al. "IgG-Fc-Mediated Effector Functions: Molecular Definition of Interaction Sites for Effector Ligands and the Role of Glycosylation," *Immunol. Rev.* 163:59-76, (1998).
Jenkins et al. "Getting the Glycosylation Right: Implications for the Biotechnology Industry," *Nature Biotechnol.* 14:975-981, (Aug. 1996).
Johnson et al. "The Kabat Database and a Bioinformatics Example" *Methods in Molecular Biology* 248:11-25, (2003).
Jones "Proteinase Mutants of *Saccharomyces cerevisiae*," *Genetics*, 85:23-33, (Jan. 1977).
Jones et al. "Replacing the Complementarity-Determining Regions in a Human Antibody with Those from a Mouse," *Nature* 321:522-525, (May 29, 1986).
Jones et al. "Rapid PCR-Cloning of Full-Length Muse Immunoglobulin Variable Regions," *Biotechnol.* 9:88-89, (Jan. 1991).
Jones "Analysis of Polypeptides and Proteins," A. *Adv. Drug Delivery Rev.* 10:29-90, (1993).
Klagsbrun et al. "Regulators of Angiogenesis," *Annu. Rev. Physiol.* 53:217-239, (1991).
Kohler et al. "Continuous Cultures of Fused Cells Secreting Antibody of Predefined Specificity," *Nature*, 256:495-97, (Aug. 7, 1975).
Komaromy et al. (Oct. 11, 1983). "The Structure of the Mouse Immunoglobulin in $\gamma_3$ Membrane Gene Segment," *Nucl. Acid Res.* 11(19):6775-6785.
Kostelny et al. "Formation of a Bispecific Antibody by the Use of Leucine Zippers," *J. Immunol.*, 148(5):1547-1553, (Mar. 1, 1992).
Kozbor "A Human Hybrid Myeloma for Production of Human Monoclonal Antibodies," *J. Immunol.*, 133(6):3001-3005, (Dec. 1984).
Lee et al. "High-Affinity Human Antibodies from Phage-Displayed Synthetic Fab Libraries with a Single Framework Scaffold," *J. Mol. Biol.* 340(5):1073-1093, (2004).
Lee et al. "Bivalent Antibody Phage Display Mimics Natural Immunoglobulin," *J. Immunol. Methods* 284(1-2):119-132, (2004).
Leung et al. "Vascular Endothelial Growth Factor is a Secreted Angiogenic Mitogen," *Science* 246:1306-1309, (Dec. 8, 1989).
Leung et al. "A Method for Random Mutagenesis of a Defined DNA Segment Using a Modified Polymerase Chain Reaction," *Technique* 1(1):11-15 (Aug. 1989).
Li et al. "Optimization of Humanized IgGs in Glycoengineered *Pichi pastories*," *Nat. Biotech.* 24(2):210-215, (Feb. 2006, e-pub. Jan. 22, 2006).
Li et al. "Human Antibodies for Immunotherapy Development Generated via a Human B Cell Hybridoma Technology," *Proc. Natl. Acad. Sci. USA*, 103(10):3557-3562, (Mar. 7, 2006).
Liang et al. "Cross-Species Vascular Endothelial Growth Factor (VEGF) Blocking Antibodies Completely Inhibit the Growth of Human Tumor Xenografts and Measure the Contribution of Stromal VEGF," *J Biol Chem* 281(2):951-961, (Jan. 13, 2006).
Lifely et al. "Glycosylation and Biological Activity of CAMPATH-1H Expressed in Different Cell Lines and Grown Under Different Culture Conditions," *Glycobiology* 5(8):813-822, (1995).
Lindmark et al. "Binding of Immunoglobulins to Protein A and Immunoglobulin Levels in Mammalian Sera," *J. Immunol. Meth.* 62:1-13, (1983).
Lonberg et al. "Antigen-Specific Human Antibodies from Mice Comprising Four Distinct Genetic Modifications," *Nature* 368:856-859, (Apr. 28, 1994).
Lonberg et al. "Human Antibodies from Transgenic Mice," *Intern. Rev. Immunol.* 13:65-93, (1995).
Marks et al. "By-Passing Immunization: Human Antibodies from V-Gene Libraries Displayed on Phage," *J. Mol. Biol.* 222:581-597, (1991).
Marks et al. "By-Passing Immunization: Building High Affinity Human Antibodies by Chain Shuffling," *Bio/Technology* 10:779-783, (Jul. 1992).
Mather "Establishment and Characterization of Two Distinct Mouse Testicular Epithelial Cell Lines," *Biol. Reprod.* 23:243-251, (1980).
Mather et al. "Culture of Testicular Cell in Hormone-Supplemented Serum-Free Medium," *Annals N.Y. Acad. Sci.* 383:44-68, (1982).
Matsuda et al. "Structure and Physical Map of 64 Variable Segments in the 3' 0.8-Megabase Region of the Human Immunoglobulin Heavy-Chain Locus," *Nature Genet.* 3(1):88-94, (Jan. 1993).
Miller, D.P. et al. "Thermophysical Properties of Trehalose and its Concentrated Aqueous Solutions," *Pharm. Res.* 14(5):578-590, (1997).
Milstein et al. "Hybrid Hybridomas and Their Use in Immunohistochemistry," *Nature* 305:537-539, (1983).
Morimoto et al. "Single-Step Purification of F(ab')$_2$ Fragments of Mouse Monoclonal Antibodies (Immunoglobulins G1) by Hydrophobic Interaction High Performance Liquid Chromatography Using TSKgel Phenyl-5PW," *Journal of Biochemical and Biophysical Methods* 24:107-117, (1992).
Morrison et al. "Chimeric Human Antibody Molecules: Mouse Antigen-Binding Domains with Human Constant Region Domains," *Proc. Natl. Acad. Sci. USA* 81:6851-6855, (Nov. 1984).
Morrison. "Success in Specification," *Nature* 368:812-813, (Apr. 28, 1994).
Munson et al. "LIGAND: A Versatile Computerized Approach for Characterization of Ligand-Binding Systems," *Anal. Biochem.* 107:220-239, (1980).
Murakami et al. "Cell Cycle Regulation, Oncogenes, and Antineoplastic Drugs," in *The Molecular Basis of Cancer, Chapter 1* (W.B. Saunders Company, Philadelphia, 1995), pp. 3-17.
Neuberger "Generating High-Avidity Human Mabs in Mice," *Nature Biotechnol.* 14:826, (Jul. 1996).
Ni "Research Progress and Future Perspectives in Antibodomics and Antibodomic Drugs," *Xiandai Mianyixue* 26(4):265-268, (Oct. 23, 2006).
Nicolaou et al. "Calicheamicin $\theta^I_1$: A Rationally Designed Molecule with Extremely Potent and Selective DNA Cleaving Properties and Apoptosis Inducing Activity," *Angew. Chem Intl. Ed. Engl.* 33(2):183-186, (1994).
Oberg-Welsh et al. "Effects of Vascular Endothelial Growth Factor on Pancreatic Duct Cell Replication and the Insulin Production of Fetal Islet-Like Cell Clusters in vitro," *Mol. Cell. Endocrinol.* 126:125-132, (1997).
Orlandi et al. "Cloning Immunoglobulin Variable Domains for Expression by the Polymerase Chain Reaction," *Proc. Natl. Acad. Sci. USA* 86:3833-3837, (May 1989).
Orum et al. "Efficient Method for Constructing Comprehensive Murine Fab Antibody Libraries Displayed on Phage," *Nucleic Acids Res.* 21(19):4491-4498, (1993).
Pearlman et al. "Analysis of Protein Drugs," Chapter 6 in *Peptide and Protein Drug Delivery*, (Lee, V.H.L., Marcel Dekker, Inc., New York, New York, 1991), pp. 247-297.
Pluckthun "Mono- and Bivalent Antibody Fragments Produced in *Escherichia coli*: Engineering, Folding and Antigen Binding," *Immunol. Revs.* 130:151-188, (1992).

(56) References Cited

OTHER PUBLICATIONS

Pluckthün "Antibodies from *Escherichia coli,*" *The Pharmacology of Monoclonal Antibodies,* vol. 113, Rosenburg and Moore eds., (Springer-Verlag, New York, 1994), pp. 269-315.
Popkov et al. "Human/Mouse Cross-Reactive Anti-VEGF Receptor 2 Recombinant Antibodies Selected from an Immune b9 Allotype Rabbit Antibody Library," *Journal of Immunological Methods* 288:149-164, (2004).
Poppema et al. "Preparation and Application of Monoclonal Antibodies: B Cell Panel and Paraffin Tissue Reactive Panel," *Biotest Bulletin* 3:131-139, (1987).
Presta "Antibody Engineering," *Curr. Op. Struct. Biol.* 2:593-596, (1992).
Presta et al. "Humanization of an Antibody Directed Against IgE," *J. Immunol.* 151(5):2623-2632, (Sep. 1, 1993).
Presta et al. "Humanization of an Anti-Vascular Endothelial Growth Factor Monoclonal Antibody for the Therapy of Solid Tumors and Other Disorders," *Cancer Res.* 57:4593-4599, (Oct. 15, 1997).
Reff et. Al. "Depletion of B Cells in vivo by a Chimeric Mouse Human Monoclonal Antibody to CD20," *Blood* 83(2):435-445, (Jan. 15, 1994).
Reyes et al. "Expression of Human β-Interferon cDNA Under the Control of a Thymidine Kinase Prompter from Herpes Simplex Virus," *Nature* 297:598-601, (Jun. 17, 1982).
Riechmann et al. "Reshaping Human Antibodies for Therapy," *Nature* 332:323-329, (Mar. 24, 1988).
Sastry et al. "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86:5728-5732, (Aug. 1989).
Saito, S. et al. (2013, e-pub. Jan. 15, 2013). "Effects of Ionic Strength and Sugars on the Aggregation Propensity of Monoclonal Antibodies: Influence of Colloidal and Conformational Stabilities," *Pharm. Res.* 30:1263-1280.
Sato "Molecular Diagnosis of Tumor Angiogenesis and Anti-Angiogenic Cancer Therapy," *Int. J. Clin. Oncol.* 8:200-206, (2003).
Schüle, S. et al. (Aug. 2008, e-pub. Feb. 19, 2008). "Stabilization of IgG1 in Spray-Dried Powders for Inhalation," *Eur. J. Pharm. Biopharm.* 69(3):793-807.
Sehn, L.H. et al. (May 31, 2012, e-pub. Mar. 20, 2012) "A Phase 1 Study of Obinutuzumab Induction Followed by 2 Years of Maintenance in Patients with Relapsed CD20-Positive B-Cell Malignancies," *Blood* 119(22):5118-5125.
Shalaby, M.R. et al. "Development of Humanized Bispecifc Antibodies Reactive with Cytotoxic Lymphocytes and Tumor Cells Overexpressing the HER2 Protooncogene," *J. Exp. Med.* 175:217-225, (Jan. 1, 1992).
Sharma, V.K. et al. "Effect of Vacuum Drying on Protein-Mannitol Interactions: The Physical State of Mannitol and Protein Structure in the Dried State," *AAPS PharmSciTech.* 5(1):E10, (2004).
Sheriff et al. "Redefining the Minimal Antigen-Binding Fragment," *Nature Struct. Biol.* 3(9):733-736, (Sep. 1996).
Sidhu et al. "Phage-Displayed Antibody Libraries of Synthetic heavy Chain Complementarity Determining Regions," *J. Mol. Biol.* 338(2):299-310, (2004).
Sims et al. "A Humanized CD18 Antibody Can Block Function Without Cell Destruction," *J. Immunol.* 151(4):2296-2308, (Aug. 15, 1993).
Skerra et al. "Bacterial Expression of Immunoglobulin Fragments," *Curr. Opinion in Immunol.* 5:256-262, (1993).
Sondell et al. "Vascular Endothelial Growth Factor has Neutrotrophic Activity and Stimulates Axonal Outgrowth, Enhancing Cell Survival and Schwann Cell Proliferation in the Peripheral Nervous System," *J. Neurosci.* 19(14):5731-5740, (Jul. 15, 1999).
Stamenkovic. Et al. "Analysis of Two cDNA Clones Encoding the B Lymphocyte Antigen CD20 (B1, Bp35), a Type III Intergral Membrane Protein," *J. Exp. Med.* 167:1975-1980, (Jun. 1988).
Stinchcomb et al. "Isolation and Characterisation of a Yeast Chromosomal Replicator," *Nature* 282:39-43, (Nov. 1, 1979).

Streit et al. "Angiogenesis, Lymphangiogenesis, and Melanoma Metastasis," *Oncogene* 22:3172-3179, (2003).
Suresh et al. "Bispecific Monoclonal Antibodies from Hybrid Hybridomas," *Methods in Enzymology*, 121:210-228, (1986).
Tedder et al. "The B Cell Surface Molecule B1 is Functionally Linked with B Cell Activation and Differentiation," *J. Immunol.* 135(2):973-979, (Aug. 1985).
Tedder et al. "Antibodies Reactive with the B1 Molecule Inhibit Cell Cycle Progression but Not Activation of Human B Lymphocytes," *Eur. J. Immunol.* 16(8):881-887, (1986).
Tedder et al. "Isolation and Structure of a cDNA Encoding the B1 (CD20) Cell-Surface Antigen of Human B Lymphocytes," *Proc. Natl. Acad. Sci. U.S.A.* 85:208-212, (Jan. 1988).
Tedder et al. "Structure of the Gene Encoding the Human B Lymphocyte Differentiation Antigen CD20 (B1)[1]," *J. Immunol.* 142(7):2560-2568, (Apr. 1, 1989).
Tedder, T.F. et al. "Receptor-Modulated Transport System," *J. Cell Biochem.* 14D:195, (1990).
Tomlinson et al. "The Repertoire of Human Germline $V_H$ Sequences Reveals About Fifty Groups of $V_H$ Segments with Different Hypervariable Loops," *J. Mol. Biol.* 227:776-798, (1992).
Tonini et al. "Molecular Basis of Angiogenesis and Cancer," *Oncogene* 22:6549-6556, (2003).
Traunecker et al. "Bispecific Single Chain Molecules (Janusins) Target Cytotoxic Lymphocytes on HIV Infected Cells," *EMBO J.* 10(12):3655-3659, (1991).
Tutt et al. "Trispecific F(ab')$_3$ Derivatives That Use Cooperative Signaling Via the TEC/CD3 Complex and CD2 to Activate and Redirect Resting Cytotoxic T Cells," *J. Immunol.* 147(1):60-69, (Jul. 1, 1991).
Umana et al. "Engineered Glycoforms of an Antineuroblastoma IgG1 with Optimized Antibody-Dependent Cellular Cytotoxic Activity," *Nature Biotechnol.* 17:176-180,m (Feb. 1999).
Urlaub et al. "Isolation of Chinese Hamster Cell Mutants Deficient in Dihydrofolate Reductase Activity," *Proc. Natl. Acad. Sci. USA* 77:4216-4220, (Jul. 1980).
Valentine et al. "Phosphorylation of the CD20 Phosphoprotein in Resting B Lymphocytes," *J. Biol. Chem.* 264(19):11282-11287, (Jul. 5, 1989).
Van Den Berg "*Kluyveromyces* as a Host for Heterologous Eene Expression: Expression and Secretion of Prochymosin," *Bio/Technology*, 8:135-139, (Feb. 1990).
Van Dijk et al. "Human Antibodies as Next Generation Therapeutics," *Curr. Opin. Pharmacol.* 5:368-74, (2001).
Vaswani et al. "Humanized Antibodies as Potential Therapeutic Drugs," *Ann. Allergy, Asthma & Immunol.* 1:105-115, (Aug. 1998).
Verhoeyen et al. "Reshaping Human Antibodies: Grafting an Antilysozyme Activity," *Science,* 239:1534-1536, (1988).
Vollmers et al. "Death by Stress: Natural IgM-Induced Apoptosis," *Methods and Findings in Experimental and Clinical Pharmacology,* 27(3):185-191, (2005).
Vollmers et al. "The 'Early Birds': Natural IgM Antibodies and Immune Surveillance," *Histology and Histopathology* 20(3):927-937, (2005).
Wang, W. et al. "Antibody Structure, Instability, and Formulation," *J. of Pharmaceutical Sciences* 96(1):1-26 (Jan. 2007).
Ward et al. "Binding Activities of a Repertoire of Single Immunoglobulin Variable Domains Secreted from *Escherichia coli,*" *Nature*, 341:544-546, (Oct. 12, 1989).
Waterhouse et al. "Combinatiorial Infection and in vivo Recombination: A Strategy for Making large Phage Antibody Repertoires," *Nucl. Acids Res.* 21(9):2265-2266, (1993).
WHO Drug Information. (2008). Proposed Inn List 99 International Nonproprietary Names for Pharmaceutical Substances, World Health Organization, Geneva, Switzerland, 22(2):77-174.
WHO Drug Information. (2009). International Nonproprietary Names for Pharmaceutical Substances, World Health Organization, Geneva, Switzerland, 23(2):129-192.
WHO Drug Information. (2011). International Nonproprietary Names for Pharmaceutical Substances, World Health Organization, Geneva, Switzerland, 25(1):49-98.

(56) References Cited

OTHER PUBLICATIONS

WHO Drug Information. (2012). International Nonproprietary Names for Pharmaceutical Substances, World Health Organization, Geneva, Switzerland, 26(4):401-471.
Williams et al. "Cloning and Sequencing of Human Immunoglobulin $V_\lambda$ Gene Segments," *Eur. J. Immunol.* 23:1456-1461, (1993).
Winter et al. "Making Antibodies by Phage Display Technology," *Ann. Rev. Immunol.* 12:433-455, (1994).
Wright et al. "Effect of Glycosylation on Antibody Function: implications for Genetic Engineering," *Trends Biotech.* 15:26-32, (Jan. 1997).
Xu et al. "Diversity in the CDR3 Region of $V_H$ is Sufficient for Most Antibody Specificities," *Immunity* 13:37-45, (Jul. 2000).
Yaniv "Enhancing Elements for Activation of Eukaryotic Promoters," *Nature* 297:17-18, (May 6, 1982).
Yazaki et al. "Expression of Recombinant Antibodies in Mammalian Cell Lines " *Methods in Molecular Biology*, vol. 248 (B. K. C. Lo, ed., Humana Press, Totowa, N.J., 2003), pp. 255-268.
Zapata et al. "Engineering Linear F(ab')2 Fragments for Efficient Production in *Escherichia coli* and Enhanced Antiproliferative Activity," *Protein Eng.* 8(10):1057-1062, 1995).
Extended European Search Report dated Sep. 21, 2016, for EP Patent Application No. 14772646.7, filed on Jun. 14, 2014, 8 pages.
European Examination Report, Office Action, dated Apr. 8, 2019, for European Patent Application No. 15772124.2, 7 pages.
International Preliminary Report on Patentability or PCT Application No. PCT/US2015/050278, dated Mar. 21, 2017, filed Sep. 15, 2015, 13 pages.
International Search Report dated Jun. 27, 2014, for PCT Application No. PCT/US2014/026824, filed Mar. 13, 2014, five pages.
International Search Report dated Feb. 18, 2016, for PCT Application No. PCT/US2015/050278, filed on Sep. 15, 2016, 13 pages.
Invitation to Pay Additional Fees dated Dec. 3, 2015, for PCT Application No. PCT/US2015/050278, filed on Sep. 15, 2015, 9 pages.
Written Opinion, dated Jun. 27, 2014, for PCT Application No. PCT/US2014/026824, filed Mar. 13, 2014, 11 pages.
Written Opinion dated Feb. 18, 2016, for PCT Application No. PCT/US2015/050278, filed on Sep. 15, 2016, 12 pages.
Jain, N.K. et al. (Jan. 2009; E-pub Dec. 2, 2008) "Effect of Trehalose on Protein Structure," Protein Sci. 18(1):24-36.
U.S. Appl. No. 16/723,864, filed Dec. 20, 2019, Gokarn et al.(Copy not submitted herewith pursuant the waiver of 37 C.F.R. § 1.98(a)(2)(iii) issued by the Office on Sep. 21, 2004).

* cited by examiner

ANTIBODY FORMULATIONS

CROSS-REFERENCE TO RELATED APPLICATIONS

This application is a divisional of U.S. patent application Ser. No. 14/207,885, filed Mar. 13, 2014, which claims the benefit of U.S. Provisional Application No. 61/780,899, filed Mar. 13, 2013, the contents of each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392012401SEQLIST.txt, date recorded: Jun. 18, 2018 size: 27 KB).

FIELD OF THE INVENTION

This invention relates to stable aqueous pharmaceutical formulations comprising antibodies.

BACKGROUND OF THE INVENTION

In the past years, advances in biotechnology have made it possible to produce a variety of proteins for pharmaceutical applications using recombinant DNA techniques. Because proteins are larger and more complex than traditional organic and inorganic drugs (e.g., possessing multiple functional groups in addition to complex three-dimensional structures), the formulation of such proteins poses special problems. For a protein to remain biologically active, a formulation must preserve intact the conformational integrity of at least a core sequence of the protein's amino acids while at the same time protecting the protein's multiple functional groups from degradation. Degradation pathways for proteins can involve chemical instability (e.g., any process which involves modification of the protein by bond formation or cleavage resulting in a new chemical entity) or physical instability (e.g., changes in the higher order structure of the protein). Chemical instability can result from deamidation, racemization, hydrolysis, oxidation, beta elimination or disulfide exchange. Physical instability can result from denaturation, aggregation, precipitation or adsorption, for example. The three most common protein degradation pathways are protein aggregation, deamidation and oxidation. Cleland et al., *Critical Reviews in Therapeutic Drug Carrier Systems* 10(4): 307-377 (1993).

Included in the proteins used for pharmaceutical applications are antibodies. Stable aqueous formulations have been developed for pharmaceutical antibodies. See, e.g., WO 2011/084750. There is still a need in the art for a stable aqueous pharmaceutical formulation comprising an antibody, such as an anti-VEGF antibody and an anti-CD20 antibody, which mitigates formation of dimers, soluble aggregates, and particulates.

CD20 and Anti CD20 Antibodies

The CD20 molecule (also called human B-lymphocyte-restricted differentiation antigen or Bp35) is a hydrophobic transmembrane protein with a molecular weight of approximately 35 kD located on pre-B and mature B lymphocytes (Valentine, M. A., et al., *J. Biol. Chem.* 264(19) (1989) 11282-11287; and Einfield, D. A., et al. (1988) *EMBO J.* 7(3):711-717; Tedder, T. F., et al., *Proc. Natl. Acad. Sci. U.S.A.* 85 (1988) 208-12; Stamenkovic, I., et al., *J. Exp. Med.* 167 (1988) 1975-80; Tedder, T. F., et al., *J. Immunol.* 142 (1989) 2560-8). CD20 is found on the surface of greater than 90% of B cells from peripheral blood or lymphoid organs and is expressed during early pre-B cell development and remains until plasma cell differentiation. CD20 is present on both normal B cells as well as malignant B cells. In particular, CD20 is expressed on greater than 90% of B cell non-Hodgkin's lymphomas (NHL) (Anderson, K. C., et al., *Blood* 63(6) (1984) 1424-1433)) but is not found on hematopoietic stem cells, pro-B cells, normal plasma cells, or other normal tissues (Tedder, T. F., et al., *J. Immunol.* 135(2) (1985) 973-979).

The 85 amino acid carboxyl-terminal region of the CD20 protein is located within the cytoplasm. The length of this region contrasts with that of other B cell-specific surface structures such as IgM, IgD, and IgG heavy chains or histocompatibility antigens class I1 a or α chains, which have relatively short intracytoplasmic regions of 3, 3, 28, 15, and 16 amino acids, respectively (Komaromy, M., et al., *NAR* 11 (1983) 6775-6785). Of the last 61 carboxyl-terminal amino acids, 21 are acidic residues, whereas only 2 are basic, indicating that this region has a strong net negative charge. The GenBank Accession No. is NP-690605. It is thought that CD20 might be involved in regulating an early step(s) in the activation and differentiation process of B cells (Tedder, T. F., et al., *Eur. J. Immunol.* 16 (8) (1986) 881-887) and could function as a calcium ion channel (Tedder, T. F., et al., *J. Cell. Biochem.* 14D (1990) 195).

There exist two different types of anti-CD20 antibodies differing significantly in their mode of CD20 binding and biological activities (Cragg, M. S., et al., *Blood,* 103 (2004) 2738-2743; and Cragg, M. S., et al., *Blood,* 101 (2003) 1045-1052). Type I antibodies, as e.g. rituximab (a non-afocusylated, non-glycoengineered antibody with normal glycosylation pattern, also named "RTX"), are potent in complement mediated cytotoxicity, whereas type II antibodies, as e.g. Tositumomab (B1), 11B8, AT80 or humanized B-Ly1 antibodies, effectively initiate target cell death via caspase-independent apoptosis with concomitant phosphatidylserine exposure.

SUMMARY

In one aspect, the invention provides a stable aqueous pharmaceutical formulation, the formulation comprising a monoclonal antibody, trehalose and a buffer, wherein the weight ratio of the monoclonal antibody to the trehalose in the formulation is about 1.65 to about 4.95, and wherein the formulation has a pH of about 5.5 to about 7.0. In some embodiments, the weight ratio of the monoclonal antibody to the trehalose is about 1.65 to about 3.30. In some embodiments, the weight ratio of the monoclonal antibody to the trehalose is about 1.70 to about 2.91. In some embodiments, the weight ratio of the monoclonal antibody to the trehalose is about 2.00 to about 3.30. In some embodiments, the weight ratio of the monoclonal antibody to the trehalose is about any of 1.65, 1.70, 1.80, 1.90, 2.00, 2.08, 2.10, 2.20, 2.30, 2.31, 2.38, 2.40, 2.48, 2.50, 2.60, 2.70, 2.80, 2.90, 2.91, 3.00, 3.10, 3.20, 3.30, 3.40, 3.50, 3.70, 3.80, 3.90, 4.00, 4.10, 4.20, 4.30, 4.40, 4.50, 4.60, 4.70, 4.80, 4.90, and 4.95, including every value in between these numbers. In some embodiments, the monoclonal antibody in the formulation is about 25 mg/mL to about 100 mg/mL. In some embodiments, the monoclonal antibody in the formulation is about 45 mg/mL to about 55 mg/mL. In some embodiments, the monoclonal antibody in the formulation is about 35 mg/mL to about 75 mg/mL. In some embodiments, the trehalose in the formulation is about 40 mM to about 120 mM. In some embodiments, the trehalose in the formulation is about 50 mM to about 70 mM. In some embodiments, the trehalose in the formulation is about 40 mM to about 80 mM. In some embodiments, the buffer is an amount of about 15 mM to about 35 mM. In some embodiments, the buffer is histidine or sodium phosphate.

In another aspect, the invention provides stable aqueous pharmaceutical formulations comprising (a) a monoclonal antibody in an amount of about 25 mg/mL to about 100 mg/mL; (b) trehalose in an amount of about 40 mM to about 120 mM; and (c) sodium phosphate in an amount of about 15 mM to about 35 mM, wherein said formulation has a pH of about 5.5 to about 7.0, and an optional surfactant. In some embodiments, the weight ratio of the monoclonal antibody to the trehalose in the formulation is about 1.65 to about 3.30. In some embodiments, the weight ratio of the monoclonal antibody to the trehalose is about 1.70 to about 2.91. In some embodiments, the weight ratio of the monoclonal antibody to the trehalose is about 2.00 to about 3.30. In some embodiments, the weight ratio of the monoclonal antibody to the trehalose is any of 1.65, 1.70, 1.80, 1.90, 2.00, 2.08, 2.10, 2.20, 2.30, 2.31, 2.38, 2.40, 2.48, 2.50, 2.60, 2.70, 2.80, 2.90, 2.91, 3.00, 3.10, 3.20, 3.30, 3.40, 3.50, 3.70, 3.80, 3.90, 4.00, 4.10, 4.20, 4.30, 4.40, 4.50, 4.60, 4.70, 4.80, 4.90, and 4.95, including every value in between these numbers.

In some embodiments, the monoclonal antibody in the formulation described herein is in an amount of about 30 mg/mL to about 90 mg/mL, about 35 mg/mL to about 85 mg/mL, about 35 mg/mL to 75 mg/mL, about 40 mg/mL to about 80 mg/mL, about 45 mg/mL to about 70 mg/mL, or about 45 mg/mL to about 55 mg/mL. In some embodiments, the monoclonal antibody in the formulation is about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL, including every value in between these numbers. In some embodiments, the monoclonal antibody in the formulation is about 45 mg/mL, about 50 mg/mL, or about 55 mg/mL.

In some embodiments, the formulation described herein comprises the trehalose in about 40 mM to about 110 mM, about 45 mM to about 110 mM, about 50 mM to about 100 mM, about 50 mM to about 90 mM, about 50 mM to about 70 mM, or about 40 mM to about 80 mM. In some embodiments, the trehalose in the formulation is about 40 mM, about 45 mM, about 50 mM, about 55 mM, about 65 mM, about 70 mM, about 75 mM, about 80 mM, about 85 mM, about 90 mM, about 95 mM, about 100 mM, about 105 mM, about 110 mM, about 115 mM, or about 120 mM, including every value in between these numbers. In some embodiments, the trehalose in the formulation is about 50 mM, about 55 mM, about 60 mM, or about 65 mM. In some embodiments, the formulation comprises sodium phosphate as a buffer. In some embodiments, the sodium phosphate in the formulation is about 15 mM to about 30 mM, about 20 mM to 30 mM, about 22 mM to about 28 mM. In some embodiments, the sodium phosphate in the formulation is about 15 mM, about 20 mM, about 22 mM, about 25 mM, about 28 mM, about 30 mM, or about 35 mM, including every value in between these numbers. In some embodiments, the formulation comprises the monoclonal antibody in an amount of about 45 mg/mL to about 55 mg/mL, trehalose in an amount of about 50 mM to about 70 mM, and sodium phosphate in an amount of 22 mM to about 28 mM. In some embodiments, the formulation comprises the monoclonal antibody in an amount of about 45 mg/mL to about 55 mg/mL, trehalose in an amount of about 50 mM to about 70 mM, and sodium phosphate in an amount of 22 mM to about 28 mM, wherein the weight ratio of the antibody to the trehalose is about 1.70 to about 2.91. In some embodiments, the formulation comprises the monoclonal antibody in an amount of about 50 mg/mL, trehalose in an amount of about 60 mM and sodium phosphate in an amount of about 25 mM. In some embodiments, the formulation comprises histidine (such as L-histidine) as a buffer. In some embodiments, the histidine in the formulation is about 15 mM to about 30 mM, about 20 mM to 30 mM, about 22 mM to about 28 mM. In some embodiments, the histidine in the formulation is about 15 mM, about 20 mM, about 22 mM, about 25 mM, about 28 mM, about 30 mM, or about 35 mM, including every value in between these numbers. In some embodiments, the formulation comprises the monoclonal antibody in an amount of about 50 mg/mL, trehalose in an amount of about 40 mM and histidine in an amount of about 20 mM.

In some embodiments, the formulation described herein further comprises a surfactant. In some embodiments, surfactant is polysorbate (such as polysorbate 20) or poloxamer (such as poloxamer 188). In some embodiments, surfactant concentration is about 0.01% to about 0.1%, about 0.01% to about 0.05%, or about 0.02% to about 0.04%. In some embodiments, the surfactant concentration is about 0.01%, about 0.02%, about 0.03%, about 0.04%, about 0.05%, or about 0.1%, including every value in between these numbers.

In some embodiments, the formulation described herein has a pH about 5.5 to about 6.5, about 5.8 to about 6.8, about 5.9 to about 6.5, about 6.0 to about 6.5, about 6.0 to about 6.4, or about 6.0 to about 6.2. In some embodiments, the formulation has a pH about 5.6, about 5.8, about 5.9, about 6.0, about 6.2, about 6.4, about 6.5, about 6.8, or about 7.0, including every value in between these numbers.

In some embodiments, the monoclonal antibody in the formulation described herein is not subject to prior lyophilization. In some embodiments, the monoclonal antibody is a full length antibody. In some embodiments, the monoclonal antibody is an IgG1, IgG2, or IgG4 antibody. In some embodiments, the monoclonal antibody is a humanized antibody, a chimeric antibody or a human antibody. In some embodiments, the monoclonal antibody is an antibody fragment comprising an antigen-binding region. In some embodiments, the antibody fragment is a Fab or F(ab')$_2$ fragment. In some embodiments, the monoclonal antibody binds VEGF. In some embodiments, the antibody is bevacizumab. In some embodiments, the monoclonal antibody is susceptible to aggregation. In some embodiments, the formulation comprises bevacizumab in an amount of about 45 mg/mL to about 55 mg/mL, trehalose in an amount of about 50 mM to about 70 mM, and sodium phosphate in an amount of 22 mM to about 28 mM, and polysorbate 20 in an amount of 0.04%, and the formulation has a pH of about 5.9 to about 6.5. In some embodiments, the formulation comprises bevacizumab in an amount of about 45 mg/mL to about 55 mg/mL, trehalose in an amount of about 50 mM to about 70 mM, and sodium phosphate in an amount of 22 mM to about 28 mM, and polysorbate 20 in an amount of 0.04%, and the formulation has a pH of about 5.9 to about 6.5, wherein the weight ratio of the antibody to the trehalose is about 1.70 to about 2.91. In some embodiments, the formulation comprises bevacizumab in an amount of about 50 mg/mL, trehalose in an amount of about 60 mM, sodium phosphate in an amount of about 25 mM, and polysorbate 20 in an amount of 0.04%, and the formulation has a pH of about 6.2.

In some embodiments, the monoclonal antibody is not subject to prior lyophilization. In some embodiments, the monoclonal antibody is a full length antibody. In some embodiments, the monoclonal antibody is an IgG1, IgG2, or IgG4 antibody. In some embodiments, the monoclonal antibody is a humanized antibody, a chimeric antibody or a human antibody. In some embodiments, the monoclonal antibody is an antibody fragment comprising an antigen-binding region. In some embodiments, the antibody fragment is a Fab or F(ab')$_2$ fragment. In some embodiments, the monoclonal antibody binds CD20. In some embodiments, the antibody that binds CD20 is a humanized B-Ly1 antibody described herein. In some embodiments, the antibody that binds CD20 is an antibody comprising a heavy chain variable region amino acid sequence selected from SEQ ID NO:3 to SEQ ID NO:19 and a light chain variable region amino acid sequence of SEQ ID NO:20. In some embodiments, the antibody is obinutuzumab. In some embodiments, the monoclonal antibody is susceptible to aggregation. In some embodiments, the formulation comprises obinutuzumab in an amount of about 45 mg/mL to about 55 mg/mL, trehalose in an amount of about 50 mM to about 70 mM, and sodium phosphate in an amount of 22 mM to about 28 mM, and polysorbate 20 in an amount of 0.04%, and the formulation has a pH of about 5.9 to about 6.5. In some embodiments, the formulation comprises obinutuzumab in an amount of about 50 mg/mL, trehalose in an amount of about 60 mM, sodium phosphate in an amount of about 25 mM, and polysorbate 20 in an amount of 0.04%, and the formulation has a pH of about 6.2. In some embodiments, the formulation comprises obinutuzumab in an amount of about 50 mg/mL, trehalose in an amount of about 40 mM, histidine in an amount of about 20 mM, and poloxamer 188 in an amount of 0.02%, and said formulation has a pH of about 6.0.

In some embodiments, the formulation described herein is stable at −20° C. for at least about 6 months, at least about 12 months, at least about 15 months, at least about 18 months, at least about 19 months, at least about 20 months, or at least about 2 years. In some embodiments, the formulation is sterile. In some embodiments, the formulation is for administration to a subject. In some embodiments, the formulation is for intravenous (IV), subcutaneous (SQ) or instramuscular (IM) administration.

In another aspect, the invention provides articles of manufacture comprising a container holding a stable aqueous pharmaceutical formulation described herein. In some embodiments, the formulation comprises a monoclonal antibody, trehalose, and a buffer, wherein the weight ratio of said monoclonal antibody to said trehalose in the formulation is about 1.65 to about 4.95, and wherein the formulation has a pH of about 5.5 to about 7.0. In some embodiments, the formulation comprises (a) a monoclonal antibody in an amount of about 25 to about 100 mg/mL; (b) trehalose in an amount of about 40 to about 120 mM; and (c) sodium phosphate in an amount of about 15 to about 35 mM, wherein said formulation has a pH of about 5.5 to about 7.0, and an optional surfactant. In some embodiments, the weight ratio of the monoclonal antibody to the trehalose in the formulation is about 1.65 to about 3.30. In some embodiments, the weight ratio of the monoclonal antibody to the trehalose is about 1.70 to about 2.91. In some embodiments, the weight ratio of the monoclonal antibody to the trehalose is about 2.00 to about 3.30. In some embodiments, the weight ratio of the monoclonal antibody to the trehalose in the formulation is about any of 1.65, 1.70, 1.80, 1.90, 2.00, 2.08, 2.10, 2.20, 2.30, 2.31, 2.38, 2.40, 2.48, 2.50, 2.60, 2.70, 2.80, 2.90, 2.91, 3.00, 3.10, 3.20, 3.30, 3.40, 3.50, 3.70, 3.80, 3.90, 4.00, 4.10, 4.20, 4.30, 4.40, 4.50, 4.60, 4.70, 4.80, 4.90, and 4.95, including every value in between these numbers.

In some embodiments, the monoclonal antibody in the formulation is in an amount of about 30 mg/mL to about 90 mg/mL, about 35 mg/mL to about 85 mg/mL, about 35 mg/mL to about 75 mg/mL, about 40 mg/mL to about 80 mg/mL, about 45 mg/mL to about 70 mg/mL, or about 45 mg/mL to about 55 mg/mL. In some embodiments, the monoclonal antibody in the formulation is about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL, including every value in between these numbers. In some embodiments, the monoclonal antibody in the formulation is about 45 mg/mL, about 50 mg/mL, or about 55 mg/mL.

In some embodiments, the formulation comprises the trehalose in about 40 mM to about 110 mM, about 50 mM to about 100 mM, about 50 mM to about 90 mM, about 50 mM to about 70 mM, or about 40 to about 80 mM. In some embodiments, the trehalose in the formulation is about 40 mM, about 45 mM, about 50 mM, about 55 mM, about 65 mM, about 70 mM, about 75 mM, about 80 mM, about 85 mM, about 90 mM, about 95 mM, about 100 mM, about 105 mM, about 110 mM, about 115 mM, or about 120 mM, including every value in between these numbers. In some embodiments, the trehalose in the formulation is about 40 mM, 50 mM, about 55 mM, about 60 mM, or about 65 mM. In some embodiments, the formulation comprises sodium phosphate as a buffer. In some embodiments, the sodium phosphate in the formulation is about 15 mM to about 30 mM, about 20 mM to 30 mM, about 22 mM to about 28 mM. In some embodiments, the sodium phosphate in the formulation is about 15 mM, about 20 mM, about 22 mM, about 25 mM, about 28 mM, about 30 mM, or about 35 mM, including every value in between these numbers. In some embodiments, the formulation comprises the monoclonal antibody in an amount of about 45 mg/mL to about 55 mg/mL, trehalose in an amount of about 50 mM to about 70 mM, and sodium phosphate in an amount of 22 mM to about 28 mM. In some embodiments, the formulation comprises the monoclonal antibody in an amount of about 45 mg/mL to about 55 mg/mL, trehalose in an amount of about 50 mM to about 70 mM, and sodium phosphate in an amount of 22 mM to about 28 mM, wherein the weight ratio of the antibody to the trehalose is about 1.70 to about 2.91. In some embodiments, the formulation comprises the monoclonal antibody in an amount of about 50 mg/mL, the trehalose in an amount of about 60 mM and the sodium phosphate in an amount of about 25 mM. In some embodiments, the formulation comprises histidine (such as L-histidine) as a buffer. In some embodiments, the histidine in the formulation is about 15 mM to about 30 mM, about 20 mM to 30 mM, about 22 mM to about 28 mM. In some embodiments, the histidine in the formulation is about 15 mM, about 20 mM, about 22 mM, about 25 mM, about 28 mM, about 30 mM, or about 35 mM, including every value in between these numbers. In some embodiments, the formulation comprises the monoclonal antibody in an amount of about 50 mg/mL, trehalose in an amount of about 40 mM and histidine in an amount of about 20 mM.

In some embodiments, the formulation further comprises a surfactant. In some embodiments, surfactant is polysorbate (such as polysorbate 20) or poloxamer (such as poloxamer 188). In some embodiments, the surfactant concentration is about 0.01% to about 0.1%, about 0.01% to about 0.05%, or about 0.02% to about 0.04%. In some embodiments, the surfactant concentration is about 0.01%, about 0.02%, about 0.03%, about 0.04%, about 0.05%, or about 0.1%, including every value in between these numbers.

In some embodiments, the formulation has a pH about 5.5 to about 6.5, about 5.8 to about 6.8, about 5.9 to about 6.5, about 6.0 to about 6.5, about 6.0 to about 6.4, or about 6.0 to about 6.2. In some embodiments, the formulation has a pH about 5.6, about 5.8, about 5.9, about 6.0, about 6.2, about 6.4, about 6.5, about 6.8, or about 7.0, including every value in between these numbers.

In some embodiments, the monoclonal antibody is not subject to prior lyophilization. In some embodiments, the monoclonal antibody is a full length antibody. In some embodiments, the monoclonal antibody is an IgG1, IgG2, or IgG4 antibody. In some embodiments, the monoclonal antibody is a humanized antibody, a chimeric antibody or a human antibody. In some embodiments, the monoclonal antibody is an antibody fragment comprising an antigen-binding region. In some embodiments, the antibody fragment is a Fab or F(ab')$_2$ fragment. In some embodiments, the monoclonal antibody binds VEGF. In some embodiments, the monoclonal antibody is susceptible to aggregation. In some embodiments, the formulation comprises bevacizumab in an amount of about 45 mg/mL to about 55 mg/mL, trehalose in an amount of about 50 mM to about 70 mM, and sodium phosphate in an amount of 22 mM to about 28 mM, and polysorbate 20 in an amount of 0.04%, and the formulation has a pH of about 5.9 to about 6.5. In some embodiments, the formulation comprises bevacizumab in an amount of about 45 mg/mL to about 55 mg/mL, trehalose in an amount of about 50 mM to about 70 mM, and sodium phosphate in an amount of 22 mM to about 28 mM, and polysorbate 20 in an amount of 0.04%, and the formulation has a pH of about 5.9 to about 6.5, wherein the weight ratio of the antibody to the trehalose is about 1.70 to about 2.91. In some embodiments, the formulation comprises bevacizumab in an amount of about 50 mg/mL, trehalose in an amount of about 60 mM, sodium phosphate in an amount of about 25 mM, and polysorbate 20 in an amount of 0.04%, and the formulation has a pH of about 6.2.

In some embodiments, the monoclonal antibody is not subject to prior lyophilization. In some embodiments, the monoclonal antibody is a full length antibody. In some embodiments, the monoclonal antibody is an IgG1, IgG2, or IgG4 antibody. In some embodiments, the monoclonal antibody is a humanized antibody, a chimeric antibody or a human antibody. In some embodiments, the monoclonal antibody is an antibody fragment comprising an antigen-binding region. In some embodiments, the antibody fragment is a Fab or F(ab')$_2$ fragment. In some embodiments, the monoclonal antibody binds CD20. In some embodiments, the antibody that binds CD20 is a humanized B-Ly1 antibody described herein. In some embodiments, the antibody that binds CD20 is an antibody comprising a heavy chain variable region amino acid sequence selected from SEQ ID NO:3 to SEQ ID NO:19 and a light chain variable region amino acid sequence of SEQ ID NO:20. In some embodiments, the antibody is obinutuzumab. In some embodiments, the monoclonal antibody is susceptible to aggregation. In some embodiments, the formulation comprises obinutuzumab in an amount of about 45 mg/mL to about 55 mg/mL, trehalose in an amount of about 50 mM to about 70 mM, and sodium phosphate in an amount of 22 mM to about 28 mM, and polysorbate 20 in an amount of 0.04%, and the formulation has a pH of about 5.9 to about 6.5. In some embodiments, the formulation comprises obinutuzumab in an amount of about 50 mg/mL, trehalose in an amount of about 60 mM, sodium phosphate in an amount of about 25 mM, and polysorbate 20 in an amount of 0.04%, and the formulation has a pH of about 6.2. In some embodiments, the formulation comprises obinutuzumab in an amount of about 50 mg/mL, trehalose in an amount of about 40 mM, histidine in an amount of about 20 mM, and poloxamer 188 is in an amount of 0.02%, and the formulation has a pH of about 6.0.

In some embodiments, the formulation is stable at −20° C. for at least about 6 months, at least about 12 months, at least about 15 months, at least about 18 months, at least about 19 months, at least about 20 months, or at least about 2 years. In some embodiments, the formulation is sterile. In some embodiments, the formulation is for administration to a subject. In some embodiments, the formulation is for intravenous (IV), subcutaneous (SQ) or instramuscular (IM) administration.

In some embodiments, the container is a vial with a stopper pierceable by a syringe, wherein the vial comprises any one of the formulations described herein. In some embodiments, the vial is stored at about 2-8° C. In some embodiments, the vial is stored at about −20° C. In some embodiments, the vial is a 3 cc, 20 cc or 50 cc vial.

In another aspect, the invention provides stainless steel tanks comprising any one of the formulations described herein inside the tank. In some embodiments, the formulation is frozen.

In another aspect, the invention provides methods of reducing aggregation of a therapeutic monoclonal antibody. In some embodiment, the method comprises formulating the monoclonal antibody in a formulation comprising trehalose and a buffer, wherein the weight ratio of the monoclonal antibody to the trehalose in the formulation is about 1.65 to about 4.95, and wherein the formulation has a pH of about 5.5 to about 7.0. In some embodiments, the method comprises formulating the antibody in a formulation comprising trehalose in an amount of about 40 mM to about 120 mM and sodium phosphate in an amount of about 15 mM to about 35 mM, and said formulation having a pH of about 5.5 to about 7.0, wherein said monoclonal antibody is formulated in an amount of about 25 mg/mL to about 100 mg/mL in the formulation.

In some embodiments of the method described herein, the weight ratio of said monoclonal antibody to said trehalose in the formulation is about 1.65 to about 3.30. In some embodiments of the methods described herein, the weight ratio of the monoclonal antibody to the trehalose is about 1.70 to about 2.91. In some embodiments, the weight ratio of the monoclonal antibody to the trehalose is about 2.00 to about 3.30. In some embodiments, the weight ratio of the monoclonal antibody to the trehalose is about any of 1.65, 1.70, 1.80, 1.90, 2.00, 2.08, 2.10, 2.20, 2.30, 2.31, 2.38, 2.40, 2.48, 2.50, 2.60, 2.70, 2.80, 2.90, 2.91, 3.00, 3.10, 3.20, 3.30, 3.40, 3.50, 3.70, 3.80, 3.90, 4.00, 4.10, 4.20, 4.30, 4.40, 4.50, 4.60, 4.70, 4.80, 4.90, and 4.95, including every value in between these numbers.

In some embodiments, the monoclonal antibody in the formulation is in an amount of about 30 mg/mL to about 90 mg/mL, about 35 mg/mL to about 85 mg/mL, about 35 mg/mL to about 75 mg/mL, about 40 mg/mL to about 80 mg/mL, about 45 mg/mL to about 70 mg/mL, or about 45 mg/mL to about 55 mg/mL. In some embodiments, the monoclonal antibody in the formulation is about 25 mg/mL, about 30 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL, including every value in between these numbers. In some embodiments, the monoclonal antibody in the formulation is about 45 mg/mL, about 50 mg/mL, or about 55 mg/mL.

In some embodiments, the formulation comprises the trehalose in about 40 mM to about 110 mM, about 50 mM to about 100 mM, about 50 mM to about 90 mM, about 50 mM to about 70 mM, or about 40 to about 80 mM. In some embodiments, the trehalose in the formulation is about 40 mM, about 45 mM, about 50 mM, about 55 mM, about 65 mM, about 70 mM, about 75 mM, about 80 mM, about 85 mM, about 90 mM, about 95 mM, about 100 mM, about 105 mM, about 110 mM, about 115 mM, or about 120 mM. In some embodiments, the trehalose in the formulation is about 40 mM, about 50 mM, about 55 mM, about 60 mM, or about 65 mM, including every value in between these numbers. In some embodiments, the formulation comprises sodium phosphate as a buffer. In some embodiments, the sodium phosphate in the formulation is about 15 mM to about 30 mM, about 20 mM to 30 mM, about 22 mM to about 28 mM. In some embodiments, the sodium phosphate in the formulation is about 15 mM, about 20 mM, about 22 mM, about 25 mM, about 28 mM, about 30 mM, or about 35 mM, including every value in between these numbers. In some embodiments, the formulation comprises the monoclonal antibody in an amount of about 45 mg/mL to about 55 mg/mL, trehalose in an amount of about 50 mM to about 70 mM, and sodium phosphate in an amount of 22 mM to about 28 mM. In some embodiments, the formulation comprises the monoclonal antibody in an amount of about 45 mg/mL to about 55 mg/mL, trehalose in an amount of about 50 mM to about 70 mM, and sodium phosphate in an amount of 22 mM to about 28 mM, wherein the weight ratio of the antibody to the trehalose is about 1.70 to about 2.91. In some embodiments, the formulation comprises the monoclonal antibody in an amount of about 50 mg/mL, trehalose in an amount of about 60 mM and sodium phosphate in an amount of about 25 mM. In some embodiments, the formulation comprises histidine (such as L-histidine) as a buffer. In some embodiments, the histidine in the formulation is about 15 mM to about 30 mM, about 20 mM to 30 mM, about 22 mM to about 28 mM. In some embodiments, the histidine in the formulation is about 15 mM, about 20 mM, about 22 mM, about 25 mM, about 28 mM, about 30 mM, or about 35 mM, including every value in between these numbers. In some embodiments, the formulation comprises the monoclonal antibody in an amount of about 50 mg/mL, trehalose in an amount of about 40 mM and histidine in an amount of about 20 mM.

In some embodiments, the formulation further comprises a surfactant. In some embodiments, surfactant is polysorbate (such as polysorbate 20) or poloxamer (such as poloxamer 188). In some embodiments, surfactant concentration is about 0.01% to about 0.1%, about 0.01% to about 0.05%, or about 0.02% to about 0.04%. In some embodiments, the surfactant concentration is about 0.01%, about 0.02%, about 0.03%, about 0.04%, about 0.05%, or about 0.1%, including every value in between these numbers.

In some embodiments, the formulation has a pH about 5.5 to about 6.5, about 5.8 to about 6.8, about 5.9 to about 6.5, about 6.0 to about 6.5, about 6.0 to about 6.4, or about 6.0 to about 6.2. In some embodiments, the formulation has a pH about 5.6, about 5.8, about 5.9, about 6.0, about 6.2, about 6.4, about 6.5, about 6.8, or about 7.0, including every value in between these numbers.

In some embodiments, the monoclonal antibody is not subject to prior lyophilization. In some embodiments, the monoclonal antibody is a full length antibody. In some embodiments, the monoclonal antibody is an IgG1, IgG2, or IgG4 antibody. In some embodiments, the monoclonal antibody is a humanized antibody, a chimeric antibody or a human antibody. In some embodiments, the monoclonal antibody is an antibody fragment comprising an antigen-binding region. In some embodiments, the antibody fragment is a Fab or F(ab')$_2$ fragment. In some embodiments, the monoclonal antibody binds VEGF. In some embodiments, the monoclonal antibody is susceptible to aggregation. In some embodiments, the formulation comprises bevacizumab in an amount of about 45 mg/mL to about 55 mg/mL, trehalose in an amount of about 50 mM to about 70 mM, and sodium phosphate in an amount of 22 mM to about 28 mM, and polysorbate 20 in an amount of 0.04%, and the formulation has a pH of about 5.9 to about 6.5. In some embodiments, the formulation comprises bevacizumab in an amount of about 45 mg/mL to about 55 mg/mL, trehalose in an amount of about 50 mM to about 70 mM, and sodium phosphate in an amount of 22 mM to about 28 mM, and polysorbate 20 in an amount of 0.04%, and the formulation has a pH of about 5.9 to about 6.5, wherein the weight ratio of the antibody to the trehalose is about 1.70 to about 2.91. In some embodiments, the formulation comprises bevacizumab in an amount of about 50 mg/mL, trehalose in an amount of about 60 mM, sodium phosphate in an amount of about 25 mM, and polysorbate 20 in an amount of 0.04%, and the formulation has a pH of about 6.2.

In some embodiments, the monoclonal antibody is not subject to prior lyophilization. In some embodiments, the monoclonal antibody is a full length antibody. In some embodiments, the monoclonal antibody is an IgG1, IgG2, or IgG4 antibody. In some embodiments, the monoclonal antibody is a humanized antibody, a chimeric antibody or a human antibody. In some embodiments, the monoclonal antibody is an antibody fragment comprising an antigen-binding region. In some embodiments, the antibody fragment is a Fab or F(ab')$_2$ fragment. In some embodiments, the monoclonal antibody binds CD20. In some embodiments, the antibody that binds CD20 is a humanized B-Ly1 antibody described herein. In some embodiments, the antibody that binds CD20 is an antibody comprising a heavy chain variable region amino acid sequence selected from SEQ ID NO:3 to SEQ ID NO:19 and a light chain variable region amino acid sequence of SEQ ID NO:20. In some embodiments, the antibody is obinutuzumab. In some embodiments, the monoclonal antibody is susceptible to aggregation. In some embodiments, the formulation comprises obinutuzumab in an amount of about 45 mg/mL to about 55 mg/mL, trehalose in an amount of about 50 mM to about 70 mM, and sodium phosphate in an amount of 22 mM to about 28 mM, and polysorbate 20 in an amount of 0.04%, and the formulation has a pH of about 5.9 to about 6.5. In some embodiments, the formulation comprises obinutuzumab in an amount of about 50 mg/mL, trehalose in an amount of about 60 mM, sodium phosphate in an amount of about 25 mM, and polysorbate 20 in an amount of 0.04%, and the formulation has a pH of about 6.2. In some embodiments, the formulation comprises obinutuzumab in an amount of about 50 mg/mL, trehalose in an amount of about 40 mM, histidine in an amount of about 20 mM, and poloxamer 188 is in an amount of 0.02%, and the formulation has a pH of about 6.0.

In some embodiments, the formulation is stable at −20° C. for at least about 6 months, at least about 12 months, at least about 15 months, at least about 18 months, at least about 19 months, at least about 20 months, or at least about 2 years. In some embodiments, the formulation is sterile. In some embodiments, the formulation is for administration to a subject. In some embodiments, the formulation is for intravenous (IV), subcutaneous (SQ) or instramuscular (IM) administration.

In another aspect, the invention provides methods of making a pharmaceutical formulation comprising: (a) preparing any one of the formulations described herein; and (b) evaluating physical stability, chemical stability, or biological activity of the antibody in the formulation. In some embodiments, the physical stability, chemical stability, or biological activity of the antibody in the formulation is evaluated at about 6 months, about 12 months, about 18 months, or about 24 months after the formulation is stored (e.g., at −20° C. or −40° C.).

In another aspect, the invention provides methods of treating a disease or disorder in a subject comprising administering any one of the formulations described herein to a subject in an amount effective to treat the disease or disorder. In some embodiments, the formulation comprises an antibody that binds to VEGF. In some embodiments, the antibody is bevacizumab. In some embodiments, the disease is cancer. In some embodiments, the cancer is selected from colorectal cancer, lung cancer, breast cancer, renal cancer, and glioblastoma.

In another aspect, the invention provides methods of treating a disease or disorder in a subject comprising administering any one of the formulations described herein to a subject in an amount effective to treat the disease or disorder. In some embodiments, the formulation comprises an antibody that binds to CD20. In some embodiments, the antibody is obinutuzumab. In some embodiments, the disease is cancer. In some embodiments, the cancer is a CD20 expression cancer, for example, lymphoma, lymphocytic leukemia, and multiple myeloma.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 3A) Bevacizumab formulation B ($F_B$) shown in FIG. 3A are resistant to formation of aggregates even under accelerated aggregation conditions as compared to formulation A ($F_A$) when stored at −20° C. FIG. 3B) Storage of bevacizumab formulations at −40° C. prevented any increase in total aggregate formation.

FIG. 5A) Obinutuzumab formulations stored at −20° C. for 52 weeks. FIG. 5B) Obinutuzumab formulations stored at −40° C. for 52 weeks.

FIG. 7A) Coefficient plot with scaled and centered coefficients for high molecular weight species (HMWS) formation at −20° C. FIG. 7B) Interaction Plot for cMAb * cTreh. FIG. 7C) Response contour plot for HMWS with cMAb and cTreh as axes and time fixed at high level.

DETAILED DESCRIPTION

I. Definitions

Figure 1:
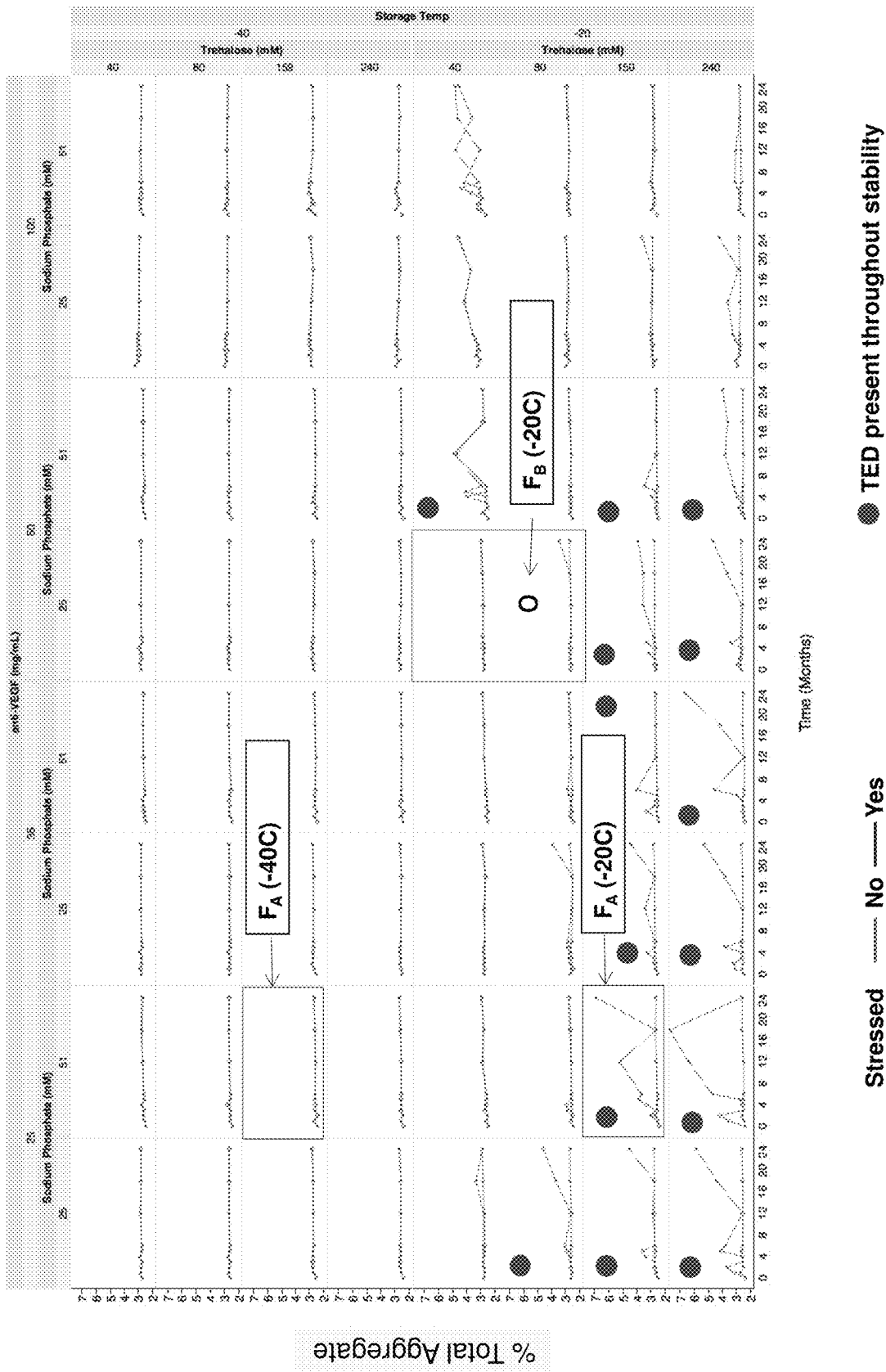
FIG. 1 is a graph demonstrating the presence of high molecular weight species in different bevacizumab formulations when stored for 24 months at a temperature of −40° C. or −20° C.

Before describing the invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

A "sterile" formulation is aseptic or free or essentially free from all living microorganisms and their spores.

A "frozen" formulation is one at a temperature below 0° C. Generally, the frozen formulation is not freeze-dried, nor is it subjected to prior, or subsequent, lyophilization. In certain embodiments, the frozen formulation comprises frozen drug substance for storage (in stainless steel tank) or frozen drug product (in final vial configuration).

A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993), for example. Stability can be measured at a selected temperature for a selected time period. In certain embodiments, the formulation is stable at about 40° C. for at least about 1, 2, 3, 4, 5, 6, 7, 14, 21, 28, or more days. In certain embodiments, the formulation is stable at about 40° C. for at least about 1, 2, 3, 4, 5, 6, 7, 8, or more weeks. In certain embodiments, the formulation is stable at about 25° C. for at least 1, 2, 3, 4, 5, 6, 7, 8, 9, 10, 11, 12, 13, 14, 15, 16, 17, 18, 19, 20, 21, 22, 23, 24, or more months. In certain embodiments, the formulation is stable at about 5° C. for at least 1, 2, 3, 4, 5, 6, 7, 8, 9, 10, 11, 12, 13, 14, 15, 16, 17, 18, 19, 20, 21, 22, 23, 24, or more months. In certain embodiments, the formulation is stable at about −20° C. for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. In certain embodiments, the formulation is stable at 5° C. or −20° C. for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. Furthermore, the formulation is preferably stable following freezing (to, e.g., −20° C., −40° C. or −70° C.) and thawing of the formulation, for example following 1, 2 3, 4, or 5 cycles of freezing and thawing. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g. Asn deamidation), oxidation (e.g. Met oxidation), isomerization (e.g. Asp isomerization), clipping/hydrolysis/fragmentation (e.g. hinge region fragmentation), succinimide formation, unpaired cysteine(s), N-terminal extension, C-terminal processing, glycosylation differences, etc.

A protein "retains its physical stability" in a pharmaceutical formulation if it shows no signs or very little of aggregation, precipitation and/or denaturation upon visual examination of color and/or clarity, or as measured by UV light scattering or by size exclusion chromatography.

A protein "retains its chemical stability" in a pharmaceutical formulation, if the chemical stability at a given time is such that the protein is considered to still retain its biological activity as defined below. Chemical stability can be assessed by detecting and quantifying chemically altered forms of the protein. Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography or icIEF, for example.

An antibody "retains its biological activity" in a pharmaceutical formulation, if the biological activity of the antibody at a given time is within about 10% (within the errors of the assay) of the biological activity exhibited at the time the pharmaceutical formulation was prepared as determined in an antigen binding assay, for example. Other "biological activity" assays for antibodies are elaborated herein below.

As used herein, "biological activity" of a monoclonal antibody refers to the ability of the antibody to bind to antigen. It can further include antibody binding to antigen and resulting in a measurable biological response which can be measured in vitro or in vivo. Such activity may be antagonistic or agonistic.

A "deamidated" monoclonal antibody herein is one in which one or more asparagine residue thereof has been derivitized, e.g. to an aspartic acid or an iso-aspartic acid.

An antibody which is "susceptible to deamidation" is one comprising one or more residue, which has been found to be prone to deamidate.

An antibody which is "susceptible to aggregation" is one which has been found to aggregate with other antibody molecule(s), especially upon freezing and/or agitation.

An antibody which is "susceptible to fragmentation" is one which has been found to be cleaved into two or more fragments, for example at a hinge region thereof.

By "reducing deamidation, aggregation, or fragmentation" is intended preventing or decreasing the amount of deamidation, aggregation, or fragmentation relative to the monoclonal antibody formulated in a different formulation.

The antibody which is formulated is preferably essentially pure and desirably essentially homogeneous (e.g., free from contaminating proteins etc.). "Essentially pure" antibody means a composition comprising at least about 90% by weight of the antibody, based on total weight of the composition, preferably at least about 95% by weight. "Essentially homogeneous" antibody means a composition comprising at least about 99% by weight of antibody, based on total weight of the composition.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

As used herein, "buffer" refers to a buffered solution that resists changes in pH by the action of its acid-base conjugate components. The buffer of this invention preferably has a pH in the range from about 4.5 to about 7.0, preferably from about 5.6 to about 7.0, for example from 5.6 to 6.9, 5.7 to 6.8, 5.8 to 6.7, 5.9 to 6.6, 5.9 to 6.5, 6.0, 6.0 to 6.4, or 6.1 to 6.3. In one embodiment the buffer has a pH 5.6, 5.7, 5.8, 5.9, 6.0, 6.1, 6.2, 6.3, 6.4, 6.5, 6.6, 6.7, 6.8, 6.9, or 7.0. For example, sodium phosphate is an example of buffers that will control the pH in this range.

As used herein, a "surfactant" refers to a surface-active agent, preferably a nonionic surfactant. Examples of surfactants herein include polysorbate (for example, polysorbate 20 and, polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g. Pluronics, PF68 etc); etc. In one embodiment, the surfactant herein is polysorbate 20.

In a pharmacological sense, in the context of the invention, a "therapeutically effective amount" of an antibody refers to an amount effective in the prevention or treatment of a disorder for the treatment of which the antibody is effective. A "disorder" is any condition that would benefit from treatment with the antibody. This includes chronic and acute disorders or diseases including those pathological conditions which predispose the mammal to the disorder in question.

A "preservative" is a compound which can be optionally included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. In one embodiment, the preservative herein is benzyl alcohol.

The term "VEGF" or "VEGF-A" as used herein refers to the 165-amino acid human vascular endothelial cell growth factor and related 121-, 189-, and 206-amino acid human vascular endothelial cell growth factors, as described by Leung et al. (1989) *Science* 246:1306, and Houck et al. (1991) *Mol. Endocrin* 5:1806, together with the naturally occurring allelic and processed forms thereof. The term "VEGF" also refers to VEGFs from non-human species such as mouse, rat or primate. Sometimes the VEGF from a specific species are indicated by terms such as hVEGF for human VEGF, mVEGF for murine VEGF, and etc. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)" or "VEGF$_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

"VEGF biological activity" includes binding to any VEGF receptor or any VEGF signaling activity such as regulation of both normal and abnormal angiogenesis and vasculogenesis (Ferrara and Davis-Smyth (1997) *Endocrine Rev.* 18:4-25; Ferrara (1999) *J. Mol. Med.* 77:527-543); promoting embryonic vasculogenesis and angiogenesis (Carmeliet et al. (1996) *Nature* 380:435-439; Ferrara et al. (1996) *Nature* 380:439-442); and modulating the cyclical blood vessel proliferation in the female reproductive tract and for bone growth and cartilage formation (Ferrara et al. (1998) *Nature Med.* 4:336-340; Gerber et al. (1999) *Nature Med.* 5:623-628). In addition to being an angiogenic factor in angiogenesis and vasculogenesis, VEGF, as a pleiotropic growth factor, exhibits multiple biological effects in other physiological processes, such as endothelial cell survival, vessel permeability and vasodilation, monocyte chemotaxis and calcium influx (Ferrara and Davis-Smyth (1997), supra and Cebe-Suarez et al. *Cell. Mol. Life Sci.* 63:601-615 (2006)). Moreover, recent studies have reported mitogenic effects of VEGF on a few non-endothelial cell types, such as retinal pigment epithelial cells, pancreatic duct cells, and Schwann cells. Guerrin et al. (1995) *J. Cell Physiol.* 164: 385-394; Oberg-Welsh et al. (1997) *Mol. Cell. Endocrinol.* 126:125-132; Sondell et al. (1999) *J. Neurosci.* 19:5731-5740.

A "VEGF antagonist" or "VEGF-specific antagonist" refers to a molecule capable of binding to VEGF, reducing VEGF expression levels, or neutralizing, blocking, inhibiting, abrogating, reducing, or interfering with VEGF biological activities, including, but not limited to, VEGF binding to one or more VEGF receptors and VEGF mediated angiogenesis and endothelial cell survival or proliferation. Included as VEGF-specific antagonists useful in the methods of the invention are polypeptides that specifically bind to VEGF, anti-VEGF antibodies and antigen-binding fragments thereof, receptor molecules and derivatives which bind specifically to VEGF thereby sequestering its binding to one or more receptors, fusions proteins (e.g., VEGF-Trap (Regeneron)), and VEGF$_{121}$-gelonin (Peregrine). VEGF-specific antagonists also include antagonist variants of VEGF polypeptides, antisense nucleobase oligomers directed to VEGF, small RNA molecules directed to VEGF, RNA aptamers, peptibodies, and ribozymes against VEGF. VEGF-specific antagonists also include nonpeptide small molecules that bind to VEGF and are capable of blocking, inhibiting, abrogating, reducing, or interfering with VEGF biological activities. Thus, the term "VEGF activities" specifically includes VEGF mediated biological activities of VEGF. In certain embodiments, the VEGF antagonist reduces or inhibits, by at least 10%, 20%, 30%, 40%, 50%, 60%, 70%, 80%, 90% or more, the expression level or biological activity of VEGF.

An "anti-VEGF antibody" is an antibody that binds to VEGF with sufficient affinity and specificity. In certain embodiments, the antibody selected will normally have a sufficiently binding affinity for VEGF, for example, the antibody may bind hVEGF with a $K_d$ value of between 100 nM$^{-1}$ pM. Antibody affinities may be determined by a surface plasmon resonance based assay (such as the BIAcore assay as described in PCT Application Publication No. WO2005/012359); enzyme-linked immunoabsorbent assay (ELISA); and competition assays (e.g. RIA's), for example.

In certain embodiment, the anti-VEGF antibody can be used as a therapeutic agent in targeting and interfering with diseases or conditions wherein the VEGF activity is involved. Also, the antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B or VEGF-C, nor other growth factors such as P1GF, PDGF or bFGF. In one embodiment, anti-VEGF antibody is a monoclonal antibody that binds to the same epitope as the monoclonal anti-VEGF antibody A4.6.1 produced by hybridoma ATCC HB 10709. In another embodiment, the anti-VEGF antibody is a recombinant humanized anti-VEGF monoclonal antibody generated according to Presta et al. (1997) *Cancer Res.* 57:4593-4599, including but not limited to the antibody known as bevacizumab (BV; AVASTIN®).

The anti-VEGF antibody "Bevacizumab (BV)," also known as "rhuMAb VEGF" or "AVASTIN®," is a recombinant humanized anti-VEGF monoclonal antibody generated according to Presta et al. (1997) *Cancer Res.* 57:4593-4599. It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of Bevacizumab, including most of the framework regions, is derived from human IgG1, and about 7% of the sequence is derived from the murine antibody A4.6.1. Bevacizumab has a molecular mass of about 149,000 Daltons and is glycosylated. Bevacizumab and other humanized anti-VEGF antibodies are further described in U.S. Pat. No. 6,884,879 issued Feb. 26, 2005, the entire disclosure of which is expressly incorporated herein by reference.

The term "B20 series polypeptide" as used herein refers to a polypeptide, including an antibody that binds to VEGF. B20 series polypeptides includes, but not limited to, antibodies derived from a sequence of the B20 antibody or a B20-derived antibody described in US Publication No. 20060280747, US Publication No. 20070141065 and/or US Publication No. 20070020267, the content of these patent applications are expressly incorporated herein by reference. In one embodiment, B20 series polypeptide is B20-4.1 as described in US Publication No. 20060280747, US Publication No. 20070141065 and/or US Publication No. 20070020267. In another embodiment, B20 series polypeptide is B20-4.1.1 described in U.S. Pat. No. 7,910,098, the entire disclosure of which is expressly incorporated herein by reference.

The term "G6 series polypeptide" as used herein refers to a polypeptide, including an antibody that binds to VEGF. G6 series polypeptides includes, but not limited to, antibodies derived from a sequence of the G6 antibody or a G6-derived antibody described in US Publication No. 20060280747, US Publication No. 20070141065 and/or US Publication No. 20070020267. G6 series polypeptides, as described in US Publication No. 20060280747, US Publication No. 20070141065 and/or US Publication No. 20070020267 include, but not limited to, G6-8, G6-23 and G6-31.

For additional antibodies see U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., *Journal of Immunological Methods* 288:149-164 (2004). In certain embodiments, other antibodies include those that bind to a functional epitope on human VEGF comprising of residues F17, M18, D19, Y21, Y25, Q89, 191, K101, E103, and C104 or, alternatively, comprising residues F17, Y21, Q22, Y25, D63, 183 and Q89.

Other anti-VEGF antibodies are also known, and described, for example, in Liang et al., *J Biol Chem* 281, 951-961 (2006).

"CD20" as used herein refers to the human B-lymphocyte antigen CD20 (also known as CD20, B-lymphocyte surface antigen B1, Leu-16, Bp35, BMS, and LF5; the sequence is characterized by the SwissProt database entry P11836) is a hydrophobic transmembrane protein with a molecular weight of approximately 35 kD located on pre-B and mature B lymphocytes. (Valentine, M. A., et al., *J. Biol. Chem.* 264(19) (1989 11282-11287; Tedder, T. F., et al, *Proc. Natl. Acad. Sci. U.S.A.* 85 (1988) 208-12; Stamenkovic, I., et al., *J. Exp. Med.* 167 (1988) 1975-80; Einfeld, D. A., et al., *EMBO J.* 7 (1988) 711-7; Tedder, T. F., et al., *J. Immunol.* 142 (1989) 2560-8). The corresponding human gene is Membrane-spanning 4-domains, subfamily A, member 1, also known as MS4A1. This gene encodes a member of the membrane-spanning 4A gene family. Members of this nascent protein family are characterized by common structural features and similar intron/exon splice boundaries and display unique expression patterns among hematopoietic cells and nonlymphoid tissues. This gene encodes the B-lymphocyte surface molecule which plays a role in the development and differentiation of B-cells into plasma cells. This family member is localized to 11q12, among a cluster of family members. Alternative splicing of this gene results in two transcript variants which encode the same protein.

The terms "CD20" and "CD20 antigen" are used interchangeably herein, and include any variants, isoforms and species homologs of human CD20 which are naturally expressed by cells or are expressed on cells transfected with the CD20 gene. Binding of an antibody of the invention to the CD20 antigen mediate the killing of cells expressing CD20 (e.g., a tumor cell) by inactivating CD20. The killing of the cells expressing CD20 may occur by one or more of the following mechanisms: Cell death/apoptosis induction, ADCC and CDC.

Synonyms of CD20, as recognized in the art, include B-lymphocyte antigen CD20, B-lymphocyte surface antigen B1, Leu-16, Bp35, BMS, and LF5.

The term "anti-CD20 antibody" according to the invention is an antibody that binds specifically to CD20 antigen. Depending on binding properties and biological activities of anti-CD20 antibodies to the CD20 antigen, two types of anti-CD20 antibodies (type I and type II anti-CD20 antibodies) can be distinguished according to Cragg, M. S., et al., *Blood* 103 (2004) 2738-2743; and Cragg, M. S., et al., *Blood* 101 (2003) 1045-1052, see Table 1.

TABLE 1

| Properties of type I and type II anti-CD20 antibodies | |
|---|---|
| Type I anti-CD20 antibodies | type II anti-CD20 antibodies |
| type I CD20 epitope | type II CD20 epitope |
| Localize CD20 to lipid rafts | Do not localize CD20 to lipid rafts |
| Increased CDC (if IgG1 isotype) | Decreased CDC (if IgG1 isotype) |
| ADCC activity (if IgG1 isotype) | ADCC activity (if IgG1 isotype) |
| Full binding capacity | Reduced binding capacity |
| Homotypic aggregation | Stronger homotypic aggregation |
| Apoptosis induction upon cross-linking | Strong cell death induction without cross-linking |

Examples of type II anti-CD20 antibodies include e.g. humanized B-Ly1 antibody IgG1 (a chimeric humanized IgG1 antibody as disclosed in WO 2005/044859), 11B8 IgG1 (as disclosed in WO 2004/035607), and AT80 IgG1. Typically type II anti-CD20 antibodies of the IgG1 isotype show characteristic CDC properties. Type II anti-CD20 antibodies have a decreased CDC (if IgG1 isotype) compared to type I antibodies of the IgG1 isotype.

Examples of type I anti-CD20 antibodies include e.g. rituximab, HI47 IgG3 (ECACC, hybridoma), 2C6 IgG1 (as disclosed in WO 2005/103081), 2F2 IgG1 (as disclosed and WO 2004/035607 and WO 2005/103081) and 2H7 IgG1 (as disclosed in WO 2004/056312).

The afucosylated anti-CD20 antibodies according to the invention is preferably a type II anti-CD20 antibodies, more preferably an afucosylated humanized B-Ly1 antibody as described in WO 2005/044859 and WO 2007/031875.

The "rituximab" antibody (reference antibody; example of a type I anti-CD20 antibody) is a genetically engineered chimeric human gamma 1 murine constant domain containing monoclonal antibody directed against the human CD20 antigen. However this antibody is not glycoengineered and not afocusylates and thus has an amount of fucose of at least 85%. This chimeric antibody contains human gamma 1 constant domains and is identified by the name "C2B8" in U.S. Pat. No. 5,736,137 (Andersen, et. al.) issued on Apr. 17, 1998, assigned to IDEC Pharmaceuticals Corporation. Rituximab is approved for the treatment of patients with relapsed or refracting low-grade or follicular, CD20 positive, B cell non-Hodgkin's lymphoma. In vitro mechanism of action studies have shown that rituximab exhibits human complement-dependent cytotoxicity (CDC) (Reff, M. E., et. al, *Blood* 83(2) (1994) 435-445). Additionally, it exhibits activity in assays that measure antibody-dependent cellular cytotoxicity (ADCC).

The term "humanized B-Ly1 antibody" refers to humanized B-Ly1 antibody as disclosed in WO 2005/044859 and WO 2007/031875, which were obtained from the murine monoclonal anti-CD20 antibody B-Ly1 (variable region of the murine heavy chain (VH): SEQ ID NO: 1; variable region of the murine light chain (VL): SEQ ID NO: 2—see Poppema, S. and Visser, L., *Biotest Bulletin* 3 (1987) 131-139) by chimerization with a human constant domain from IgG1 and following humanization (see WO 2005/044859 and WO 2007/031875). These "humanized B-Ly1 antibodies" are disclosed in detail in WO 2005/044859 and WO 2007/031875.

In one embodiment, the "humanized B-Ly1 antibody" has variable region of the heavy chain (VH) selected from group of SEQ ID No.3 to SEQ ID No.19 (B-HH2 to B-HH9 and B-HL8 to B-HL17 of WO 2005/044859 and WO 2007/031875). In one specific embodiment, such variable domain is selected from the group consisting of SEQ ID No. 3, 4, 7, 9, 11, 13 and 15 (B-HH2, BHH-3, B-HH6, B-HH8, B-HL8, B-HL11 and B-HL13 of WO 2005/044859 and WO 2007/031875). In one specific embodiment, the "humanized B-Ly1 antibody" has variable region of the light chain (VL) of SEQ ID No. 20 (B-KV1 of WO 2005/044859 and WO 2007/031875). In one specific embodiment, the "humanized B-Ly1 antibody" has a variable region of the heavy chain (VH) of SEQ ID No.7 (B-HH6 of WO 2005/044859 and WO 2007/031875) and a variable region of the light chain (VL) of SEQ ID No. 20 (B-KV1 of WO 2005/044859 and WO 2007/031875). Furthermore in one embodiment, the humanized B-Ly1 antibody is an IgG1 antibody. According to the invention such afocusylated humanized B-Ly1 antibodies are glycoengineered (GE) in the Fc region according to the procedures described in WO 2005/044859, WO 2004/065540, WO 2007/031875, Umana, P. et al., Nature Biotechnol. 17 (1999) 176-180 and WO 99/154342. In one embodiment, the afucosylated glyco-engineered humanized B-Ly1 is B-HH6-B-KV1 GE. In one embodiment, the anti-CD20 antibody is obinutuzumab (recommended INN, WHO Drug Information, Vol. 26, No. 4, 2012, p. 453). As used herein, obinutuzumab is synonymous for GA101 or R05072759. This replaces all previous versions (e.g. Vol. 25, No. 1, 2011, p. 75-76), and is formerly known as afutuzumab (recommended INN, WHO Drug Information, Vol. 23, No. 2, 2009, p. 176; Vol. 22, No. 2, 2008, p. 124). In some embodiments, the humanized B-Ly1 antibody is an antibody comprising a heavy chain comprising the amino acid sequence of SEQ ID NO:21 and a light chain comprising the amino acid sequence of SEQ ID NO:22 or an antigen-binding fragment thereof. In some embodiments, the humanized B-Ly1 antibody comprises a heavy chain variable region comprising the three heavy chain CDRs of SEQ ID NO:21 and a light chain variable region comprising the three light chain CDRs of SEQ ID NO:22.

```
Heavy chain
                                                    (SEQ ID NO: 21)
QVQLVQSGAE VKKPGSSVKV SCKASGYAFS YSWINWVRQA PGQGLEWMGR  50

IFPGDGDTDY NGKFKGRVTI TADKSTSTAY MELSSLRSED TAVYYCARNV 100

FDGYWLVYWG QGTLVTVSSA STKGPSVFPL APSSKSTSGG TAALGCLVKD 150

YFPEPVTVSW NSGALTSGVH TFPAVLQSSG LYSLSSVVTV PSSSLGTQTY 200

ICNVNHKPSN TKVDKKVEPK SCDKTHTCPP CPAPELLGGP SVFLFPPKPK 250

DTLMISRTPE VTCVVVDVSH EDPEVKFNWY VDGVEVHNAK TKPREEQYNS 300

TYRVVSVLTV LHQDWLNGKE YKCKVSNKAL PAPIEKTISK AKGQPREPQV 350

YTLPPSRDEL TKNQVSLTCL VKGFYPSDIA VEWESNGQPE NNYKTTPPVL 400

DSDGSFFLYS KLTVDKSRWQ QGNVFSCSVM HEALHNHYTQ KSLSLSPGK  449

Light chain
                                                    (SEQ ID NO: 22)
DIVMTQTPLS LPVTPGEPAS ISCRSSKSLL HSNGITYLYW YLQKPGQSPQ  50

LLIYQMSNLV SGVPDRFSGS GSGTDFTLKI SRVEAEDVGV YYCAQNLELP 100

YTFGGGTKVE IKRTVAAPSV FIFPPSDEQL KSGTASVVCL LNNFYPREAK 150

VQWKVDNALQ SGNSQESVTE QDSKDSTYSL SSTLTLSKAD YEKHKVYACE 200

VTHQGLSSPV TKSFNRGEC                                  219
```

In some embodiments, the humanized B-Ly1 antibody is an afucosylated glyco-engineered humanized B-Ly1. Such glycoengineered humanized B-Ly1 antibodies have an altered pattern of glycosylation in the Fc region, preferably having a reduced level of fucose residues. Preferably the amount of fucose is 60% or less of the total amount of oligosaccharides at Asn297 (in one embodiment the amount of fucose is between 40% and 60%, in another embodiment the amount of fucose is 50% or less, and in still another embodiment the amount of fucose is 30% or less). Furthermore the oligosaccharides of the Fc region are preferably bisected. These glycoengineered humanized B-Ly1 antibodies have an increased ADCC.

The oligosaccharide component can significantly affect properties relevant to the efficacy of a therapeutic glycoprotein, including physical stability, resistance to protease attack, interactions with the immune system, pharmacokinetics, and specific biological activity. Such properties may depend not only on the presence or absence, but also on the specific structures, of oligosaccharides. Some generalizations between oligosaccharide structure and glycoprotein function can be made. For example, certain oligosaccharide structures mediate rapid clearance of the glycoprotein from the bloodstream through interactions with specific carbohydrate binding proteins, while others can be bound by antibodies and trigger undesired immune reactions. (Jenkins, N., et al., *Nature Biotechnol.* 14 (1996) 975-81).

Mammalian cells are the preferred hosts for production of therapeutic glycoproteins, due to their capability to glycosylate proteins in the most compatible form for human application. (Cumming, D. A., et al., *Glycobiology* 1 (1991) 115-30; Jenkins, N., et al., *Nature Biotechnol.* 14 (1996) 975-81). Bacteria very rarely glycosylate proteins, and like other types of common hosts, such as yeasts, filamentous fungi, insect and plant cells, yield glycosylation patterns associated with rapid clearance from the blood stream, undesirable immune interactions, and in some specific cases, reduced biological activity. Among mammalian cells, Chinese hamster ovary (CHO) cells have been most commonly used during the last two decades. In addition to giving suitable glycosylation patterns, these cells allow consistent generation of genetically stable, highly productive clonal cell lines. They can be cultured to high densities in simple bioreactors using serum free media, and permit the development of safe and reproducible bioprocesses. Other commonly used animal cells include baby hamster kidney (BHK) cells, NSO- and SP2/0-mouse myeloma cells. More recently, production from transgenic animals has also been tested. (Jenkins, N., et al., *Nature Biotechnol.* 14 (1996) 975-981).

All antibodies contain carbohydrate structures at conserved positions in the heavy chain constant regions, with each isotype possessing a distinct array of N-linked carbohydrate structures, which variably affect protein assembly, secretion or functional activity. (Wright, A., and Morrison, S. L., *Trends Biotech.* 15 (1997) 26-32). The structure of the attached N-linked carbohydrate varies considerably, depending on the degree of processing, and can include high-mannose, multiply-branched as well as biantennary complex oligosaccharides. (Wright, A., and Morrison, S. L., *Trends Biotech.* 15 (1997) 26-32). Typically, there is heterogeneous processing of the core oligosaccharide structures attached at a particular glycosylation site such that even monoclonal antibodies exist as multiple glycoforms. Likewise, it has been shown that major differences in antibody glycosylation occur between cell lines, and even minor differences are seen for a given cell line grown under different culture conditions. (Lifely, M. R., et al., *Glycobiology* 5(8) (1995) 813-22).

One way to obtain large increases in potency, while maintaining a simple production process and potentially avoiding significant, undesirable side effects, is to enhance the natural, cell-mediated effector functions of monoclonal antibodies by engineering their oligosaccharide component as described in Umana, P., et al., *Nature Biotechnol.* 17 (1999) 176-180 and U.S. Pat. No. 6,602,684. IgG1 type antibodies, the most commonly used antibodies in cancer immunotherapy, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., *Glycobiology* 5 (1995) 813-822; Jefferis, R., et al., *Immunol. Rev.* 163 (1998) 59-76; Wright, A., and Morrison, S. L., *Trends Biotechnol.* 15 (1997) 26-32).

It was previously shown that overexpression in Chinese hamster ovary (CHO) cells of β(1,4)-N-acetylglucosaminyltransferase I11 ("GnTIII7y), a glycosyltransferase catalyzing the formation of bisected oligosaccharides, significantly increases the in vitro ADCC activity of an antineuroblastoma chimeric monoclonal antibody (chCE7) produced by the engineered CHO cells. (See Umana, P., et al., *Nature Biotechnol.* 17 (1999) 176-180; and WO 99/154342, the entire contents of which are hereby incorporated by reference). The antibody chCE7 belongs to a large class of unconjugated monoclonal antibodies which have high tumor affinity and specificity, but have too little potency to be clinically useful when produced in standard industrial cell lines lacking the GnTIII enzyme (Umana, P., et al., *Nature Biotechnol.* 17 (1999) 176-180). That study was the first to show that large increases of ADCC activity could be obtained by engineering the antibody producing cells to express GnTIII, which also led to an increase in the proportion of constant region (Fc)-associated, bisected oligosaccharides, including bisected, non-fucosylated oligosaccharides, above the levels found in naturally-occurring antibodies.

"Treatment" refers to both therapeutic treatment and prophylactic or preventative measures. Those in need of treatment include those already with the disorder as well as those in which the disorder is to be prevented.

A "disorder" is any condition that would benefit from treatment including, but not limited to, chronic and acute disorders or diseases including those pathological conditions which predispose the mammal to the disorder in question. Disorders include angiogenic disorders. "Angiogenic disorder" as used herein refers to any condition involving abnormal angiogenesis or abnormal vascular permeability or leakage. Non-limiting examples of angiogenic disorders to be treated herein include malignant and benign tumors; non-leukemias and lymphoid malignancies; and, in particular, tumor (cancer) metastasis.

"Abnormal angiogenesis" occurs when new blood vessels grow either excessively or otherwise inappropriately (e.g., the location, timing, degree, or onset of the angiogenesis being undesired from a medical standpoint) in a diseased state or such that it causes a diseased state. In some cases, excessive, uncontrolled, or otherwise inappropriate angiogenesis occurs when there is new blood vessel growth that contributes to the worsening of the diseased state or cause of a diseased state. The new blood vessels can feed the diseased tissues, destroy normal tissues, and in the case of cancer, the new vessels can allow tumor cells to escape into the circulation and lodge in other organs (tumor metastases). Examples of disorders involving abnormal angiogenesis include, but are not limited to cancer, especially vascularized solid tumors and metastatic tumors (including colon, lung cancer (especially small-cell lung cancer), or prostate cancer), diseases caused by ocular neovascularisation, especially diabetic blindness, retinopathies, primarily diabetic retinopathy or age-related macular degeneration, choroidal neovascularization (CNV), diabetic macular edema, pathological myopia, von Hippel-Lindau disease, histoplasmosis of the eye, Central Retinal Vein Occlusion (CRVO), corneal neovascularization, retinal neovascularization and rubeosis; psoriasis, psoriatic arthritis, haemangioblastoma such as haemangioma; inflammatory renal diseases, such as glomerulonephritis, especially mesangioproliferative glomerulonephritis, haemolytic uremic syndrome, diabetic nephropathy or hypertensive nephrosclerosis; various inflammatory diseases, such as arthritis, especially rheumatoid arthritis, inflammatory bowel disease, psoriasis, sarcoidosis, arterial arteriosclerosis and diseases occurring after transplants, endometriosis or chronic asthma and other conditions.

"Abnormal vascular permeability" occurs when the flow of fluids, molecules (e.g., ions and nutrients) and cells (e.g., lymphocytes) between the vascular and extravascular compartments is excessive or otherwise inappropriate (e.g., the location, timing, degree, or onset of the vascular permeability being undesired from a medical standpoint) in a diseased state or such that it causes a diseased state. Abnormal vascular permeability may lead to excessive or otherwise inappropriate "leakage" of ions, water, nutrients, or cells through the vasculature. In some cases, excessive, uncontrolled, or otherwise inappropriate vascular permeability or vascular leakage exacerbates or induces disease states including, e.g., edema associated with tumors including, e.g., brain tumors; ascites associated with malignancies; Meigs' syndrome; lung inflammation; nephrotic syndrome; pericardial effusion; pleural effusion; permeability associated with cardiovascular diseases such as the condition following myocardial infarctions and strokes and the like. The present invention contemplates treating those patients that have developed or are at risk of developing the diseases and disorders associated with abnormal vascular permeability or leakage.

The terms "cell proliferative disorder" and "proliferative disorder" refer to disorders that are associated with some degree of abnormal cell proliferation. In one embodiment, the cell proliferative disorder is cancer. In one embodiment, the cell proliferative disorder is a tumor.

"Tumor," as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In certain embodiments, cancers that are amenable to treatment by the antibodies of the invention include breast cancer, colorectal cancer, rectal cancer, non-small cell lung cancer, glioblastoma, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, ovarian cancer, mesothelioma, and multiple myeloma. In some embodiments, the cancer is selected from: small cell lung cancer, gliblastoma, neuroblastomas, melanoma, breast carcinoma, gastric cancer, colorectal cancer (CRC), and hepatocellular carcinoma. Yet, in some embodiments, the cancer is selected from: non-small cell lung cancer, colorectal cancer, glioblastoma and breast carcinoma, including metastatic forms of those cancers.

The term "anti-cancer therapy" refers to a therapy useful in treating cancer. Examples of anti-cancer therapeutic agents include, but are limited to, e.g., chemotherapeutic agents, growth inhibitory agents, cytotoxic agents, agents used in radiation therapy, anti-angiogenic agents, apoptotic agents, anti-tubulin agents, and other agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

An "angiogenic factor or agent" is a growth factor or its receptor which is involved in stimulating the development of blood vessels, e.g., promote angiogenesis, endothelial cell growth, stability of blood vessels, and/or vasculogenesis, etc. For example, angiogenic factors, include, but are not limited to, e.g., VEGF and members of the VEGF family and their receptors (VEGF-B, VEGF-C, VEGF-D, VEGFR1, VEGFR2 and VEGFR3), P1GF, PDGF family, fibroblast growth factor family (FGFs), TIE ligands (Angiopoietins, ANGPT1, ANGPT2), TIE1, TIE2, ephrins, Bv8, Delta-like ligand 4 (DLL4), Del-1, fibroblast growth factors: acidic (aFGF) and basic (bFGF), FGF4, FGF9, BMP9, BMP10, Follistatin, Granulocyte colony-stimulating factor (G-CSF), GM-CSF, Hepatocyte growth factor (HGF)/scatter factor (SF), Interleukin-8 (IL-8), CXCL12, Leptin, Midkine, neuropilins, NRP1, NRP2, Placental growth factor, Platelet-derived endothelial cell growth factor (PD-ECGF), Platelet-derived growth factor, especially PDGF-BB, PDGFR-alpha, or PDGFR-beta, Pleiotrophin (PTN), Progranulin, Proliferin, Transforming growth factor-alpha (TGF-alpha), Transforming growth factor-beta (TGF-beta), Tumor necrosis factor-alpha (TNF-alpha), Alk1, CXCR4, Notch1, Notch4, Sema3A, Sema3C, Sema3F, Robo4, etc. It would further include factors that promote angiogenesis, such as ESM1 and Perlecan. It would also include factors that accelerate wound healing, such as growth hormone, insulin-like growth factor-I (IGF-I), VIGF, epidermal growth factor (EGF), EGF-like domain, multiple 7 (EGFL7), CTGF and members of its family, and TGF-alpha and TGF-beta. See, e.g., Klagsbrun and D'Amore (1991) *Annu. Rev. Physiol.* 53:217-39; Streit and Detmar (2003) *Oncogene* 22:3172-3179; Ferrara & Alitalo (1999) *Nature Medicine* 5(12):1359-1364; Tonini et al. (2003) *Oncogene* 22:6549-6556 (e.g., Table 1 listing known angiogenic factors); and, Sato (2003) *Int. J. Clin. Oncol.* 8:200-206.

An "anti-angiogenic agent" or "angiogenic inhibitor" refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenic agent includes those agents that bind and block the angiogenic activity of the angiogenic factor or its receptor. For example, an anti-angiogenic agent is an antibody or other antagonist to an angiogenic agent as defined above, e.g., antibodies to VEGF-A or to the VEGF-A receptor (e.g., KDR receptor or Flt-1 receptor), anti-PDGFR inhibitors, small molecules that block VEGF receptor signaling (e.g., PTK787/ZK2284, SU6668, SUTENT®/SU11248 (sunitinib malate), AMG706, or those described in, e.g., international patent application WO 2004/113304). Anti-angiogenic agents include, but are not limited to, the following agents: VEGF inhibitors such as a VEGF-specific antagonist, EGF inhibitor, EGFR inhibitors, Erbitux® (cetuximab, ImClone Systems, Inc., Branchburg, N.J.), Vectibix® (panitumumab, Amgen, Thousand Oaks, Calif.), TIE2 inhibitors, IGF1R inhibitors, COX-II (cyclooxygenase II) inhibitors, MMP-2 (matrix-metalloproteinase 2) inhibitors, and MMP-9 (matrix-metalloproteinase 9) inhibitors, CP-547,632 (Pfizer Inc., NY, USA), Axitinib (Pfizer Inc.; AG-013736), ZD-6474 (AstraZeneca), AEE788 (Novartis), AZD-2171), VEGF Trap (Regeneron/Aventis), Vatalanib (also known as PTK-787, ZK-222584: Novartis & Schering A G), Macugen (pegaptanib octasodium, NX-1838, EYE-001, Pfizer Inc./Gilead/Eyetech), IM862 (Cytran Inc. of Kirkland, Wash., USA); and angiozyme, a synthetic ribozyme from Ribozyme (Boulder, Colo.) and Chiron (Emeryville, Calif.) and combinations thereof. Other angiogenesis inhibitors include thrombospondin1, thrombospondin2, collagen IV and collagen XVIII. VEGF inhibitors are disclosed in U.S. Pat. Nos. 6,534,524 and 6,235,764, both of which are incorporated in their entirety for all purposes. Anti-angiogenic agents also include native angiogenesis inhibitors, e.g., angiostatin, endostatin, etc. See, e.g., Klagsbrun and D'Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12):1359-1364; Tonini et al. (2003) *Oncogene* 22:6549-6556 (e.g., Table 2 listing known antiangiogenic factors); and, Sato (2003) *Int. J. Clin. Oncol.* 8:200-206 (e.g., Table 1 listing anti-angiogenic agents used in clinical trials).

The term "anti-angiogenic therapy" refers to a therapy useful for inhibiting angiogenesis which comprises the administration of an anti-angiogenic agent.

The term "CD20 expressing cancer" as used herein refers to all cancers in which the cancer cells show an expression of the CD20 antigen. Preferably CD20 expressing cancer as used herein refers to lymphomas (preferably B-Cell Non-Hodgkin's lymphomas (NHL)) and lymphocytic leukemias. Such lymphomas and lymphocytic leukemias include e.g. a) follicular lymphomas, b) Small Non-Cleaved Cell Lymphomas/Burkitt's lymphoma (including endemic Burkitt's lymphoma, sporadic Burkitt's lymphoma and Non-Burkitt's lymphoma) c) marginal zone lymphomas (including extranodal marginal zone B cell lymphoma (Mucosa-associated lymphatic tissue lymphomas, MALT), nodal marginal zone B cell lymphoma and splenic marginal zone lymphoma), d) Mantle cell lymphoma (MCL), e) Large Cell Lymphoma (including B-cell diffuse large cell lymphoma (DLCL), Diffuse Mixed Cell Lymphoma, Immunoblastic Lymphoma, Primary Mediastinal B-Cell Lymphoma, Angiocentric Lymphoma-Pulmonary B-Cell Lymphoma) f) hairy cell leukemia, g) lymphocytic lymphoma, waldenstrom's macroglobulinemia, h) acute lymphocytic leukemia (ALL), chronic lymphocytic leukemia (CLL)/small lymphocytic lymphoma (SLL), B-cell prolymphocytic leukemia, i) plasma cell neoplasms, plasma cell myeloma, multiple myeloma, plasmacytoma j) Hodgkin's disease.

More preferably the CD20 expressing cancer is a B-Cell Non-Hodgkin's lymphoma (NHL). Especially the CD20 expressing cancer is a Mantle cell lymphoma (MCL), acute lymphocytic leukemia (ALL), chronic lymphocytic leukemia (CLL), B-cell diffuse large cell lymphoma (DLCL), Burkitt's lymphoma, hairy cell leukemia, follicular lymphoma, multiple myeloma, marginal zone lymphoma, post transplant lymphoproliferative disorder (PTLD), HIV associated lymphoma, waldenstrom's macroglobulinemia, or primary CNS lymphoma.

The term "cytotoxic agent" as used herein refers to a substance that inhibits or prevents a cellular function and/or causes cell death or destruction. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu), chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "toxin" is any substance capable of having a detrimental effect on the growth or proliferation of a cell.

A "chemotherapeutic agent" is a chemical compound useful in the treatment of cancer. Examples of chemotherapeutic agents include alkylating agents such as thiotepa and cyclophosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Nicolaou et al., *Angew. Chem Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); combretastatin; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®, Bristol-Myers Squibb Oncology, Princeton, N.J.), albumin-engineered nanoparticle formulation of paclitaxel (ABRAXANE™), and docetaxel (TAXOTERE®, Rhome-Poulene Rorer, Antony, France); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R) (e.g., erlotinib (Tarceva™)); and VEGF-A that reduce cell proliferation; vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors; tyrosine kinase inhibitors; serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin, and pharmaceutically acceptable salts, acids or derivatives of any of the above; as well as combinations of two or more of the above.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON.cndot.toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above; as well as combinations of two or more of the above.

A "growth inhibitory agent" when used herein refers to a compound or composition which inhibits growth of a cell either in vitro or in vivo. In one embodiment, growth inhibitory agent is growth inhibitory antibody that prevents or reduces proliferation of a cell expressing an antigen to which the antibody binds. In another embodiment, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

A "subject" or an "individual" for purposes of treatment refers to any animal classified as a mammal, including humans, domestic and farm animals, and zoo, sports, or pet animals, such as dogs, horses, cats, cows, etc. Preferably, the mammal is human.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "constant domain" refers to the portion of an immunoglobulin molecule having a more conserved amino acid sequence relative to the other portion of the immunoglobulin, the variable domain, which contains the antigen binding site. The constant domain contains the $C_H1$, $C_H2$ and $C_H3$ domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "$V_H$." The variable domain of the light chain may be referred to as "$V_L$." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any mammalian species can be assigned to one of two clearly distinct types, called kappa ("κ") and lambda ("λ"), based on the amino acid sequences of their constant domains.

The term IgG "isotype" or "subclass" as used herein is meant any of the subclasses of immunoglobulins defined by the chemical and antigenic characteristics of their constant regions.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, γ, ε, γ, and μ, respectively. The subunit structures and three-dimensional configurations of different classes of immunoglobulins are well known and described generally in, for example, Abbas et al. *Cellular and Mol. Immunology*, 4th ed. (W.B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. Examples of antibody fragments include Fab, Fab', $F(ab')_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, *Nature,* 256:495-97 (1975); Hongo et al., *Hybridoma,* 14 (3): 253-260 (1995); Harlow et al., *Antibodies: A Laboratory Manual,* (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATTZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227: 381 (1991); Marks et al., *J. Mol. Biol.,* 222:581 (1991). Also available for the preparation of human monoclonal antibodies are methods described in Cole et al., *Monoclonal Antibodies and Cancer Therapy,* Alan R. Liss, p. 77 (1985); Boerner et al., *J. Immunol.,* 147(1):86-95 (1991). See also van Dijk and van de Winkel, *Curr. Opin. Pharmacol.,* 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 103:3557-3562 (2006) regarding human antibodies generated via a human B-cell hybridoma technology.

A "species-dependent antibody" is one which has a stronger binding affinity for an antigen from a first mammalian species than it has for a homologue of that antigen from a second mammalian species. Normally, the species-dependent antibody "binds specifically" to a human antigen (e.g., has a binding affinity (Kd) value of no more than about $1\times10^{-7}$ M, preferably no more than about $1\times10^{-8}$M and preferably no more than about $1\times10^{-9}$M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but preferably is a humanized or human antibody.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The expression "linear antibodies" refers to the antibodies described in Zapata et al. (1995 *Protein Eng,* 8(10):1057-1062). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

II. Antibody Formulations and Preparation

The invention herein relates to stable aqueous formulations comprising an antibody. In some embodiments, the formulation comprises a monoclonal antibody, trehalose, and a buffer, wherein the weight ratio of the monoclonal antibody to the trehalose in the formulation is about 1.65 to about 4.95, and wherein the formulation has a pH of about 5.5 to about 7.0. In some embodiments, the formulation further comprises a buffer (such as sodium phosphate or histidine). In some embodiments, the formulation comprises (a) a monoclonal antibody in an amount of about 25 mg/mL to about 100 mg/mL; (b) trehalose in an amount of about 40 mM to about 120 mM; and (c) sodium phosphate in an amount of about 15 mM to about 35 mM, wherein said formulation has a pH of about 5.5 to about 7.0. In some embodiments, the antibody in the formulation is stable at −20° C. for at least about 6 months, at least about 12 months, or at least about 18 months.

A. Antibody Preparation

The antibody in the formulation is prepared using techniques available in the art for generating antibodies, exemplary methods of which are described in more detail in the following sections.

The antibody is directed against an antigen of interest. Preferably, the antigen is a biologically important polypeptide and administration of the antibody to a mammal suffering from a disorder can result in a therapeutic benefit in that mammal. However, antibodies directed against non-polypeptide antigens are also contemplated.

Where the antigen is a polypeptide, it may be a transmembrane molecule (e.g. receptor) or ligand such as a growth factor. Exemplary antigens include molecules such as vascular endothelial growth factor (VEGF); CD20; ox-LDL; ox-ApoB100; renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des (1-3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

In certain embodiments of the invention, the molecular targets for antibodies encompassed by the invention include VEGF and CD20. In some embodiments, the antibody herein is one which binds to human VEGF. In some embodiments, the antibody herein is one which binds to human CD20.

(i) Antigen Preparation

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

(ii) Certain Antibody-Based Methods

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies of the invention can be made using the hybridoma method first described by Kohler et al., *Nature*, 256:495 (1975), and further described, e.g., in Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981), and Ni, *Xiandai Mianyixue*, 26(4): 265-268 (2006) regarding human-human hybridomas. Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

For various other hybridoma techniques, see, e.g., US 2006/258841; US 2006/183887 (fully human antibodies), US 2006/059575; US 2005/287149; US 2005/100546; US 2005/026229; and U.S. Pat. Nos. 7,078,492 and 7,153,507. An exemplary protocol for producing monoclonal antibodies using the hybridoma method is described as follows. In one embodiment, a mouse or other appropriate host animal, such as a hamster, is immunized to elicit lymphocytes that produce or are capable of producing antibodies that will specifically bind to the protein used for immunization. Antibodies are raised in animals by multiple subcutaneous (sc) or intraperitoneal (ip) injections of a polypeptide of the invention or a fragment thereof, and an adjuvant, such as monophosphoryl lipid A (MPL)/trehalose dicrynomycolate (TDM) (Ribi Immunochem. Research, Inc., Hamilton, Mont.). A polypeptide of the invention (e.g., antigen) or a fragment thereof may be prepared using methods well known in the art, such as recombinant methods, some of which are further described herein. Serum from immunized animals is assayed for anti-antigen antibodies, and booster immunizations are optionally administered. Lymphocytes from animals producing anti-antigen antibodies are isolated. Alternatively, lymphocytes may be immunized in vitro.

Lymphocytes are then fused with myeloma cells using a suitable fusing agent, such as polyethylene glycol, to form a hybridoma cell. See, e.g., Goding, *Monoclonal Antibodies: Principles and Practice*, pp. 59-103 (Academic Press, 1986). Myeloma cells may be used that fuse efficiently, support stable high-level production of antibody by the selected antibody-producing cells, and are sensitive to a medium such as HAT medium. Exemplary myeloma cells include, but are not limited to, murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

The hybridoma cells thus prepared are seeded and grown in a suitable culture medium, e.g., a medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferably, serum-free hybridoma cell culture methods are used to reduce use of animal-derived serum such as fetal bovine serum, as described, for example, in Even et al., *Trends in Biotechnology*, 24(3), 105-108 (2006).

Oligopeptides as tools for improving productivity of hybridoma cell cultures are described in Franek, *Trends in Monoclonal Antibody Research*, 111-122 (2005). Specifically, standard culture media are enriched with certain amino acids (alanine, serine, asparagine, proline), or with protein hydrolyzate fractions, and apoptosis may be significantly suppressed by synthetic oligopeptides, constituted of three to six amino acid residues. The peptides are present at millimolar or higher concentrations.

Culture medium in which hybridoma cells are growing may be assayed for production of monoclonal antibodies that bind to an antibody of the invention. The binding specificity of monoclonal antibodies produced by hybridoma cells may be determined by immunoprecipitation or by an in vitro binding assay, such as radioimmunoassay (MA) or enzyme-linked immunoadsorbent assay (ELISA). The binding affinity of the monoclonal antibody can be determined, for example, by Scatchard analysis. See, e.g., Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods. See, e.g., Goding, supra. Suitable culture media for this purpose include, for example, D-MEM or RPMI-1640 medium. In addition, hybridoma cells may be grown in vivo as ascites tumors in an animal. Monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. One procedure for isolation of proteins from hybridoma cells is described in US 2005/176122 and U.S. Pat. No. 6,919,436. The method includes using minimal salts, such as lyotropic salts, in the binding process and preferably also using small amounts of organic solvents in the elution process.

(iii) Certain Library Screening Methods

Antibodies of the invention can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. in *Methods in Molecular Biology* 178:1-37 (O'Brien et al., ed., Human Press, Totowa, N.J., 2001). For example, one method of generating antibodies of interest is through the use of a phage antibody library as described in Lee et al., *J. Mol. Biol.* (2004), 340(5):1073-93.

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the antibodies of the invention can be obtained by designing a suitable antigen screening procedure to select for the phage clone of interest followed by construction of a full length antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda, Md. (1991), vols. 1-3.

In certain embodiments, the antigen-binding domain of an antibody is formed from two variable (V) regions of about 110 amino acids, one each from the light (VL) and heavy (VH) chains, that both present three hypervariable loops (HVRs) or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994). As used herein, scFv encoding phage clones and Fab encoding phage clones are collectively referred to as "Fv phage clones" or "Fv clones."

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

In certain embodiments, filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., *J. Mol. Biol.*, 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., *Nucl. Acids Res.*, 19: 4133-4137 (1991).

In general, nucleic acids encoding antibody gene fragments are obtained from immune cells harvested from humans or animals. If a library biased in favor of anti-antigen clones is desired, the subject is immunized with antigen to generate an antibody response, and spleen cells and/or circulating B cells other peripheral blood lymphocytes (PBLs) are recovered for library construction. In one embodiment, a human antibody gene fragment library biased in favor of anti-antigen clones is obtained by generating an anti-antigen antibody response in transgenic mice carrying a functional human immunoglobulin gene array (and lacking a functional endogenous antibody production system) such that antigen immunization gives rise to B cells producing human antibodies against antigen. The generation of human antibody-producing transgenic mice is described below.

Additional enrichment for anti-antigen reactive cell populations can be obtained by using a suitable screening procedure to isolate B cells expressing antigen-specific membrane bound antibody, e.g., by cell separation using antigen affinity chromatography or adsorption of cells to fluorochrome-labeled antigen followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which antigen is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci.* (USA), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature*, 341: 544-546 (1989). However, for amplifying from cDNA, back primers can also be based in the leader exon as described in Jones et al., *Biotechnol.*, 9: 88-89 (1991), and forward primers within the constant region as described in Sastry et al., *Proc. Natl. Acad. Sci.* (USA), 86: 5728-5732 (1989). To maximize complementarity, degeneracy can be incorporated in the primers as described in Orlandi et al. (1989) or Sastry et al. (1989). In certain embodiments, library diversity is maximized by using PCR primers targeted to each V-gene family in order to amplify all available VH and VL arrangements present in the immune cell nucleic acid sample, e.g. as described in the method of Marks et al., *J. Mol. Biol.*, 222: 581-597 (1991) or as described in the method of Orum et al., *Nucleic Acids Res.*, 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature*, 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.*, 227: 776-798 (1992)), and mapped (reported in Matsuda et al., *Nature Genet.*, 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.*, 227: 381-388 (1992). VH repertoires can also be made with all the sequence diversity focused in a long H3 loop of a single length as described in Barbas et al., *Proc. Natl. Acad. Sci. USA*, 89: 4457-4461 (1992). Human Vκ and Vλ segments have been cloned and sequenced (reported in Williams and Winter, *Eur. J. Immunol.*, 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.*, 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene*, 128: 119-126 (1993), or in vivo by combinatorial infection, e.g., the loxP system described in Waterhouse et al., *Nucl. Acids Res.*, 21: 2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$M).

Alternatively, the repertoires may be cloned sequentially into the same vector, e.g. as described in Barbas et al., *Proc. Natl. Acad. Sci. USA*, 88: 7978-7982 (1991), or assembled together by PCR and then cloned, e.g. as described in Clackson et al., *Nature*, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.*, 20: 3831-3837 (1992).

The antibodies produced by naive libraries (either natural or synthetic) can be of moderate affinity ($K_d^{-1}$ of about $10^6$ to $10^7$ $M^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., *Technique* 1: 11-15 (1989)) in the method of Hawkins et al., *J. Mol. Biol.*, 226: 889-896 (1992) or in the method of Gram et al., *Proc. Natl. Acad. Sci USA*, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.*, 10: 779-783 (1992). This technique allows the production of antibodies and antibody fragments with affinities of about $10^{-9}$M or less.

Screening of the libraries can be accomplished by various techniques known in the art. For example, antigen can be used to coat the wells of adsorption plates, expressed on host cells affixed to adsorption plates or used in cell sorting, or conjugated to biotin for capture with streptavidin-coated beads, or used in any other method for panning phage display libraries.

The phage library samples are contacted with immobilized antigen under conditions suitable for binding at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci USA*, 88: 7978-7982 (1991), or by alkali, e.g. as described in Marks et al., *J. Mol. Biol.*, 222: 581-597 (1991), or by antigen competition, e.g. in a procedure similar to the antigen competition method of Clackson et al., *Nature*, 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

It is possible to select between phage antibodies of different affinities, even with affinities that differ slightly, for antigen. However, random mutation of a selected antibody (e.g. as performed in some affinity maturation techniques) is likely to give rise to many mutants, most binding to antigen, and a few with higher affinity. With limiting antigen, rare high affinity phage could be competed out. To retain all higher affinity mutants, phages can be incubated with excess biotinylated antigen, but with the biotinylated antigen at a concentration of lower molarity than the target molar affinity constant for antigen. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-antigen clones may be selected based on activity. In certain embodiments, the invention provides anti-antigen antibodies that bind to living cells that naturally express antigen or bind to free floating antigen or antigen attached to other cellular structures. Fv clones corresponding to such anti-antigen antibodies can be selected by (1) isolating anti-antigen clones from a phage library as described above, and optionally amplifying the isolated population of phage clones by growing up the population in a suitable bacterial host; (2) selecting antigen and a second protein against which blocking and non-blocking activity, respectively, is desired; (3) adsorbing the anti-antigen phage clones to immobilized antigen; (4) using an excess of the second protein to elute any undesired clones that recognize antigen-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., *Curr. Opinion in Immunol.*, 5: 256 (1993) and Pluckthun, *Immunol. Revs*, 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. An Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In certain embodiments, an Fv clone derived from human variable DNA is fused to human constant region DNA to form coding sequence(s) for full- or partial-length human heavy and/or light chains.

DNA encoding anti-antigen antibody derived from a hybridoma of the invention can also be modified, for example, by substituting the coding sequence for human heavy- and light-chain constant domains in place of homologous murine sequences derived from the hybridoma clone (e.g. as in the method of Morrison et al., *Proc. Natl. Acad. Sci. USA*, 81: 6851-6855 (1984)). DNA encoding a hybridoma- or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

(iv) Humanized and Human Antibodies

Various methods for humanizing non-human antibodies are known in the art. For example, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to one embodiment of the method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human antibodies of the invention can be constructed by combining Fv clone variable domain sequence(s) selected from human-derived phage display libraries with known human constant domain sequence(s) as described above. Alternatively, human monoclonal antibodies of the invention can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).

It is possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al, *Proc. Natl. Acad. Sci. USA*, 90:2551 (1993); Jakobovits et al., *Nature*, 362:255-258 (1993); Bruggermann et al., *Year in Immuno.*, 7:33 (1993); and Duchosal et al. *Nature* 355:258 (1992).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

(v) Antibody Fragments

Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab)_2$ fragments (Carter et al., *Bio/Technology* 10:163-167 (1992)). According to another approach, $F(ab')_2$ fragments can be isolated directly from recombinant host cell culture. Fab and $F(ab')_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See *Antibody Engineering*, ed. Borrebaeck, supra. The antibody fragment may also be a "linear antibody", e.g., as described in U.S. Pat. No. 5,641,870, for example. Such linear antibodies may be monospecific or bispecific.

(vi) Multispecific Antibodies

Multispecific antibodies have binding specificities for at least two different epitopes, where the epitopes are usually from different antigens. While such molecules normally will only bind two different epitopes (i.e. bispecific antibodies, BsAbs), antibodies with additional specificities such as trispecific antibodies are encompassed by this expression when used herein. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is typical to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. One interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab)$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al, *J. Immunol,* 152:5368 (1994).

Antibodies with more than two valencies are contemplated. For example, trispecific antibodies can be prepared. Tuft et al. *J. Immunol.* 147: 60 (1991).

(vii) Single-Domain Antibodies

In some embodiments, an antibody of the invention is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

(viii) Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

(ix) Antibody Derivatives

The antibodies of the invention can be further modified to contain additional nonproteinaceous moieties that are known in the art and readily available. In certain embodiments, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

(x) Vectors, Host Cells, and Recombinant Methods

Antibodies may also be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(a) Signal Sequence Component

An antibody of the invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (e.g., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

(b) Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ, plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter.

(c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, etc.

For example, cells transformed with the DHFR gene are identified by culturing the transformants in a culture medium containing methotrexate (Mtx), a competitive antagonist of DHFR. Under these conditions, the DHFR gene is amplified along with any other co-transformed nucleic acid. A Chinese hamster ovary (CHO) cell line deficient in endogenous DHFR activity (e.g., ATCC CRL-9096) may be used.

Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of Kluyveromyces yeasts. Alternatively, an expression system for large-scale production of recombinant calf chymosin was reported for K. lactis. Van den Berg, Bio/Technology, 8:135 (1990). Stable multi-copy expression vectors for secretion of mature recombinant human serum albumin by industrial strains of Kluyveromyces have also been disclosed. Fleer et al., Bio/Technology, 9:968-975 (1991).

(d) Promoter Component

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding an antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(e) Enhancer Element Component

Transcription of a DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody-encoding sequence, but is preferably located at a site 5' from the promoter.

(f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein.

(g) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Envinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Full length antibody, antibody fusion proteins, and antibody fragments can be produced in bacteria, in particular when glycosylation and Fc effector function are not needed, such as when the therapeutic antibody is conjugated to a cytotoxic agent (e.g., a toxin) that by itself shows effectiveness in tumor cell destruction. Full length antibodies have greater half-life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, *Methods in Molecular Biology*, Vol. 248 (B. K. C. Lo, ed., Humana Press, Totowa, N.J., 2003), pp. 245-254, describing expression of antibody fragments in *E. coli*. After expression, the antibody may be isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as Schizosaccharomyces pombe; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*. For a review discussing the use of yeasts and filamentous fungi for the production of therapeutic proteins, see, e.g., Gerngross, *Nat. Biotech.* 22:1409-1414 (2004).

Certain fungi and yeast strains may be selected in which glycosylation pathways have been "humanized," resulting in the production of an antibody with a partially or fully human glycosylation pattern. See, e.g., Li et al., *Nat. Biotech.* 24:210-215 (2006) (describing humanization of the glycosylation pathway in *Pichia pastoris*); and Gerngross et al., supra.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frupperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of Autographa californica NPV and the Bm-5 strain of *Bombyx mori* NPV, and such viruses may be used as the virus herein according to the invention, particularly for transfection of *Spodoptera frupperda* cells.

Plant cell cultures of cotton, corn, potato, soybean, petunia, tomato, duckweed (Leninaceae), alfalfa (*M. truncatula*), and tobacco can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J., 2003), pp. 255-268.

Host cells are transformed with the above-described expression or cloning vectors for antibody production and cultured in conventional nutrient media modified as appropriate for inducing promoters, selecting transformants, or amplifying the genes encoding the desired sequences.

(h) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(xi) Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

In general, various methodologies for preparing antibodies for use in research, testing, and clinical are well-established in the art, consistent with the above-described methodologies and/or as deemed appropriate by one skilled in the art for a particular antibody of interest.

B. Selecting Biologically Active Antibodies

Antibodies produced as described above may be subjected to one or more "biological activity" assays to select an antibody with beneficial properties from a therapeutic perspective. The antibody may be screened for its ability to bind the antigen against which it was raised. For example, for an anti-VEGF antibody, the antigen binding properties of the antibody can be evaluated in an assay that detects the ability to bind to VEGF. In another example, for an anti-CD20 antibody, the antigen binding properties of the antibody can be evaluated in an assay that detects the ability to bind to CD20.

In another embodiment, the affinity of the antibody may be determined by saturation binding; ELISA; and/or competition assays (e.g. RIA's), for example.

Also, the antibody may be subjected to other biological activity assays, e.g., in order to evaluate its effectiveness as a therapeutic. Such assays are known in the art and depend on the target antigen and intended use for the antibody.

To screen for antibodies which bind to a particular epitope on the antigen of interest (e.g., those which block binding of the anti-VEGF antibody of the example to VEGF), a routine cross-blocking assay such as that described in *Antibodies, A Laboratory Manual*, Cold Spring Harbor Laboratory, Ed Harlow and David Lane (1988), can be performed. Alternatively, epitope mapping, e.g. as described in Champe et al., *J. Biol. Chem.* 270:1388-1394 (1995), can be performed to determine whether the antibody binds an epitope of interest.

The term "expression of the CD20" antigen is intended to indicate an significant level of expression of the CD20 antigen in a cell, preferably on the cell surface of a T- or B-Cell, more preferably a B-cell, from a tumor or cancer, respectively, preferably a non-solid tumor. Patients having a "CD20 expressing cancer" can be determined by standard assays known in the art. For example, CD20 antigen expression is measured using immunohistochemical (IHC) detection, FACS or via PCR-based detection of the corresponding mRNA.

C. Preparation of the Formulations

After preparation of the antibody of interest (e.g., techniques for producing antibodies which can be formulated as disclosed herein will be elaborated below and are known in the art), the pharmaceutical formulation comprising it is prepared. In certain embodiments, the antibody to be formulated has not been subjected to prior lyophilization and the formulation of interest herein is an aqueous formulation. In certain embodiments, the antibody is a full length antibody. In one embodiment, the antibody in the formulation is an antibody fragment, such as an $F(ab')_2$, in which case problems that may not occur for the full length antibody (such as clipping of the antibody to Fab) may need to be addressed. The therapeutically effective amount of antibody present in the formulation is determined by taking into account the desired dose volumes and mode(s) of administration, for example. From about 25 mg/mL to about 100 mg/mL, or from about 30 mg/mL to about 100 mg/mL or from about 45 mg/mL to about 55 mg/mL is an exemplary antibody concentration in the formulation.

An aqueous formulation is prepared comprising the antibody in a pH-buffered solution. The buffer of this invention has a pH in the range from about 5.5 to about 7.0. In certain embodiments the pH is in the range from pH 5.5 to 6.5, in the range from pH 5.7 to 6.8, in the range from pH 5.8 to 6.5, in the range from pH 5.9 to 6.5, in the range from pH 6.0 to 6.5, or in the range from pH 6.2 to 6.5. In certain embodiments of the invention, the formulation has a pH of 6.2 or about 6.2. In certain embodiments of the invention, the formulation has a pH of 6.0 or about 6.0. Examples of buffers that will control the pH within this range include sodium phosphate and histidine (such as L-histidine). In certain embodiments, the buffer contains sodium phosphate in the concentration of about 15 mM to about 35 mM. In certain embodiments of the invention, the buffer contains sodium phosphate in the concentration of about 20 mM to about 30 mM, about 22 mM to about 28 mM, or about 25 mM. In one embodiment, the buffer is sodium phosphate in an amount of about 25 mM, pH 6.2. In certain embodiments, the buffer contains histidine in the concentration of about 15 mM to about 35 mM. In certain embodiments of the invention, the buffer contains histidine in the concentration of about 20 mM to about 30 mM, about 22 mM to about 28 mM, or about 25 mM. In one embodiment, the buffer is histidine in an amount of about 20 mM, pH 6.0.

The formulation further comprises trehalose in an amount of about 40 mM to about 120 mM. In some embodiments, the trehalose in the formulation is about 40 mM to about 100 mM, about 40 mM to about 90 mM, about 40 mM to about 80 mM, about 50 mM to about 70 mM, or about 55 mM to about 65 mM. In some embodiments, the trehalose in the formulation is about 40 mM, about 50 mM, about 60 mM, about 70 mM, about 80 mM, about 90 mM, about 100 mM, about 110 mM, or about 120 mM.

In some embodiments, the weight ratio of the monoclonal antibody to trehalose in the formulation is about 1.65 to about 4.95. In some embodiments, the weight ratio of the monoclonal antibody to trehalose in the formulation is about 1.65 to about 3.30. In some embodiments, the weight ratio of the monoclonal antibody to the trehalose is about 1.70 to about 2.91. In some embodiments, the weight ratio of the monoclonal antibody to the trehalose is about 2.00 to about 3.30. In some embodiments, the weight ratio of the monoclonal antibody to the trehalose is about any of 1.65, 1.70, 1.80, 1.90, 2.00, 2.08, 2.10, 2.20, 2.30, 2.31, 2.38, 2.40, 2.48, 2.50, 2.60, 2.70, 2.80, 2.90, 2.91, 3.00, 3.10, 3.20, 3.30, 3.40, 3.50, 3.70, 3.80, 3.90, 4.00, 4.10, 4.20, 4.30, 4.40, 4.50, 4.60, 4.70, 4.80, 4.90, and 4.95, including every value in between these numbers. As used herein, the weight of trehalose in the formulation for calculating the weight ratio of the antibody to the trehalose is based on the amount trehalose dihydrate (MW 378.33). If other forms of trehalose (e.g., trehalose anhydrous) are used, the weight of the trehalose in the formulation should be converted to the weight of trehalose dihydrate with the same molar concentration.

A surfactant can optionally be added to the antibody formulation. Exemplary surfactants include nonionic surfactants such as polysorbates (e.g. polysorbates 20, 80 etc) or poloxamers (e.g. poloxamer 188, etc.). The amount of surfactant added is such that it reduces aggregation of the formulated antibody and/or minimizes the formation of particulates in the formulation and/or reduces adsorption. For example, the surfactant may be present in the formulation in an amount from about 0.001% to about 0.5%, from about 0.005% to about 0.2%, from about 0.01% to about 0.1%, or from about 0.02% to about 0.06%, or about 0.03% to about 0.05%. In certain embodiments, the surfactant is present in the formulation in an amount of 0.04% or about 0.04%. In certain embodiments, the surfactant is present in the formulation in an amount of 0.02% or about 0.02%. In one embodiment, the formulation does not comprise a surfactant.

In one embodiment, the formulation contains the above-identified agents (e.g., antibody, buffer, trehalose, and/or surfactant) and is essentially free of one or more preservatives, such as benzyl alcohol, phenol, m-cresol, chlorobutanol and benzethonium Cl. In another embodiment, a preservative may be included in the formulation, particularly where the formulation is a multidose formulation. The concentration of preservative may be in the range from about 0.1% to about 2%, preferably from about 0.5% to about 1%. One or more other pharmaceutically acceptable carriers, excipients or stabilizers such as those described in Remington's Pharmaceutical Sciences 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; anti-oxidants including ascorbic acid and methionine; chelating agents such as EDTA; metal complexes (e.g. Zn-protein complexes); biodegradable polymers such as polyesters; and/or salt-forming counterions. Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

While the various descriptions of chelators herein often focus on EDTA, it will be appreciated that other metal ion chelators are also encompassed within the invention. Metal ion chelators are well known by those of skill in the art and include, but are not necessarily limited to aminopolycarboxylates, EDTA (ethylenediaminetetraacetic acid), EGTA (ethylene glycol-bis(beta-aminoethyl ether)-N,N,N',N'-tetraacetic acid), NTA (nitrilotriacetic acid), EDDS (ethylene diamine disuccinate), PDTA (1,3-propylenediaminetetraacetic acid), DTPA (diethylenetriaminepentaacetic acid), ADA (beta-alaninediacetic acid), MGCA (methylglycinediacetic acid), etc. Additionally, some embodiments herein comprise phosphonates/phosphonic acid chelators.

The formulation herein may also contain more than one protein as necessary for the particular indication being treated, preferably those with complementary activities that do not adversely affect the other protein. For example, where the antibody is anti-VEGF, it may be combined with another agent (e.g., a chemotherapeutic agent, and anti-neoplastic agent).

In some embodiments, the physical stability, chemical stability, or biological activity of the antibody in the formulation is evaluated or measured. Any methods known the art may be used to evaluate the stability and biological activity. In some embodiments, the antibody in the formulation is stable at −20° C. for at least about 12 months, at least about 18 months, at least about 21 months, or at least about 24 months (or at least about 52 weeks). In some embodiments, the stability is measured by the formation of high molecular weight species (HMWS) in the formulation after storage. In some embodiments, the percent of HMWS in the formulation is less than any of about 0.8%, about 0.9%, or about 1% after storage at −20° C. for at least about 6 months, at least about 12 months, at least about 18 months, or at least about 24 months. In some embodiments, the total aggregates in the formulation is less than any of about 2.5%, or about 3% after storage at −20° C. for at least about 6 months, at least about 12 months, at least about 18 months, or at least about 24 months.

The formulations to be used for in vivo administration should be sterile. This is readily accomplished by filtration through sterile filtration membranes, prior to, or following, preparation of the formulation.

III. Administration of Antibody Formulations

The formulation is administered to a mammal in need of treatment with the antibody, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In one embodiment, the formulation is administered to the mammal by intravenous administration. For such purposes, the formulation may be injected using a syringe or via an IV line, for example. In one embodiment, the formulation is administered to the mammal by subcutaneous administration.

The appropriate dosage ("therapeutically effective amount") of the antibody will depend, for example, on the condition to be treated, the severity and course of the condition, whether the antibody is administered for preventive or therapeutic purposes, previous therapy, the patient's clinical history and response to the antibody, the type of antibody used, and the discretion of the attending physician. The antibody is suitably administered to the patient at one time or over a series of treatments and may be administered to the patient at any time from diagnosis onwards. The antibody may be administered as the sole treatment or in conjunction with other drugs or therapies useful in treating the condition in question.

As a general proposition, the therapeutically effective amount of the antibody administered will be in the range of about 0.1 to about 50 mg/kg of patient body weight whether by one or more administrations, with the typical range of antibody used being about 0.3 to about 20 mg/kg, preferably about 0.3 to about 15 mg/kg, administered daily, for example. However, other dosage regimens may be useful. In one embodiment, the antagonist is an anti-VEGF antibody that is administered at a dose of about 100 or 400 mg every 1, 2, 3, or 4 weeks or is administered a dose of about 1, 3, 5, 7.5, 10, 15, or 20 mg/kg every 1, 2, 3, or 4 weeks. The dose may be administered as a single dose or as multiple doses (e.g., 2 or 3 doses), such as infusions. The progress of this therapy is easily monitored by conventional techniques.

IV. Articles of Manufacture

In another embodiment of the invention, an article of manufacture is provided comprising a container which holds the aqueous pharmaceutical formulation of the invention and optionally provides instructions for its use. Suitable containers include, for example, bottles, vials and syringes. The container may be formed from a variety of materials such as glass or plastic. An exemplary container is a 3-20 cc single use glass vial. Alternatively, for a multidose formulation, the container may be 3-100 cc glass vial. The container holds the formulation and the label on, or associated with, the container may indicate directions for use. The article of manufacture may further include other materials desirable from a commercial and user standpoint, including other buffers, diluents, filters, needles, syringes, and package inserts with instructions for use.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1

Development of Stable Bevacizumab Liquid Formulations

Various formulations comprising bevacizumab at protein concentrations in the range from about 25 mg/mL-100 mg/mL, sodium phosphate at a concentration of 25 mM or 51 mM, and trehalose at a concentration in the range from about 40 mM-240 mM were each tested for the formation of high molecular weight species (HMWS) when stored for 24 months at a temperature of −20° C. or −40° C. Prior to measurement for HMWS, the formulation solutions were either stressed or not stressed. The stressed conditions were those formulations that were subjected to accelerated aggregation conditions to crystallize trehalose. The results demonstrated that formulation A (termed "$F_A$") of bevacizumab (25 mg/mL bevacizumab, 51 mM sodium phosphate, 159 mM trehalose, 0.04% PS20, pH 6.2) started to aggregate when stored at −20° C. but not at −40° C. (FIG. 1). Notably, decreasing the concentration of trehalose while keeping the protein concentration constant at 25 mg/mL decreased aggregate formation when the formulation was stored at −20° C. (FIG. 1). Similar results were observed when the protein concentration was increased and the concentration of the sodium phosphate and trehalose was kept constant or was decreased as was the case for bevacizumab formulation B (termed "$F_B$"; 50 mg/mL bevacizumab, 25 mM sodium phosphate, 60 mM trehalose, 0.04% PS20, pH 6.2) (FIG. 1; empty circle). These results demonstrate that bevacizumab formulations with a higher concentration of protein relative to concentrations of trehalose can decrease trailing edge dimer (TED) and soluble aggregate.

Figure 2:
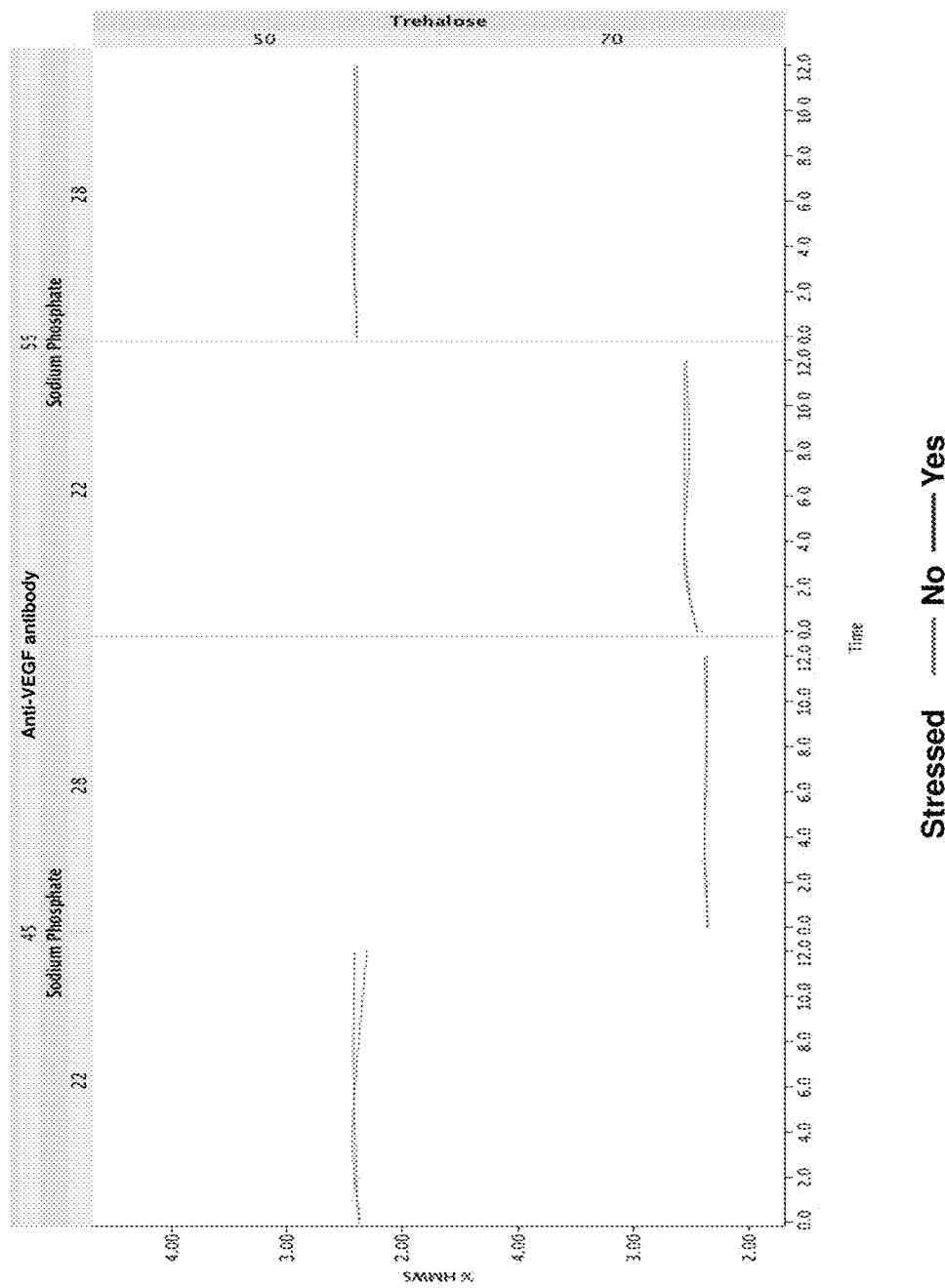
FIG. 2 is a graph depicting robust bevacizumab formulations that are resistant to formation of high molecular weight species despite undergoing accelerated aggregation conditions.

Notably, the $F_B$ formulation appeared to be in a robust formulation region. To ensure manufacturing robustness of the $F_B$ formulation, a 10% range of the various variables were tested by generating formulations comprising bevacizumab at protein concentrations in the range from about 45 mg/mL-55 mg/mL, sodium phosphate at a concentration in the range from about 22 mM-28 mM, and trehalose at a concentration in the range from about 50 mM-70 mM in a fill volume of 5 mL in 15 cc vials (Table 2). All formulations had a pH of 6.2 with 0.04% PS20. Each formulation was tested for the formation of HMWS when stored for 12 months at a temperature of −20° C. Prior to measurement for HMWS, formulation solutions were stressed in order to accelerate aggregation conditions to crystallize trehalose, and were compared to formulation solutions that were not stressed. Size exclusion chromatography (SEC) was used for aggregate formation analysis of the formulations at 1, 2, 3, 6, and 12 months of storage at −20° C. The results show that the tested formulation solutions did not aggregate when stored at −20° C. for 12 months. This demonstrated that the $F_B$ formulation was in a robust formulation region that effectively mitigated TED and soluble aggregate levels (FIG. 2).

TABLE 2

Formulations for robustness study

| Formulation | Bevacizumab (mg/mL) | Sodium phosphate (mM) | Trehalose (mM) | Protein/ Trehalose Weight Ratio* |
|---|---|---|---|---|
| $F_B$ | 50 | 25 | 60 | 2.20 |
| 1 | 45 | 22 | 50 | 2.38 |
| 2 | 55 | 22 | 70 | 2.08 |
| 3 | 45 | 28 | 70 | 1.70 |
| 4 | 55 | 28 | 50 | 2.91 |

*Trehalose dihydrate (MW 378.33) was used to make the formulation.

Figure 3A:
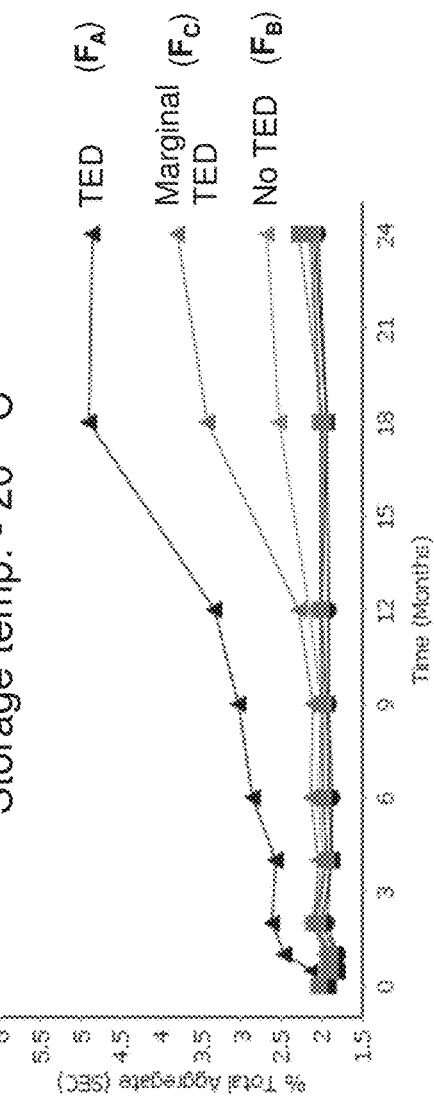
FIGS. 3A and 3B are graphs demonstrating reduced formation of high molecular weight species in bevacizumab formulations when stored for 24 months.
Figure 3B:
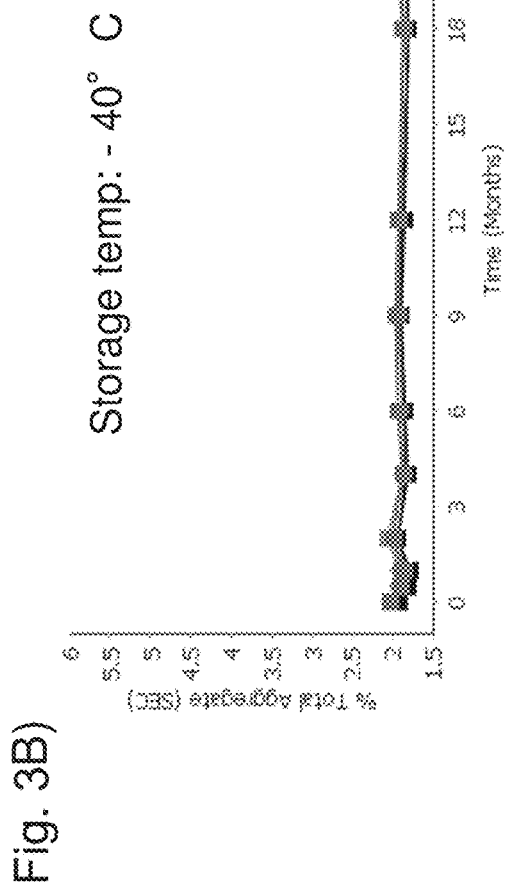
Figure 4:
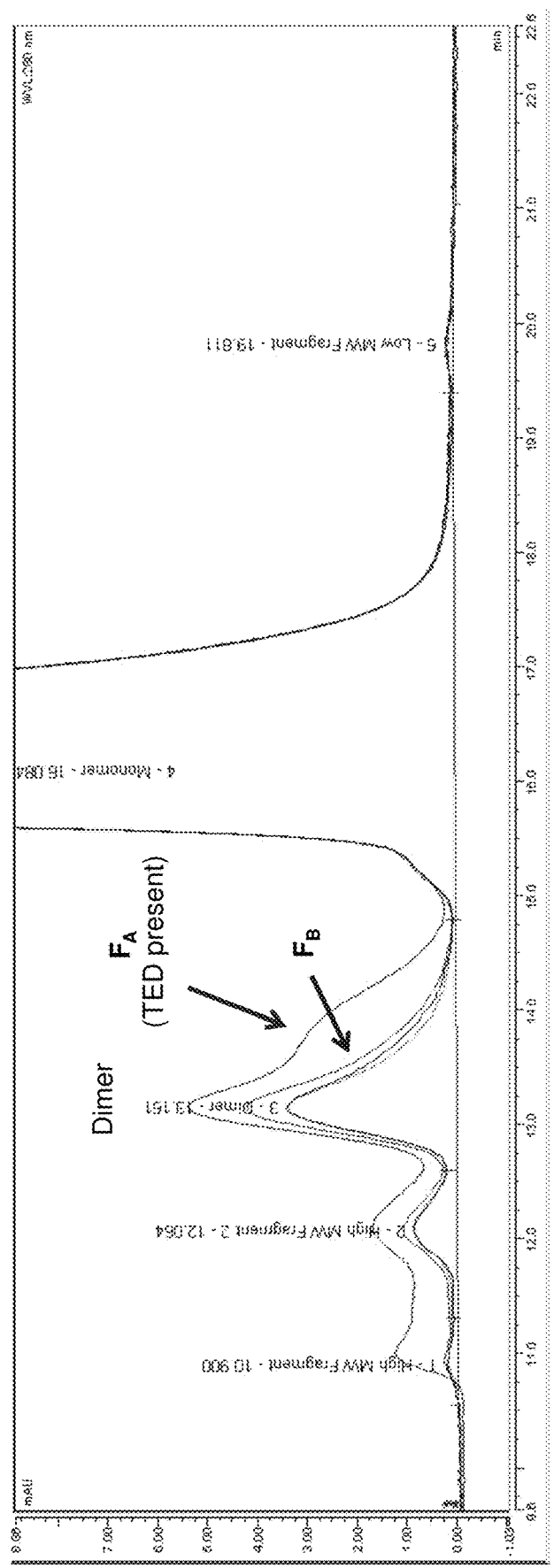
FIG. 4 is a size exclusion column chromatogram demonstrating the absence of trailing edge dimer (TED) formation in bevacizumab formulation B ($F_B$) when stored for 24 months as compared to formulation A ($F_A$) that contains a peak indicative of TED formation (arrow).

Additional stability assays were conducted with the $F_A$ formulation and the $F_B$ formulation as well as an alternate formulation ($F_C$) comprising 33 mg/mL bevacizumab, 25 mM sodium phosphate, and 60 mM trehalose. All formulations had a pH of 6.2 with 0.04% PS20. Each formulation was tested for the formation of HMWS when stored for 24 months at a temperature of −20° C. or −40° C. Prior to measurement for HMWS, formulation solutions were stressed in order to accelerate aggregation conditions by using an aggregation inducing technique (FIG. 3; closed triangle) to crystallize trehalose, and were compared to formulation solutions that were not stressed (FIG. 3; closed square). The formulations solutions were subjected to the dilute SEC method. After storage at 1 month, the dilute SEC method indicated an increase in aggregate levels for the $F_A$ formulation when stressed to accelerate aggregation (FIG. 3A). In comparison, the aggregate formation in the $F_B$ formulation was delayed to about 12 months when stressed. In addition, storage at −40° C. appeared to prevent any increase in total aggregate formation for all solutions tested (FIG. 3B). SEC chromatography demonstrated an increased presence of TED in the $F_A$ formulation as compared to the $F_B$ formulation after 24 months of storage at −20° C. (FIG. 4; arrows).

Example 2

Development of Stable Obinutuzumab Liquid Formulations

Various formulations comprising obinutuzumab at protein concentrations in the range from about 35 mg/mL-75 mg/mL, L-histidine at a concentration of 20 mM, poloxamer 188 at a concentration of 0.02% (w/v), trehalose at a concentration in the range from about 40 mM-240 mM, and pH 6.0, were each tested for the formation of high molecular weight species (HMWS) when stored for up to 52 weeks at a temperature of −20° C. or for up to 52 weeks at −40° C. See Table 3.

TABLE 3

Obinutuzumab Formulations

| Formulation | Obinutuzumab (mg/mL) | Trehalose (mM) | L-Histidine (mM) | Poloxamer 188 % (w/v) | Protein/ Trehalose Weight Ratio* |
|---|---|---|---|---|---|
| F2 | 35 | 160 | 20 | 0.02 | 0.58 |
| F3 | 35 | 120 | 20 | 0.02 | 0.77 |
| F4 | 35 | 80 | 20 | 0.02 | 1.16 |
| F5 | 35 | 40 | 20 | 0.02 | 2.31 |
| F6 | 50 | 240 | 20 | 0.02 | 0.55 |
| F7 | 50 | 120 | 20 | 0.02 | 1.10 |
| F8 | 50 | 80 | 20 | 0.02 | 1.65 |
| F9 | 50 | 40 | 20 | 0.02 | 3.30 |
| F10 | 75 | 80 | 20 | 0.02 | 2.48 |
| F11 | 75 | 40 | 20 | 0.02 | 4.95 |

*Trehalose dihydrate (MW 378.33) was used to make the formulation.

Prior to long term storage at −20° C. and −40° C., the formulation solutions were stressed by subjecting the frozen formulations to accelerated conditions to crystallize trehalose. At each analysis time point aliquots of each formulation were removed from storage, thawed and submitted to HMWS analysis by size exclusion chromatography. The results from size exclusion analysis demonstrated that several formulations of obinutuzumab showed an increase in HMWS content when stored at −20° C. but no aggregation over time was observed at −40° C. (FIGS. 5A and 5B and FIG. 6).

Figure 5A:
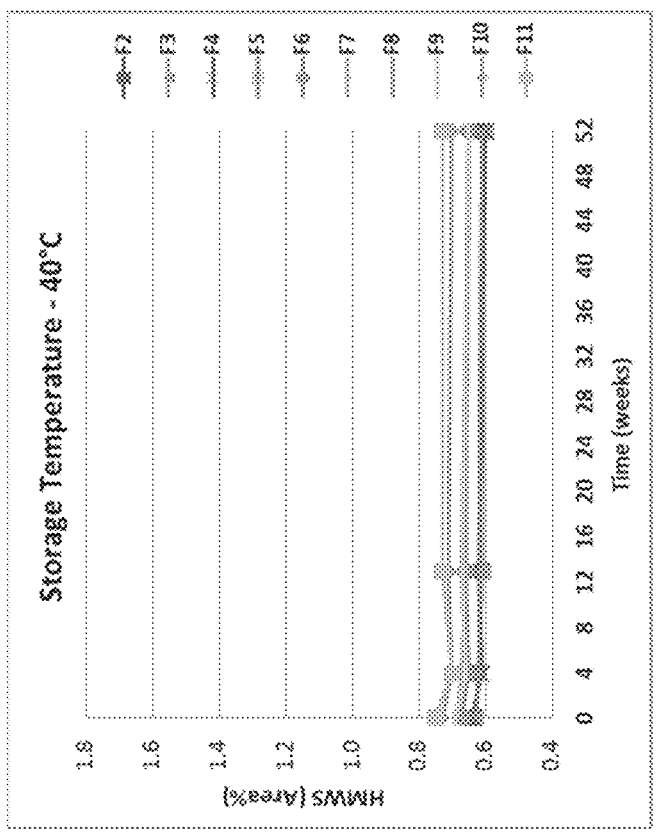
FIGS. 5A and 5B are graphs showing the formation of high molecular weight species (HMWS) in obinutuzumab formulations containing different antibody/trehalose ratios when stored below 0° C. under accelerated aggregation conditions.
Figure 5B:
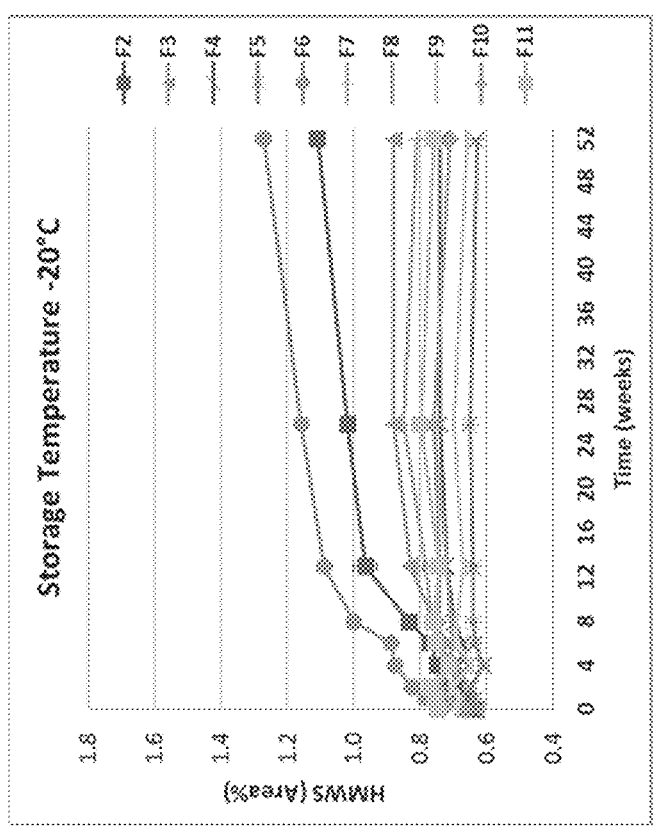
Figure 6:
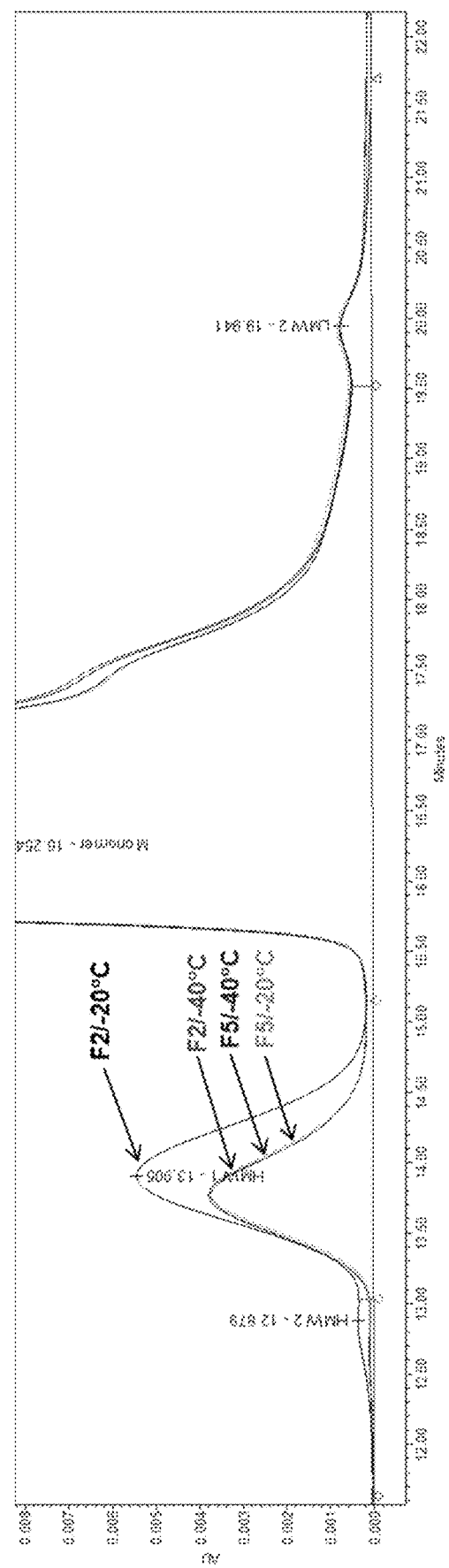
FIG. 6 shows examples of size exclusion chromatograms of selected obinutuzumab formulations stored below 0° C. for 52 weeks. F2: 35 mg/mL obinutuzumab, 160 mM trehalose; F5: 35 mg/mL obinutuzumab, 40 mM trehalose.

Reduction or even prevention of aggregate formation at 52 week at −20° C. was achieved when the protein concentration was increased and the concentration of trehalose was decreased as shown by obinutuzumab formulations F2-F5 and F6-F11 (FIG. 5A).

Figure 7B:
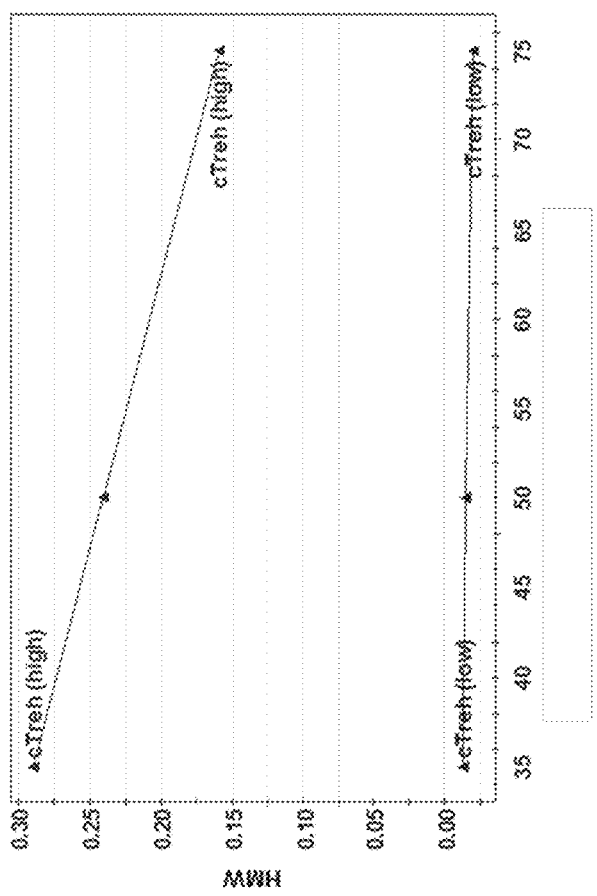
FIGS. 7A-7C show results of Multiple linear regression (MLR) analysis of the obinutuzumab data set at −20° C. storage.
Figure 7A:
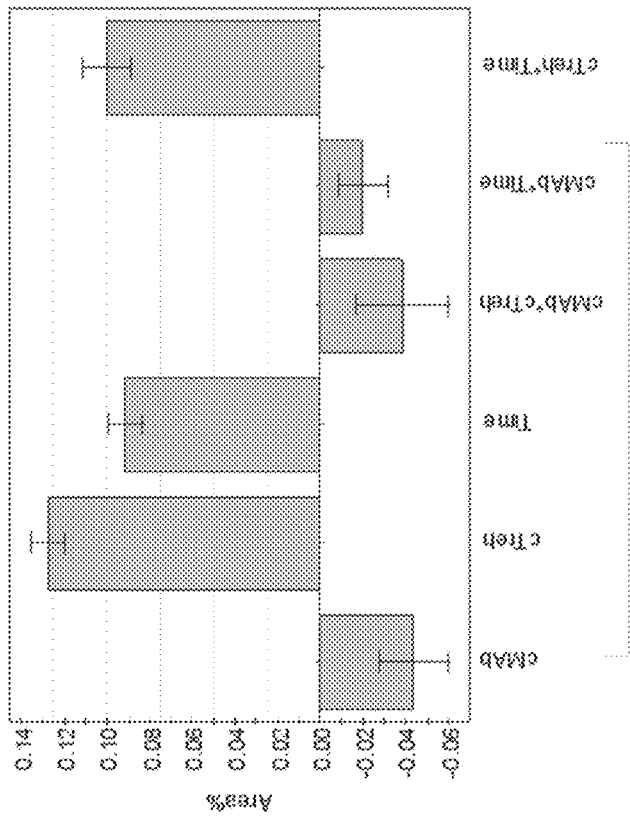
Figure 7C:
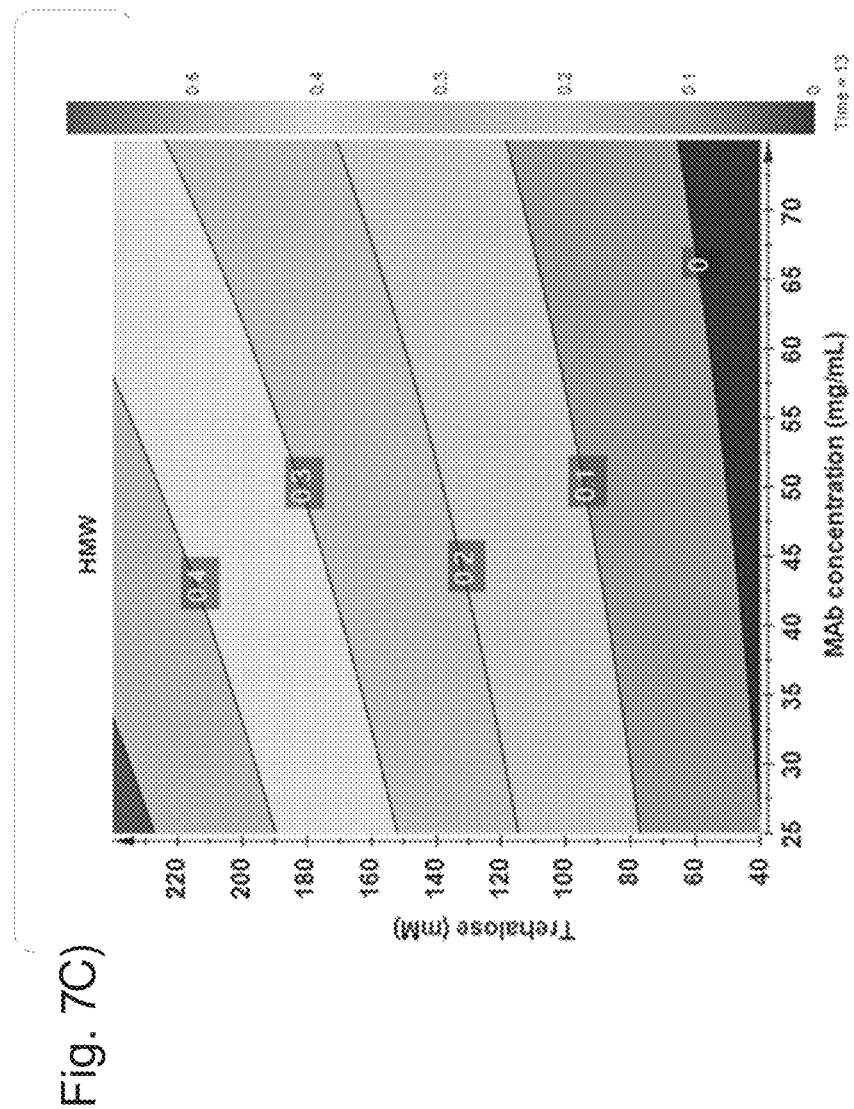

An increase in antibody concentration leads to a decrease in HMWS formation, whereas an increase in trehalose concentration increases HMWS formation over time. FIG. 7 shows that the effect of trehalose concentration on aggregate formation at −20° C. is more significant at low antibody concentration than at high antibody concentration. As the data are in a DoE (multi-factored design) format (2 formulation factors+time), multiple linear regression (MLR) can be used to estimate the effect of the different parameters. MLR analysis results in a regression model for high molecular weight species (HMWS) with an R2 of 0.968 showing a very good model fit and a high Q2 of 0.957 as a measure of good prediction precision. The resulting coefficient plot (FIG. 7A) displays the respective regression coefficients of the fitted model with confidence intervals which can be used to interpret the influence of the different factors. Statistically significant coefficients are (apart from time) both formulation factors cMAb (obinutuzumab concentration) and cTreh (trehalose concentration). As the cTre coefficient is much larger than the cMAb and the time coefficient trehalose concentration can be considered as the most important factor. The opposite orientation of the coefficient bars cMAb and cTreh show that an increase in antibody concentration leads to a decrease in HMWS formation, whereas an increase in trehalose concentration will increase HMWS formation over time. Furthermore the model includes the significant two-factor interaction term cMAb*cTreh (FIG. 7B) showing that the effect of trehalose concentration on aggregate formation at −20° C. is more significant at low antibody concentration than at high antibody concentration. FIG. 7C shows a response contour plot created with the factors cMAb and cTreh as axes, and time fixed at its high level.

These results demonstrate that obinutuzumab formulations with a higher concentration of protein relative to concentrations of trehalose have a decreased risk of soluble aggregate and trailing edge dimer (TED) formation when the formulation is stored at −20° C.

SEQUENCE LISTING

```
<210>   1
<211>   112
<212>   PRT
<213>   Mus sp.

<220>
<221>   MISC_FEATURE
<223>   amino acid sequence of variable region of the heavy chain (VH) of
        murine monoclonal anti-CD20 antibody B-Ly1

<400>   1

Gly Pro Glu Leu Val Lys Pro Gly Ala Ser Val Lys Ile Ser Cys Lys
1               5                   10                  15

Ala Ser Gly Tyr Ala Phe Ser Tyr Ser Trp Met Asn Trp Val Lys Leu
            20                  25                  30

Arg Pro Gly Gln Gly Leu Glu Trp Ile Gly Arg Ile Phe Pro Gly Asp
        35                  40                  45

Gly Asp Thr Asp Tyr Asn Gly Lys Phe Lys Gly Lys Ala Thr Leu Thr
    50                  55                  60

Ala Asp Lys Ser Ser Asn Thr Ala Tyr Met Gln Leu Thr Ser Leu Thr
65                  70                  75                  80

Ser Val Asp Ser Ala Val Tyr Leu Cys Ala Arg Asn Val Phe Asp Gly
                85                  90                  95

Tyr Trp Leu Val Tyr Trp Gly Gln Gly Thr Leu Val Thr Val Ser Ala
            100                 105                 110

<210>   2
<211>   103
<212>   PRT
<213>   Mus sp.

<220>
<221>   MISC_FEATURE
<223>   amino acid sequence of variable region of the light chain (VL) of
        murine monoclonal anti-CD20 antibody B-Ly1

<400>   2

Asn Pro Val Thr Leu Gly Thr Ser Ala Ser Ile Ser Cys Arg Ser Ser
1               5                   10                  15

Lys Ser Leu Leu His Ser Asn Gly Ile Thr Tyr Leu Tyr Trp Tyr Leu
            20                  25                  30

Gln Lys Pro Gly Gln Ser Pro Gln Leu Leu Ile Tyr Gln Met Ser Asn
            35                  40                  45

Leu Val Ser Gly Val Pro Asp Arg Phe Ser Ser Ser Gly Ser Gly Thr
    50                  55                  60

Asp Phe Thr Leu Arg Ile Ser Arg Val Glu Ala Glu Asp Val Gly Val
65                  70                  75                  80

Tyr Tyr Cys Ala Gln Asn Leu Glu Leu Pro Tyr Thr Phe Gly Gly Gly
                85                  90                  95

Thr Lys Leu Glu Ile Lys Arg
                100

<210>   3
<211>   119
<212>   PRT
<213>   Artificial
```

SEQUENCE LISTING

<220>
<223>   amino acid sequences of variable region of the heavy chain (VH) of humanized B-Ly1 antibody (B-HH2)

<400>   3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
            115

<210>   4
<211>   119
<212>   PRT
<213>   Artificial

<220>
<223>   amino acid sequences of variable region of the heavy chain (VH) of humanized B-Ly1 antibody (B-HH3)

<400>   4

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Leu Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
            115

<210>   5
<211>   119
<212>   PRT
<213>   Artificial

<220>
<223>   amino acid sequences of variable region of the heavy chain (VH) of humanized B-Ly1 antibody (B-HH4)

<400>   5

Gln Val Gln Leu Val Gln Ser Gly Ala Glu Val Lys Lys Pro Gly Ala

SEQUENCE LISTING

```
                1               5                   10                  15
Ser Val Lys Val Ser Cys Lys Val Ser Gly Tyr Ala Phe Ser Tyr Ser
                    20                  25                  30
Trp Met Asn Trp Val Arg Gln Ala Pro Gly Gln Gly Leu Glu Trp Met
                    35                  40                  45
Gly Arg Ile Phe Pro Gly Asp Gly Asp Thr Asp Tyr Asn Gly Lys Phe
                50                  55                  60
Lys Gly Arg Val Thr Ile Thr Ala Asp Lys Ser Thr Ser Thr Ala Tyr
65                      70                  75                  80
Met Glu Leu Ser Ser Leu Arg Ser Glu Asp Thr Ala Val Tyr Tyr Cys
                    85                  90                  95
Ala Arg Asn Val Phe Asp Gly Tyr Trp Leu Val Tyr Trp Gly Gln Gly
                    100                 105                 110
Thr Leu Val Thr Val Ser Ser
            115
```

<210>  6
<211>  119
<212>  PRT
<213>  Artificial

<220>
<223>  amino acid sequences of variable region of the heavy chain (VH) of humanized B-Ly1 antibody (B-HH5)

<400>  6

```
Gln Val Gln Leu Val Gln Ser Gly Ala Glu Val Lys Lys Pro Gly Ser
1               5                   10                  15
Ser Val Lys Val Ser Cys Lys Ala Ser Gly Tyr Ala Phe Ser Tyr Ser
                    20                  25                  30
Trp Met Ser Trp Val Arg Gln Ala Pro Gly Gln Gly Leu Glu Trp Met
                    35                  40                  45
Gly Arg Ile Phe Pro Gly Asp Gly Asp Thr Asp Tyr Asn Gly Lys Phe
                50                  55                  60
Lys Gly Arg Val Thr Ile Thr Ala Asp Lys Ser Thr Ser Thr Ala Tyr
65                      70                  75                  80
Met Glu Leu Ser Ser Leu Arg Ser Glu Asp Thr Ala Val Tyr Tyr Cys
                    85                  90                  95
Ala Arg Asn Val Phe Asp Gly Tyr Trp Leu Val Tyr Trp Gly Gln Gly
                    100                 105                 110
Thr Leu Val Thr Val Ser Ser
            115
```

<210>  7
<211>  119
<212>  PRT
<213>  Artificial

<220>
<223>  amino acid sequences of variable region of the heavy chain (VH) of humanized B-Ly1 antibody (B-HH6)

<400>  7

```
Gln Val Gln Leu Val Gln Ser Gly Ala Glu Val Lys Lys Pro Gly Ser
1               5                   10                  15
Ser Val Lys Val Ser Cys Lys Ala Ser Gly Tyr Ala Phe Ser Tyr Ser
                    20                  25                  30
Trp Ile Asn Trp Val Arg Gln Ala Pro Gly Gln Gly Leu Glu Trp Met
                    35                  40                  45
```

```
Gly Arg Ile Phe Pro Gly Asp Gly Asp Thr Asp Tyr Asn Gly Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
                100                 105                 110

Thr Leu Val Thr Val Ser Ser
        115

<210>   8
<211>   119
<212>   PRT
<213>   Artificial

<220>
<223>   amino acid sequences of variable region of the heavy chain (VH)
        of humanized B-Ly1 antibody (B-HH7)

<400>   8

Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Ala Phe Ser Tyr Ser
                 20                  25                  30

Trp Ile Ser Trp Val Arg Gln Ala Pro Gly Gln Gly Leu Glu Trp Met
             35                  40                  45

Gly Arg Ile Phe Pro Gly Asp Gly Asp Thr Asp Tyr Asn Gly Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
                100                 105                 110

Thr Leu Val Thr Val Ser Ser
        115

<210>   9
<211>   119
<212>   PRT
<213>   Artificial

<220>
<223>   amino acid sequences of variable region of the heavy chain (VH)
        of humanized B-Ly1 antibody (B-HH8)

<400>   9

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Tyr Ser
                 20                  25                  30

Trp Met Asn Trp Val Arg Gln Ala Pro Gly Gln Gly Leu Glu Trp Met
             35                  40                  45

Gly Arg Ile Phe Pro Gly Asp Gly Asp Thr Asp Tyr Asn Gly Lys Phe
 50                  55                  60

Lys Gly Arg Val Thr Ile Thr Ala Asp Lys Ser Thr Ser Thr Ala Tyr
 65                  70                  75                  80
```

Met Glu Leu Ser Ser Leu Arg Ser Glu Asp Thr Ala Val Tyr Tyr Cys
            85                  90                  95

Ala Arg Asn Val Phe Asp Gly Tyr Trp Leu Val Tyr Trp Gly Gln Gly
            100                 105                 110

Thr Leu Val Thr Val Ser Ser
            115

<210> 10
<211> 119
<212> PRT
<213> Artificial

<220>
<223> amino acid sequences of variable region of the heavy chain (VH)
      of humanized B-Ly1 antibody (B-HH9)

<400> 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Tyr Ser
            20                  25                  30

Trp Met Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asn Val Phe Asp Gly Tyr Trp Leu Val Tyr Trp Gly Gln Gly
            100                 105                 110

Thr Leu Val Thr Val Ser Ser
            115

<210> 11
<211> 119
<212> PRT
<213> Artificial

<220>
<223> amino acid sequences of variable region of the heavy chain (VH)
      of humanized B-Ly1 antibody (B-HL8)

<400> 11

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Val
            35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asn Val Phe Asp Gly Tyr Trp Leu Val Tyr Trp Gly Gln Gly
            100                 105                 110

Thr Leu Val Thr Val Ser Ser

SEQUENCE LISTING

```
           115

<210>      12
<211>      119
<212>      PRT
<213>      Artificial

<220>
<223>      amino acid sequences of variable region of the heavy chain (VH)
           of humanized B-Ly1 antibody (B-HL10)

<400>      12
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Tyr Ser
            20                  25                  30

Trp Met Asn Trp Val Arg Gln Ala Pro Gly Lys Gly Leu Glu Trp Val
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
            115

```
<210>      13
<211>      119
<212>      PRT
<213>      Artificial

<220>
<223>      amino acid sequences of variable region of the heavy chain (VH)
           of humanized B-Ly1 antibody (B-HL11)

<400>      13
```

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Val
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
            115

```
<210>      14
<211>      119
<212>      PRT
<213>      Artificial
```

SEQUENCE LISTING

```
<220>
<223>   amino acid sequences of variable region of the heavy chain (VH)
        of humanized B-Ly1 antibody (B-HL12)

<400>   14

Glu Val Gln Leu Val Glu Ser Gly Ala Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser
            115

<210>   15
<211>   119
<212>   PRT
<213>   Artificial

<220>
<223>   amino acid sequences of variable region of the heavy chain (VH)
        of humanized B-Ly1 antibody (B-HL13)

<400>   15

Glu Val Gln Leu Val Glu Ser Gly Gly Gly Val Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser
            115

<210>   16
<211>   119
<212>   PRT
<213>   Artificial

<220>
<223>   amino acid sequences of variable region of the heavy chain (VH)
        of humanized B-Ly1 antibody (B-HL14)

<400>   16

Glu Val Gln Leu Val Glu Ser Gly Gly Gly Leu Lys Lys Pro Gly Gly
```

-continued

SEQUENCE LISTING

```
                1               5                      10                      15
Ser Leu Arg Leu Ser Cys Ala Ala Ser Gly Phe Thr Phe Ser Tyr Ser
                    20                      25                      30

Trp Met Asn Trp Val Arg Gln Ala Pro Gly Lys Gly Leu Glu Trp Met
            35                      40                      45

Gly Arg Ile Phe Pro Gly Asp Gly Asp Thr Asp Tyr Asn Gly Lys Phe
        50                      55                      60

Lys Gly Arg Val Thr Ile Thr Ala Asp Lys Ser Thr Ser Thr Ala Tyr
65                      70                      75                      80

Met Glu Leu Ser Ser Leu Arg Ser Glu Asp Thr Ala Val Tyr Tyr Cys
                    85                      90                      95

Ala Arg Asn Val Phe Asp Gly Tyr Trp Leu Val Tyr Trp Gly Gln Gly
                100                     105                     110

Thr Leu Val Thr Val Ser Ser
            115

<210>   17
<211>   119
<212>   PRT
<213>   Artificial

<220>
<223>   amino acid sequences of variable region of the heavy chain (VH)
        of humanized B-Ly1 antibody (B-HL15)

<400>   17

Glu Val Gln Leu Val Glu Ser Gly Gly Gly Leu Val Lys Pro Gly Ser
1               5                       10                      15

Ser Leu Arg Leu Ser Cys Ala Ala Ser Gly Phe Thr Phe Ser Tyr Ser
                    20                      25                      30

Trp Met Asn Trp Val Arg Gln Ala Pro Gly Lys Gly Leu Glu Trp Met
            35                      40                      45

Gly Arg Ile Phe Pro Gly Asp Gly Asp Thr Asp Tyr Asn Gly Lys Phe
        50                      55                      60

Lys Gly Arg Val Thr Ile Thr Ala Asp Lys Ser Thr Ser Thr Ala Tyr
65                      70                      75                      80

Met Glu Leu Ser Ser Leu Arg Ser Glu Asp Thr Ala Val Tyr Tyr Cys
                    85                      90                      95

Ala Arg Asn Val Phe Asp Gly Tyr Trp Leu Val Tyr Trp Gly Gln Gly
                100                     105                     110

Thr Leu Val Thr Val Ser Ser
            115

<210>   18
<211>   119
<212>   PRT
<213>   Artificial

<220>
<223>   amino acid sequences of variable region of the heavy chain (VH)
        of humanized B-Ly1 antibody (B-HL16)

<400>   18

Glu Val Gln Leu Val Glu Ser Gly Gly Gly Leu Val Lys Pro Gly Gly
1               5                       10                      15

Ser Leu Arg Val Ser Cys Ala Ala Ser Gly Phe Thr Phe Ser Tyr Ser
                    20                      25                      30

Trp Met Asn Trp Val Arg Gln Ala Pro Gly Lys Gly Leu Glu Trp Met
            35                      40                      45
```

-continued

SEQUENCE LISTING

```
Gly Arg Ile Phe Pro Gly Asp Gly Asp Thr Asp Tyr Asn Gly Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
                100                 105                 110

Thr Leu Val Thr Val Ser Ser
        115

<210>  19
<211>  119
<212>  PRT
<213>  Artificial

<220>
<223>  amino acid sequences of variable region of the heavy chain (VH)
       of humanized B-Ly1 antibody (B-HL17)

<400>  19

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Tyr Ser
                 20                  25                  30

Trp Met Asn Trp Val Arg Gln Ala Pro Gly Lys Gly Leu Glu Trp Met
             35                  40                  45

Gly Arg Ile Phe Pro Gly Asp Gly Asp Thr Asp Tyr Asn Gly Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
                100                 105                 110

Thr Leu Val Thr Val Ser Ser
        115

<210>  20
<211>  115
<212>  PRT
<213>  Artificial

<220>
<223>  amino acid sequences of variable region of the light chain (VL)
       of humanized B-Ly1 antibody B-KV1

<400>  20

Asp Ile Val Met Thr Gln Thr Pro Leu Ser Leu Pro Val Thr Pro Gly
  1               5                  10                  15

Glu Pro Ala Ser Ile Ser Cys Arg Ser Ser Lys Ser Leu Leu His Ser
                 20                  25                  30

Asn Gly Ile Thr Tyr Leu Tyr Trp Tyr Leu Gln Lys Pro Gly Gln Ser
             35                  40                  45

Pro Gln Leu Leu Ile Tyr Gln Met Ser Asn Leu Val Ser Gly Val Pro
 50                  55                  60

Asp Arg Phe Ser Gly Ser Gly Ser Gly Thr Asp Phe Thr Leu Lys Ile
 65                  70                  75                  80
```

SEQUENCE LISTING

```
Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val
        115
```

SEQUENCE LISTING

<160> NUMBER OF SEQ ID NOS: 22

<210> SEQ ID NO 1
<211> LENGTH: 112
<212> TYPE: PRT
<213> ORGANISM: Unknown
<220> FEATURE:
<223> OTHER INFORMATION: amino acid sequence of variable region of the heavy chain (VH) of murine monoclonal anti-CD20 antibody B-Ly1

<400> SEQUENCE: 1

```
Gly Pro Glu Leu Val Lys Pro Gly Ala Ser Val Lys Ile Ser Cys Lys
1               5                   10                  15

Ala Ser Gly Tyr Ala Phe Ser Tyr Ser Trp Met Asn Trp Val Lys Leu
            20                  25                  30

Arg Pro Gly Gln Gly Leu Glu Trp Ile Gly Arg Ile Phe Pro Gly Asp
        35                  40                  45

Gly Asp Thr Asp Tyr Asn Gly Lys Phe Lys Gly Lys Ala Thr Leu Thr
    50                  55                  60

Ala Asp Lys Ser Ser Asn Thr Ala Tyr Met Gln Leu Thr Ser Leu Thr
65                  70                  75                  80

Ser Val Asp Ser Ala Val Tyr Leu Cys Ala Arg Asn Val Phe Asp Gly
                85                  90                  95

Tyr Trp Leu Val Tyr Trp Gly Gln Gly Thr Leu Val Thr Val Ser Ala
            100                 105                 110
```

<210> SEQ ID NO 2
<211> LENGTH: 103
<212> TYPE: PRT
<213> ORGANISM: Unknown
<220> FEATURE:
<223> OTHER INFORMATION: amino acid sequence of variable region of the light chain (VL) of murine monoclonal anti-CD20 antibody B-Ly1

<400> SEQUENCE: 2

```
Asn Pro Val Thr Leu Gly Thr Ser Ala Ser Ile Ser Cys Arg Ser Ser
1               5                   10                  15

Lys Ser Leu Leu His Ser Asn Gly Ile Thr Tyr Leu Tyr Trp Tyr Leu
            20                  25                  30

Gln Lys Pro Gly Gln Ser Pro Gln Leu Leu Ile Tyr Gln Met Ser Asn
        35                  40                  45

Leu Val Ser Gly Val Pro Asp Arg Phe Ser Ser Gly Ser Gly Thr
    50                  55                  60

Asp Phe Thr Leu Arg Ile Ser Arg Val Glu Ala Glu Asp Val Gly Val
65                  70                  75                  80

Tyr Tyr Cys Ala Gln Asn Leu Glu Leu Pro Tyr Thr Phe Gly Gly Gly
                85                  90                  95
```

```
Thr Lys Leu Glu Ile Lys Arg
            100

<210> SEQ ID NO 3
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HH2)

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 4
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HH3)

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Leu Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 5
<211> LENGTH: 119
<212> TYPE: PRT
<213> ORGANISM: Artificial Sequence
<220> FEATURE:
```

<223> OTHER INFORMATION: amino acid sequences of variable region of the
heavy chain (VH) of humanized B-Ly1 antibody (B-HH4)

<400> SEQUENCE: 5

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115
```

<210> SEQ ID NO 6
<211> LENGTH: 119
<212> TYPE: PRT
<213> ORGANISM: Artificial Sequence
<220> FEATURE:
<223> OTHER INFORMATION: amino acid sequences of variable region of the
heavy chain (VH) of humanized B-Ly1 antibody (B-HH5)

<400> SEQUENCE: 6

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Met Ser Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115
```

<210> SEQ ID NO 7
<211> LENGTH: 119
<212> TYPE: PRT
<213> ORGANISM: Artificial Sequence
<220> FEATURE:
<223> OTHER INFORMATION: amino acid sequences of variable region of the
heavy chain (VH) of humanized B-Ly1 antibody (B-HH6)

<400> SEQUENCE: 7

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
```

-continued

```
                20                  25                  30
Trp Ile Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser
            115

<210> SEQ ID NO 8
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HH7)

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Ser Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser
            115

<210> SEQ ID NO 9
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HH8)

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Ser
            20                  25                  30

Trp Met Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
```

```
                65                  70                  75                  80
Met Glu Leu Ser Ser Leu Arg Ser Glu Asp Thr Ala Val Tyr Tyr Cys
                    85                  90                  95

Ala Arg Asn Val Phe Asp Gly Tyr Trp Leu Val Tyr Trp Gly Gln Gly
                100                 105                 110

Thr Leu Val Thr Val Ser Ser
        115

<210> SEQ ID NO 10
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HH9)

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Tyr Ser
                20                  25                  30

Trp Met Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Asn Val Phe Asp Gly Tyr Trp Leu Val Tyr Trp Gly Gln Gly
                100                 105                 110

Thr Leu Val Thr Val Ser Ser
        115

<210> SEQ ID NO 11
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HL8)

<400> SEQUENCE: 11

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Tyr Ser
                20                  25                  30

Trp Met Asn Trp Val Arg Gln Ala Pro Gly Lys Gly Leu Glu Trp Val
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Asn Val Phe Asp Gly Tyr Trp Leu Val Tyr Trp Gly Gln Gly
                100                 105                 110

Thr Leu Val Thr Val Ser Ser
```

-continued

```
        115

<210> SEQ ID NO 12
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HL10)

<400> SEQUENCE: 12

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Tyr Ser
            20                  25                  30

Trp Met Asn Trp Val Arg Gln Ala Pro Gly Lys Gly Leu Glu Trp Val
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser
        115

<210> SEQ ID NO 13
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HL11)

<400> SEQUENCE: 13

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Val
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser
        115

<210> SEQ ID NO 14
<211> LENGTH: 119
<212> TYPE: PRT
<213> ORGANISM: Artificial Sequence
<220> FEATURE:
<223> OTHER INFORMATION: amino acid sequences of variable region of the
``` heavy chain (VH) of humanized B-Ly1 antibody (B-HL12)

<400> SEQUENCE: 14

Glu Val Gln Leu Val Glu Ser Gly Ala Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 15
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HL13)

<400> SEQUENCE: 15

Glu Val Gln Leu Val Glu Ser Gly Gly Gly Val Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 16
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HL14)

<400> SEQUENCE: 16

Glu Val Gln Leu Val Glu Ser Gly Gly Gly Leu Lys Lys Pro Gly Gly
1               5                   10                  15

Ser Leu Arg Leu Ser Cys Ala Ala Ser Gly Phe Thr Phe Ser Tyr Ser
            20                  25                  30

-continued

Trp Met Asn Trp Val Arg Gln Ala Pro Gly Lys Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 17
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HL15)

<400> SEQUENCE: 17

Glu Val Gln Leu Val Glu Ser Gly Gly Gly Leu Val Lys Pro Gly Ser
 1               5                  10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 18
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HL16)

<400> SEQUENCE: 18

Glu Val Gln Leu Val Glu Ser Gly Gly Gly Leu Val Lys Pro Gly Gly
 1               5                  10                  15

Ser Leu Arg Val Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 19
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HL17)

<400> SEQUENCE: 19

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
             85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 20
<211> LENGTH: 115
<212> TYPE: PRT
<213> ORGANISM: Artificial Sequence
<220> FEATURE:
<223> OTHER INFORMATION: amino acid sequences of variable region of the
      light chain (VL) of humanized B-Ly1 antibody B-KV1

<400> SEQUENCE: 20

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
            85                  90                  95

Leu Glu Leu Pro Tyr Thr Phe Gly Gly Gly Thr Lys Val Glu Ile Lys
            100                 105                 110

Arg Thr Val
        115

<210> SEQ ID NO 21
<211> LENGTH: 449
<212> TYPE: PRT
<213> ORGANISM: Artificial Sequence
<220> FEATURE:
<223> OTHER INFORMATION: amino acid sequences of variable region of the
      heavy chain of humanized B-Ly1 antibody

<400> SEQUENCE: 21

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
```

-continued

```
                355                 360                 365
Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 22
<211> LENGTH: 219
<212> TYPE: PRT
<213> ORGANISM: Artificial Sequence
<220> FEATURE:
<223> OTHER INFORMATION: amino acid sequences of variable region of the
      light chain of humanized B-Ly1 antibody

<400> SEQUENCE: 22

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

What is claimed is:

1. A stable aqueous pharmaceutical formulation, the formulation comprising: (a) a monoclonal antibody in an amount of about 35 mg/mL to about 75 mg/mL; (b) trehalose in an amount of about 40 mM to about 80 mM; (c) histidine in an amount of about 15 mM to about 35 mM; and (d) poloxamer in an amount of about 0.01% to about 0.05%; wherein the weight ratio of said monoclonal antibody to said trehalose in the formulation is about 1.65 to about 4.95, wherein the formulation has a pH of about 5.5 to about 7.0, and wherein the monoclonal antibody is obinutuzumab.

2. The formulation of claim 1, wherein the weight ratio of said monoclonal antibody to said trehalose is about 1.65 to about 3.30.

3. The formulation of claim 1, wherein the weight ratio of said monoclonal antibody to said trehalose is about 1.70 to about 2.91.

4. The formulation of claim 1, wherein the weight ratio of said monoclonal antibody to said trehalose is about 2.00 to about 3.30.

5. The formulation of claim 1, wherein said monoclonal antibody in the formulation is about 45 mg/mL to about 55 mg/mL.

6. The formulation of claim 1, wherein said monoclonal antibody in the formulation is about 50 mg/mL.

7. The formulation of claim 1, wherein said trehalose in the formulation is about 40 mM.

8. A stable aqueous pharmaceutical formulation, the formulation comprising: (a) a monoclonal antibody in an amount of about 35 mg/mL to about 75 mg/mL; (b) trehalose in an amount of about 40 mM to about 80 mM; (c) histidine in an amount of about 15 mM to about 35 mM; and (d) poloxamer in an amount of about 0.01% to about 0.05%; wherein said formulation has a pH of about 5.5 to about 7.0, and wherein the monoclonal antibody is obinutuzumab.

9. The formulation of claim 8, wherein the weight ratio of said monoclonal antibody to said trehalose in the formulation is between about 1.65 to about 3.30.

10. The formulation of claim 8, wherein the weight ratio of said monoclonal antibody to said trehalose in the formulation is between about 1.70 to about 2.91.

11. The formulation of claim 8, wherein said monoclonal antibody is in an amount of about 45 mg/mL to about 55 mg/mL.

12. The formulation of claim 8, wherein said monoclonal antibody is in an amount of about 50 mg/mL.

13. The formulation of claim 8, wherein said trehalose is in an amount of about 40 mM.

14. The formulation of claim 8, wherein said histidine is in an amount of about 20 mM to about 30 mM.

15. The formulation of claim 8, wherein said histidine is in an amount of about 20 mM.

16. The formulation of claim 8, wherein said monoclonal antibody is in an amount of about 50 mg/mL; said trehalose is in an amount of about 40 mM; said histidine is in an amount of about 20 mM; and said poloxamer is in an amount of about 0.02%.

17. The formulation of claim 1, wherein said poloxamer is poloxamer 188.

18. The formulation of claim 1, wherein said poloxamer concentration is about 0.02%.

19. The formulation of claim 1, wherein said formulation has a pH of about 5.9 to about 6.5.

20. The formulation of claim 1, wherein said formulation has a pH of about 6.2 or about 6.0.

21. The formulation of claim 1, wherein said monoclonal antibody is not subject to prior lyophilization.

22. The formulation of claim 1, wherein said monoclonal antibody is susceptible to aggregation.

23. The formulation of claim 1, wherein the formulation is stable at −20° C. or −40° C. for at least 12 months, at least 18 months, or at least 24 months.

24. The formulation of claim 1, which is sterile.

25. The formulation of claim 1, which is administered to a subject.

26. The formulation of claim 1, which is for intravenous (IV), subcutaneous (SQ), or instramuscular (IM) administration.

27. The formulation of claim 1, wherein said monoclonal antibody is in an amount of about 50 mg/mL, said trehalose is in an amount of about 40 mM, said histidine is in an amount of about 20 mM, and said poloxamer is poloxamer 188 in an amount of about 0.02%, and said formulation has a pH of about 6.0.

28. An article of manufacture comprising a container holding the stable aqueous pharmaceutical formulation of claim 1.

29. The formulation of claim 1, wherein said histidine is in an amount of about 20 mM.

30. The formulation of claim 8, wherein the weight ratio of said monoclonal antibody to said trehalose is about 2.00 to about 3.30.

31. The formulation of claim 8, wherein said poloxamer is poloxamer 188.

32. The formulation of claim 8, wherein said poloxamer concentration is about 0.02%.

33. The formulation of claim 8, wherein said formulation has a pH of about 5.9 to about 6.5, about 6.2, or about 6.0.

34. The formulation of claim 8, wherein said monoclonal antibody is not subject to prior lyophilization.

35. The formulation of claim 8, wherein the formulation is stable at −20° C. or −40° C. for at least 12 months, at least 18 months, or at least 24 months.

* * * * *